United States Patent
Tsukada et al.

(10) Patent No.: US 11,862,359 B2
(45) Date of Patent: Jan. 2, 2024

(54) CONDUCTIVE POLYMER FIBERS, METHOD AND DEVICE FOR PRODUCING CONDUCTIVE POLYMER FIBERS, BIOLOGICAL ELECTRODE, DEVICE FOR MEASURING BIOLOGICAL SIGNALS, IMPLANTABLE ELECTRODE, AND DEVICE FOR MEASURING BIOLOGICAL SIGNALS

(71) Applicant: NIPPON TELEGRAPH AND TELEPHONE CORPORATION, Tokyo (JP)

(72) Inventors: Shingo Tsukada, Atsugi (JP); Hiroshi Nakashima, Atsugi (JP); Akiyoshi Shimada, Tokyo (JP); Koji Sumitomo, Atsugi (JP); Keiichi Torimitsu, Atsugi (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 787 days.

(21) Appl. No.: 16/171,589

(22) Filed: Oct. 26, 2018

(65) Prior Publication Data
US 2019/0066866 A1 Feb. 28, 2019

Related U.S. Application Data

(63) Continuation of application No. 13/261,900, filed as application No. PCT/JP2012/079805 on Nov. 16, 2012, now Pat. No. 10,153,065.

(30) Foreign Application Priority Data

Nov. 17, 2011 (JP) ................................ 2011-251524
Aug. 24, 2012 (JP) ................................ 2012-185343

(Continued)

(51) Int. Cl.
*H01B 1/12* (2006.01)
*D06M 13/148* (2006.01)
(Continued)

(52) U.S. Cl.
CPC ............. *H01B 1/127* (2013.01); *D06M 11/74* (2013.01); *D06M 11/83* (2013.01);
(Continued)

(58) Field of Classification Search
CPC . A61B 5/268–27; D06M 11/74; D06M 11/83; D06M 11/148; D06M 11/256
See application file for complete search history.

(56) References Cited

U.S. PATENT DOCUMENTS 2,676,896 A 4/1954 Cohen
4,738,757 A * 4/1988 Naarmann ............... H01M 4/60
427/222

(Continued)

FOREIGN PATENT DOCUMENTS

CN 1860261 A 11/2006
CN 101019248 A 8/2007
(Continued)

OTHER PUBLICATIONS

"JP2011001391_Machine Translation" is a machine translation of JP-2011001391-A. (Year: 2011).*
(Continued)

*Primary Examiner* — Larissa Rowe Emrich
(74) *Attorney, Agent, or Firm* — Harness, Dickey & Pierce, P.L.C.

(57) ABSTRACT

Conductive polymer fibers 10, in which a conductor 12 containing a conductive polymer impregnates and/or adheres to base fibers 11, and the aforementioned conductive polymer is PEDOT-PSS.

18 Claims, 48 Drawing Sheets

(30) Foreign Application Priority Data

Aug. 29, 2012 (JP) ................................. 2012-189102
Sep. 26, 2012 (JP) ................................. 2012-212998

(51) Int. Cl.

| | | |
|---|---|---|
| D06M 15/356 | (2006.01) | |
| D06M 11/83 | (2006.01) | |
| D06M 11/74 | (2006.01) | |
| D06M 15/61 | (2006.01) | |
| D06P 1/38 | (2006.01) | |
| D06M 15/53 | (2006.01) | |
| D06M 15/256 | (2006.01) | |
| H01B 13/30 | (2006.01) | |
| D06M 23/10 | (2006.01) | |
| A61B 5/25 | (2021.01) | |
| A61B 5/283 | (2021.01) | |
| A61B 5/291 | (2021.01) | |

(52) U.S. Cl.
CPC ........ *D06M 13/148* (2013.01); *D06M 15/256* (2013.01); *D06M 15/356* (2013.01); *D06M 15/53* (2013.01); *D06M 15/61* (2013.01); *D06P 1/38* (2013.01); *H01B 1/12* (2013.01); *H01B 13/30* (2013.01); *A61B 5/25* (2021.01); *A61B 5/283* (2021.01); *A61B 5/291* (2021.01); *A61B 2560/063* (2013.01); *A61B 2562/0215* (2017.08); *A61B 2562/043* (2013.01); *A61B 2562/046* (2013.01); *A61B 2562/125* (2013.01); *D06M 23/10* (2013.01); *Y10T 428/292* (2015.01); *Y10T 428/2944* (2015.01); *Y10T 428/2958* (2015.01); *Y10T 428/2962* (2015.01); *Y10T 428/2967* (2015.01)

(56) References Cited

U.S. PATENT DOCUMENTS

| | | | | |
|---|---|---|---|---|
| 4,830,779 | A | * | 5/1989 | Maeno ................. C08K 3/08 524/379 |
| 4,859,989 | A | | 8/1989 | McPherson |
| 6,228,492 | B1 | * | 5/2001 | Kinlen ............... D06M 15/227 264/131 |
| 10,153,065 | B2 | * | 12/2018 | Tsukada ............... H01B 13/30 |
| 2004/0053049 | A1 | * | 3/2004 | Tsunashima ........... D06M 11/83 428/375 |
| 2004/0138546 | A1 | | 7/2004 | Reho et al. |
| 2007/0054577 | A1 | | 3/2007 | Avloni |
| 2007/0085061 | A1 | * | 4/2007 | Elder ................. H01G 9/028 252/500 |
| 2007/0089800 | A1 | * | 4/2007 | Sharma ................ D04B 1/14 139/388 |
| 2008/0017833 | A1 | | 1/2008 | Louwet et al. |
| 2008/0170982 | A1 | | 7/2008 | Zhang et al. |
| 2009/0005667 | A1 | | 1/2009 | Cui et al. |
| 2009/0099441 | A1 | | 4/2009 | Giszter et al. |
| 2009/0105796 | A1 | | 4/2009 | Atanasoska et al. |
| 2009/0171406 | A1 | | 7/2009 | Foley et al. |
| 2009/0269511 | A1 | | 10/2009 | Zhamu et al. |
| 2009/0305135 | A1 | | 12/2009 | Shi et al. |
| 2010/0106259 | A1 | | 4/2010 | Llinas et al. |
| 2010/0245971 | A1 | * | 9/2010 | Sotzing ................ D03D 15/47 359/265 |
| 2011/0087315 | A1 | | 4/2011 | Richardson-Burns et al. |
| 2011/0151254 | A1 | * | 6/2011 | Fugetsu ............... D06M 10/06 428/368 |
| 2011/0293218 | A1 | | 12/2011 | Pettit |
| 2012/0021547 | A1 | | 1/2012 | Kawanishi |
| 2012/0204950 | A1 | | 8/2012 | Magdassi et al. |
| 2012/0224247 | A1 | | 9/2012 | Sotzing et al. |
| 2014/0231118 | A1 | * | 8/2014 | Koziol ................. H01B 3/46 174/110 R |
| 2014/0277318 | A1 | | 9/2014 | Richardson-Burns et al. |
| 2016/0333503 | A1 | | 11/2016 | Shen et al. |

FOREIGN PATENT DOCUMENTS

| | | |
|---|---|---|
| CN | 101536903 A | 9/2009 |
| CN | 201379569 Y | 1/2010 |
| CN | 102008300 A | 4/2011 |
| EP | 0778046 A2 | 6/1997 |
| EP | 1674036 A1 | 6/2006 |
| JP | H06114019 A | 4/1994 |
| JP | H06-200476 A | 7/1994 |
| JP | H11-081137 A | 3/1999 |
| JP | 3153409 B2 | 4/2001 |
| JP | 2001-262489 A | 9/2001 |
| JP | 2002224051 A | 8/2002 |
| JP | 2007012510 A | 1/2007 |
| JP | 2007-521405 A | 8/2007 |
| JP | 2007296266 A | 11/2007 |
| JP | 2009-500609 A | 1/2009 |
| JP | U-B-3153409 | 8/2009 |
| JP | 2010170829 A | 8/2010 |
| JP | 2010540105 A | 12/2010 |
| JP | 2011-001391 A | 1/2011 |
| JP | 2011001391 A * | 1/2011 |
| JP | 2011104338 A | 6/2011 |
| JP | 2011-183098 A | 9/2011 |
| JP | 2012104737 A | 5/2012 |
| JP | 2012-186452 A | 9/2012 |
| JP | 3178230 U | 9/2012 |
| WO | WO-03039337 A2 | 5/2003 |
| WO | WO-2005047576 A1 | 5/2005 |
| WO | WO-2005103186 A1 | 11/2005 |
| WO | WO-2007/005770 A1 | 1/2007 |
| WO | WO-2007094464 A1 | 8/2007 |
| WO | WO-2007/099889 A1 | 9/2007 |
| WO | WO-2008/066458 A1 | 6/2008 |
| WO | WO-2011055291 A1 | 5/2011 |
| WO | WO-2011100059 A1 | 8/2011 |
| WO | WO-2011130335 A2 | 10/2011 |
| WO | WO-2012007374 A1 | 1/2012 |

OTHER PUBLICATIONS

Irwin, M.D., Roberson, D.A., Olivas, R.I. et al. Conductive polymer-coated threads as electrical interconnects in e-textiles. Fibers Polym 12, 904 (2011). https://doi.org/10.1007/s12221-011-0904-8 (Year: 2011).*
Invernale, Michael A. et al., "All-Organic Electrochromic Spandex", ACS Applied Material & Interfaces, 2010, 2, 1, 296-300. DOI: 10.1021/am900767p; Jan. 4, 2010.
Barker, Robert H., "Additives in Fibers and Fabrics", Environmental Health Perspectives, vol. 11, pp. 41-45, 1975.
"Spinning and Characterization of Conducting Microfibers," Macromol. Rapid Commun. (2003) 24, pp. 261-264.
International Search Report for PCT/JP2012/079805, ISA/JP, dated Feb. 19, 2013 with translation thereof.
Yong Hyun Kim et al: "Highly Conductive PEDOT: PSS Electrode with Optimized Solvend and Thermal Post-Treatment for ITO-Free Organic Solar Cells", Advanced Functional Materials, Wiley—VCH Verlag GMBH & Co. KGAA, DE, vol. 21, No. 6, Mar. 22, 2011 (Mar. 22, 2011), pp. 1076-1081.
Office Action for corresponding application EP 13850492.5, EPO, dated Nov. 8, 2016.
Fengling Zhang et al., Polymer Photovoltaic Cells with Conducting Polymer Anodes, Advanced Materials, Germany, John Wiley & Sons, Inc., May 3, 2002, vol. 14, Issue 9, 662-665.
Kazuhiro Marumoto et al., Improved Efficiency of Bulk-Heterojunction Organic Thin-film Solar Cells by Adding Glycerol to PEDOT:PSS Solutions for Fabricating Buffer Layers, Japan Institute of Energy, Japan, general incorporated foundation Japan Institute of Energy, May 31, 2011, vol. 90, No. 5, 461-465.

(56) References Cited

OTHER PUBLICATIONS

Hamedi M et al: "Towards Woven Logic from Organic Electronic Fibres", Nature Materials, Nature Publishing Group, London, GB, vol. 6, May 1, 2007 (May 1, 2007), pp. 357-362, XP003021530, ISSN: 1476-4660, DOI: 10.1038/NMAT1884.
Office Action in parallel application JP 2016-009205, JPO, dated Jun. 6, 2017 with translation thereof.
Extended European Search Report for parallel application EP 17162838, EPO, Munich, dated Jun. 13, 2017.
Office Action for parallel application 201511013932.0, SIPO, dated Feb. 13, 2018, with partial English translation of search report.
Search Report, European Patent Application No. 12850492.5, dated Dec. 5, 2014.
Office Action, Chinese Patent Application No. 201280056491.0, dated Jan. 27, 2015.
Notice of Allowance, Japanese Patent Application No. 2013-544344, dated Feb. 24, 2015.
Notice of Allowance, Japanese Patent Application No. 2014-238289, dated Feb. 24, 2015.
Notice of Allowance, Japanese Patent Application No. 2014-238290, dated Feb. 24, 2015.
Extended European Search Report, Patent Application No. 15171688.3, dated Dec. 21, 2015.
Notice of Reasons for Rejection, Japanese Patent Application No. 2014-238291, dated Nov. 24, 2015.
Ding, Yujie, et al., "Conductivity Trends of PEDOT-PSS Impregnated Fabric and the Effect of Conductivity on Electrochromic Textile," ACS Applied Materials & Interfaces, vol. 2, No. 6, Jun. 23, 2010, pp. 1588-1593.
Communication pursuant to Article 94(3) EPC, European Patent Application No. 12 850 492.5, dated Apr. 7, 2016.
Irwin et al. "Conductive Polymer-Coated Threads as Electrical Interconnects in e-Textiles" Fibers and Polymers 2011, vol. 12, No. 7, pp. 904-910.
Hosseini, et al. "Preparation of Conducting Fibres from Cellulose and Silk by Polypyrrole Coating," Iranian Polymer Journal (English Edition) 14(11) pp. 934-940 (2005).
Yoshiro Eto, "The latest/The Complete Works of Conductive polymer", pp. 42-43, 175- 177, issued on Dec. 27, 2007.
Japanese Information Statement regarding JPSN 2018075028, mailed Mar. 26, 2019.
Office Action, U.S. Appl. No. 13/261,900, dated May 18, 2017.
Office Action, U.S. Appl. No. 13/261,900, dated Aug. 24, 2017.
Final Office Action, U.S. Appl. No. 13/261,900, dated Feb. 7, 2018.
Notice of Allowance, U.S. Appl. No. 13/261,900, dated Jul. 26, 2018.
Japanese Office Action from counterpart JP2018075028, dated Mar. 17, 2020.
Japanese Office Action from counterpart JP2019097056, dated Mar. 17, 2020.
U.S. Appl. No. 13/261,900, filed May 14, 2014.
Japanese Office Action from counterpart JP2019033328, dated Feb. 12, 2020.
Japanese Office Action regarding JPSN 2018075028, dated Jan. 22, 2019.
Invernale, M. A., et al. "All-Organic Electrochromic Spandex" (2010) ACS Applied Materials and Interfaces 2(1):296-300.†
Invernale, M. A., et al. Supporting Information for "All-Organic Electrochromic Spandex" (2010) ACS Applied Materials and Interfaces 2(1):296-300. Accessible at pubs.acs.org/doi/abs/10.1021/am900767p.†

\* cited by examiner
† cited by third party

MEASUREMENT EXAMPLE OF ELECTROCARDIOGRAM OF HUMAN

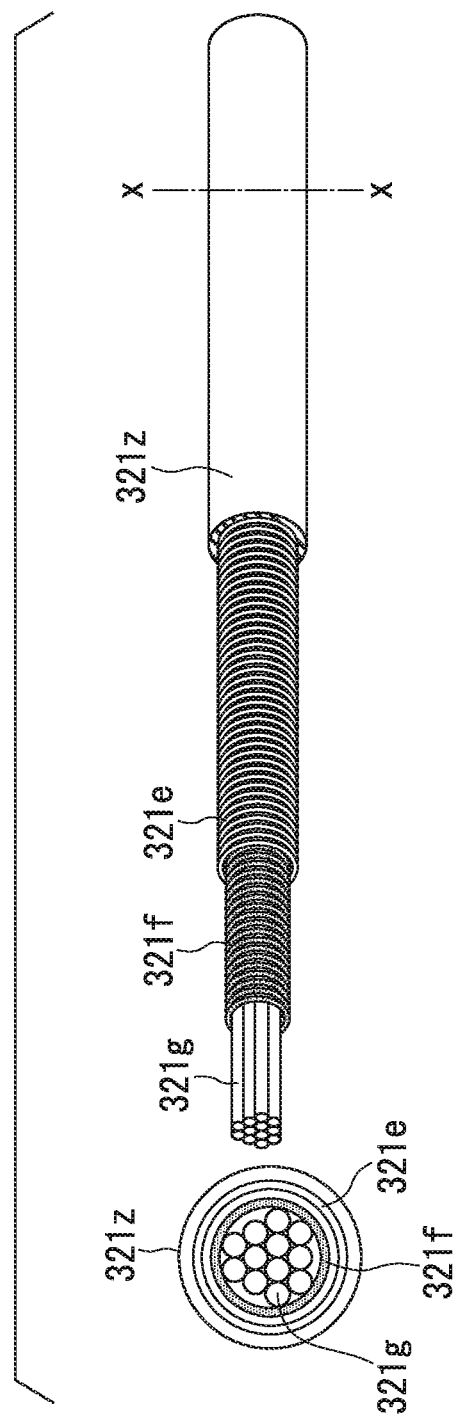

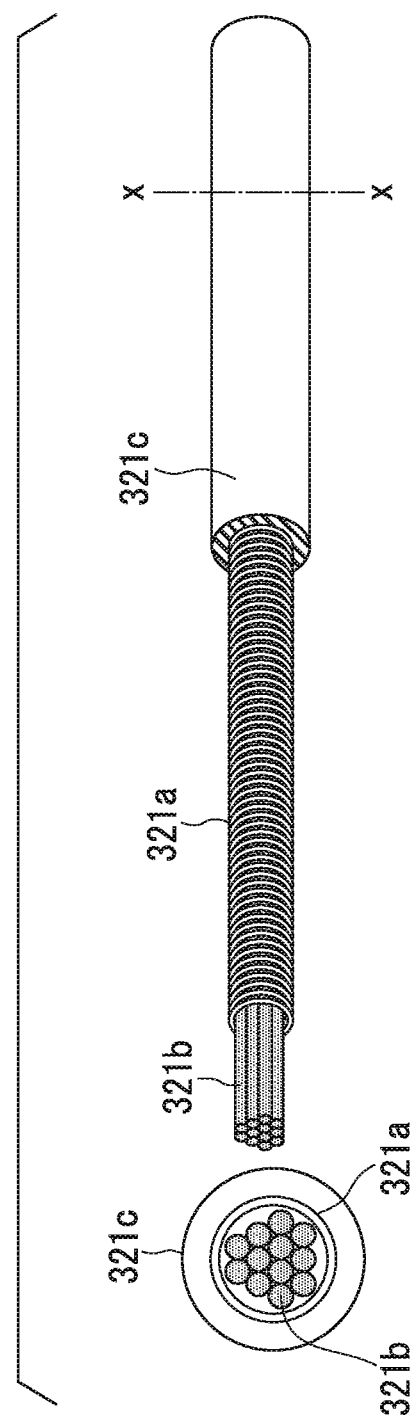

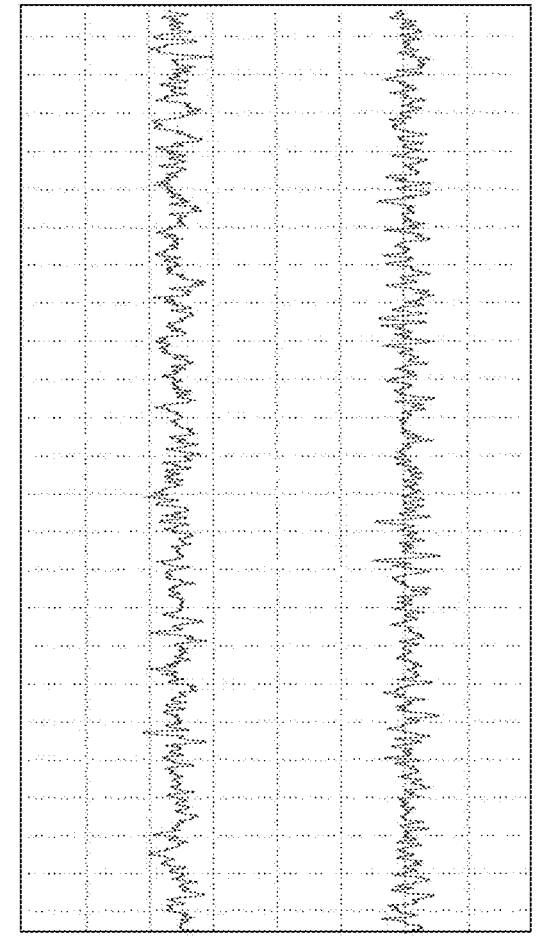

MEASUREMENT EXAMPLE OF AUDITORY BRAIN-STEM RESPONSE (ABR) (HUMAN)

CONDUCTIVE POLYMER FIBERS, METHOD AND DEVICE FOR PRODUCING CONDUCTIVE POLYMER FIBERS, BIOLOGICAL ELECTRODE, DEVICE FOR MEASURING BIOLOGICAL SIGNALS, IMPLANTABLE ELECTRODE, AND DEVICE FOR MEASURING BIOLOGICAL SIGNALS

CROSS REFERENCE TO RELATED APPLICATIONS

This application is a continuation of U.S. application Ser. No. 13/261,900 filed May 14, 2014 which is a 371 U.S. National Stage of International Application No. PCT/JP2012/079805, filed Nov. 16, 2012. Priority is claimed on Japanese Patent Application No. 2011-251524, filed Nov. 17, 2011; Japanese Patent Application No. 2012-185343, filed Aug. 24, 2012; Japanese Patent Application No. 2012-189102, filed Aug. 29, 2012; and Japanese Patent Application No. 2012-212998, filed Sep. 26, 2012, the content of which is incorporated herein by reference.

TECHNICAL FIELD

The present invention relates to conductive polymer fibers, a method and a device for producing conductive polymer fibers, a biological electrode, a device for measuring biological signals, an implantable electrode, and another device for measuring biological signals.

BACKGROUND ART

Conventionally, as conductive fibers, there are known to be fibers that have a fiber surface coated with metal such as copper, or that are interwoven with fine wire of carbon or metal, conductive fibers that is a conductive polymer formed into a cord-like shape, and so on. These conductive fibers are widely used in biological electrodes, biointerfaces, antistatic clothing, and the like. However, conductive materials such as metal or carbon are hydrophobic and hard, resulting in the problem that they are poorly compatible with applications involving contact with body surfaces and body tissues of living organisms that are highly moist and soft. For example, in the case where a biological electrode is set on a body surface, adhesion and direct conduction with the body surface are inhibited when the biological electrode is composed of hard hydrophobic material. Consequently, it is necessary to separately prepare and use conductive paste (jelly) that electrically connects the bioelectrode and the body surface.

In recent years, as material having satisfactory compatibility with living bodies, development has advanced with respect to conductive fibers that are molded into thread-like form by extruding an aqueous solution of PEDOT-PSS {poly(3,4-ethylenedioxythiophene)-poly(styrene sulfonic acid)} that is a conductive polymer with particularly good conductivity and hydrophilicity from a nozzle into an acetone coagulation bath. Commercialization thereof is also under study (see, e.g., Non-Patent Document 1).

However, when conductive fibers composed of the aforementioned PEDOT-PSS are used in a high-humidity environment, there is the problem that the PEDOT-PSS absorbs moisture, and that strength (particularly tensile strength) declines. Moreover, conductive fibers composed of PEDOT-PSS expand when they absorb moisture, and conversely contract when dried. Consequently, as a result of cracking that occurs within the fibers, or fracturing of the fibers, there is the problem that the conductivity of the fibers tends to decline or be lost.

Clothing is susceptible to becoming water-soaked during use due to rain or perspiration. The usage environment of biological electrodes and biointerfaces is essentially a high-humidity one. Accordingly, resolution of the aforementioned problems is required in order to utilize PEDOT-PSS with its excellent conductivity and hydrophilicity in these wide-ranging applications.

In addition to the aforementioned problem that conductive fibers composed of PEDOT-PSS undergo a marked decline in strength when they contain moisture, there is also the following problem. That is, the aforementioned fibers produced by the wet-spinning method recorded in the Non-Patent Document 1 are fine fibers with a diameter of approximately 10 microns. Consequently, there is the problem that handling is difficult, and that strength is insufficient when dry. Furthermore, the aforementioned fibers are highly rigid, and have a coarse feel. Consequently, there is also the issue that they are deficient in imparting the suppleness required by applications such as clothing.

On the other hand, biological electrodes of the body surface attachment type are widely used for recording bioelectrical signals such as brain waves, event-related potential, evoked potential, electromyograms, and electrocardiograms, and for electrically stimulating living bodies. (Biological electrodes of the body surface attachment type may be hereinafter referred to simply as "biological electrodes.")

The biological electrodes that have heretofore been in wide use are composed of a metallic electrode plate and gel or paste containing an electrolyte solution. The basic structure of these biological electrodes uses (applies) gel or paste between the metallic electrode plate and the skin surface to fix the electrode plate to the skin surface. Due to attachment of the biological electrode, a prescribed position on the skin surface is constantly sealed. Consequently, particularly when there is continuous use over a long period, not only may a sense of discomfort or itchiness arise due to moldering perspiration, but also contact dermatitis or bacterial infections or the like may occur. Such problems of the prior art require resolution.

In the various countries with a growing elderly population, there are an increasing number of cases where monitoring of biosignals such as electrocardiograms is conducted over long periods. As various skin functions decline in elderly people, highly adhesive stick-on electrodes using conventional adhesive tape or the like tend to produce dermatitis or uncomfortable sensations such as itchiness. Furthermore, the trouble frequently occurs that wearers who exhibit dementia or nighttime delirium themselves remove the biological electrode, and such problems require corrective measures.

With respect to conventional biological electrodes that are susceptible to the aforementioned problems, gel or paste containing an electrolyte solution is used between the skin and the metallic electrode plate. In the case where a biological electrode is set on a skin surface via gel or paste, it is necessary to increase the contact area of the electrode. The reason is that, due to the low conductivity of gel or paste, it is necessary to reduce electrode resistance by expanding the area of contact with skin. However, expansion of the electrode contact area is the primary cause of occurrence of the aforementioned problems.

Thus, the existing biological electrode configuration that relies on electrolytic gel or paste is deficient in wear comfort, and inhibits further downsizing and increased density of the electrode.

On the other hand, an implantable biological electrode is necessary in order to have an external device accurately and efficiently receive electrical signals from within a living body, and conversely to have an external device transmit electrical signals into a living body. Signals of action potential and synaptic potential of nerve cells are particularly weak. Consequently, if an electrode is not set very close to the cells, there are many signals that would be difficult to measure and input. Even apart from the nervous system, implantable biological electrodes are widely used in cardiac pacemakers, cochlear implants, and so on. Moreover, with respect to future human interfaces, development is advancing with respect to implantable biological electrodes for brain-machine interface and the like.

The living body consists of an abundance of water and electrolytes, as well as soft tissue. In contrast, conventional biological electrodes for implantation into living bodies are fabricated using conductive material that is hard and hydrophobic such as metal or carbon. Consequently, there have been problems of mechanical and electrochemical compatibility between conventional biological electrodes and biological tissue.

In particular, there are the problems that inflammation occurs due to mechanical stress arising at the boundary of the biological electrode and the biological tissue, and that tissue is impaired (invaded).

Within biological tissue, as well, the following problems may occur when electrodes are implanted into nerve tissue of central nervous system. That is, inflammation provoked by minute injuries to nerve tissue may gradually expand, resulting in degeneration and separation of nerve cells around the electrode, and inhibiting measurement and stimulation (signal input). Particularly with respect to permanent implantation of electrodes into tissue, there is loss and glial scarring of nerve cells, leading to reduced efficiency of electrical stimulation, and degradation and loss of measured waveforms. In addition, there is also the risk of causing functional impairment to nerves due to the loss of nerve cells. In view of these matters, corrective measures are required.

PRIOR ART DOCUMENTS

Non Patent Documents

Non-Patent Document 1: "Spinning and Characterization of Conducting Microfibers," Macromol. Rapid Commun. (2003) 24, pp. 261-264.

DISCLOSURE OF INVENTION

Problems to be Solved by the Invention

In the present invention, in order to overcome the aforementioned problems of conductive fibers composed of PEDOT-PSS, a composite material has been proposed wherein the PEDOT-PSS that is a conductive polymer is fixed to the interior and/or exterior of fibers or a fiber bundle (yarn) of silk or the like. As conductive fibers composed of such composite material of PEDOT-PSS have conductivity, hydrophilicity, tensile strength, and water-resistant strength, they can be expected to serve as material for biological electrodes in particular.

Heretofore, commercial PEDOT-PSS material (e.g., CLEVIOS® P produced by Heraeus, Ltd.) has been supplied as PEDOT-PSS solution, and has generally been used by fixation onto a base material. There are broadly considered to be two types of methods for fixation of PEDOT-PSS in this manner, a chemical method and an electrochemical method. The chemical method is a relatively simple fixation method, and is capable of fixing PEDOT-PSS to a variety of base materials, but its conductivity and strength are not as high as those of the below-mentioned electrochemical method. The electrochemical method is a method for electrically polymerizing and fixing PEDOT-PSS to an electrode surface, and exhibits conductivity and strength that are superior to the chemical method, but it is necessary to use conductive material in the base material due to the need for energization between the base material and the solution.

Now, when producing the aforementioned type of composite fibers comprising PEDOT-PSS and a fiber bundle, the electrochemical method ordinarily cannot be used, because the fiber bundle constituting the base material is an insulator (non-conductive), and the chemical fixation method must be used. Specifically, production can be conducted by a method wherein a fiber bundle impregnated with PEDOT-PSS is sprayed with or immersed in the liquid of an electrolytic solution consisting of magnesium oxide solution, or an organic solvent such as acetone, ethanol or methanol.

However, conductive polymer fibers consisting of a fiber bundle of PEDOT-PSS produced by the chemical fixation method is limited to, for example, conductivity of 40-50 MΩ/cm in No. 9 silk yarn (with a fiber bundle diameter of approximately 280 microns), and furthermore the adhesive strength of the PEDOT-PSS and the fiber bundle is low. As there is the drawback that the PEDOT-PSS consequently tends to peel, and that conductivity tends to decline, further improvement is necessary.

As a technique for fiberization of PEDOT-PSS, in addition to the foregoing, one may cite spinning methods (wet spinning or electrospinning). However, it is technically difficult to produce PEDOT-PSS blended with a lengthy fiber bundle (yarn) by spinning.

As a method for producing composite fibers consisting of PEDOT-PSS and a fiber bundle, one may also conceive of a method wherein either conductivity is imparted in advance by applying a metal coating to the fiber bundle, or conductivity is imparted upon fixation of the PEDOT-PSS to the fiber bundle by the chemical fixation method, and the PEDOT-PSS is electrochemically fixed by utilizing this conductivity as an electrode. However, as this method results in a production process that conducts fixation in two stages, it risks to have low productivity and high cost.

The aforementioned type of composite fibers comprising PEDOT-PSS and a fiber bundle of silk or the like have excellent biocompatibility, and are conductive material that is expected to have applications to biological electrodes. Although such composite fibers can be fabricated by the above-described chemical fixation method, there is a need for further improvement of conductivity and durability, and increased production efficiency.

Moreover, from a wide range of fields beginning with medical treatment, and including health promotion and information technology as well as wearable computers, demands are growing for biological electrodes of the body surface attachment type that are capable of continuous use over long periods. Requirements include not only a high degree of stability and reliability of bioelectrical signal measurement, but also wear comfort. There is also a need for implantable electrodes that are minimally invasive with respect to biological tissue.

Focusing on the high degree of hydrophilicity and suppleness of conductive polymers typified by the PEDOT-PSS that has been developed in recent years, the inventors of the present invention considered that it would be possible to alleviate the stress imparted to biological tissue when implanting conductive polymer into a living body as an electrode, and perfected the present invention as a result of diligent research.

The first to the fourth aspects of the present invention were achieved as a result of various studies by the present inventors, and in light of the aforementioned problems of the prior art. In the present invention, the conductive polymer fibers of the first aspect can be preferentially produced by the device and method of the second aspect. Moreover, the electrode and device of the third and fourth aspects can preferentially use the conductive polymer fibers of the first aspect.

The object of the first aspect of the present invention is to provide conductive polymer fibers with superior conductivity, strength in dry and wet states, and flexibility, as well as a biological electrode provided therewith.

The object of the second aspect of the present invention is to provide a method and a device for producing conductive polymer fibers, which enable a conductor containing PEDOT-PSS as a conductive polymer to impregnate or adhere to insulating fibers (a fiber bundle), and continuous electrochemical polymerization and fixation thereof, and which allow production with satisfactory productivity of conductive polymer fibers that are provided with a high degree of biocompatibility and satisfactory uniformity, and that have excellent conductivity and durability.

The object of the third aspect of the present invention is to provide a biological electrode which exhibits stability and reliability during measurement of bioelectrical signals, and which has an improved wear feeling compared to conventional biological electrodes, and a device for measuring biological signals which is provided with this biological electrode.

The object of the fourth aspect of the present invention is to provide an implantable electrode which enables detection of weak electrical signals from within a living body, which has excellent biological affinity, and which is minimally invasive with respect to biological tissue, and a device for measuring biological signals which is provided with this implantable electrode.

Means for Solving the Problems

The present invention provides very superior conductive polymer fibers, a method and a device for producing conductive polymer fibers, a biological electrode, a device for measuring biological signals, an implantable electrode, and another device for measuring biological signals, which are described in the following first aspect to fourth aspect.

(First Aspect)

The first aspect of the present invention provides the following conductive polymer fibers.

I-(1): A conductive polymer fiber of the first aspect of the present invention is a fiber, wherein a conductor containing a conductive polymer impregnates and/or adheres to base fibers, and the aforementioned conductive polymer is PEDOT-PSS.

The conductive polymer fiber of the first aspect of the present invention preferably has the following features.

I-(2): With respect to the aforementioned conductive polymer fiber, the conductor contains glycerol, polyethylene glycol-polypropylene glycol copolymer, ethylene glycol, sorbitol, sphingosine, or phosphatidylcholine as an additive.

I-(3): With respect to the conductive polymer fiber of either I-(1) or (2) above, the aforementioned conductor coats the circumference of the base fibers.

I-(4): With respect to the conductive polymer fiber of any one of I-(1) to (3) above, the interior of said base fibers is impregnated with said conductor.

I-(5): With respect to the conductive polymer fiber of any one of I-(1) to (4) above, the base fibers are impregnated with the conductor, metal or carbon coats a circumference of the base fibers, and a circumference of the metal or carbon coating is coated by the conductor.

I-(6): With respect to the conductive polymer fiber of any one of I-(1) to (5) above, among a plurality of the base fibers, the conductor is arranged with close adhesion to the base fibers.

I-(7): With respect to the conductive polymer fiber in any one of I-(1) to (5) above, an insulating layer is further arranged on a circumference of these conductive polymer fibers.

I-(8): A biological electrode of the present invention is provided with the conductive polymer fiber of any one of I-(1) to (7) above as an electrode.

(Second Aspect)

The second aspect of the present invention provides the following method and device for producing conductive polymer fibers.

II-(1): A method for producing a conductive polymer fiber of the present invention sequentially includes: an immersion step in which insulating base fibers consisting of a thread-like, cord-like, cloth-like or ribbon-like fiber bundle are immersed in a solution of a conductor containing PEDOT-PSS {poly(3,4-ethylenedioxythiophene)-poly(styrene sulfonic acid)} as a conductive polymer, thereby causing the conductor to impregnate and/or adhere to the base fibers; a fixation step in which the base fibers are energized by traveling between electrodes while being perpendicularly raised from the conductor solution, whereby the conductor that impregnates and/or adheres to the base fibers is electrochemically polymerized and fixed thereto; and a drying step in which the base fibers in which the conductor has been polymerized and fixed is subjected to blow drying; wherein the immersion step, the fixation step, and the drying step are respectively conducted while controlling atmospheric humidity.

Otherwise, the electrodes referred to herein include not only individual (monopolar) electrodes, but also configurations of multiple electrodes.

The aforementioned second aspect of II-(1) preferably has the following features.

II-(2): With respect to the fixation step in the method for producing conductive polymer fibers of the second aspect of the present invention, not only may an individual electrode be used, but it is also acceptable to use arrays of multiple electrodes.

Specifically, with respect to the fixation step, a method may be adopted wherein: multiple electrodes are used as the electrode(s), and the multiple electrodes are constituted by comb teeth-like electrodes having comb teeth that are multiply provided in a lengthwise direction of the base fibers; the comb teeth-like electrodes are disposed so as to sandwich the base fibers from the two sides of a radial direction of the base fibers, and the multiple comb teeth are disposed so as to combine in a respectively alternating manner in the lengthwise direction of the base fibers, from the two sides of a radial direction of the aforementioned base fibers; and the base fibers are energized by traveling while the aforementioned multiple comb teeth that are provided in the comb teeth-like electrodes are pressed against the base fibers from the two sides of a radial direction, and guide them.

II-(3): With respect to the fixation step in the method for producing a conductive polymer fiber of the second aspect of the present invention, it is preferable that: multiple electrodes are used as the electrode(s), where the multiple electrodes are constituted by rotor electrodes that are multiply disposed in a lengthwise direction of the base fibers, and that are disposed so as to sandwich the base fibers from the two sides of a radial direction of the base fibers; the rotor electrodes disposed on one side in a radial direction of the base fibers are roller-shaped, and the rotor electrodes disposed on the other side are pulley-shaped; the rotor electrodes that are disposed on both sides of the base fibers are disposed in a respectively alternating manner in a lengthwise direction of the base fibers; and the base fibers are energized by traveling between the respective multiple electrodes while the roller-like rotor electrodes are pressed against the base fibers, and hollows formed in the pulley-like rotor electrodes provide guidance.

II-(4): With respect to the fixation method in the method for producing a conductive polymer fiber of the second aspect of the present invention, it is more preferable to perform energization while controlling an amount of the conductor that impregnates and/or adheres to the base fibers, by ordering an arrangement of a fiber bundle by pressing the aforementioned roller-like rotor electrodes against the aforementioned base fibers while guiding them with hollows in the pulley-like rotor electrodes.

The second aspect of the present invention provides the following device for producing conductive polymer fibers.

II-(5): A device for producing a conductive polymer fiber of the second aspect of the present invention includes: an immersion container which internally houses a solution of a conductor containing PEDOT-PSS {poly(3,4-ethylenedioxythiophene)-poly(styrene sulfonic acid)} as a conductive polymer, and which immerses insulating base fibers consisting of a thread-like, cord-like, cloth-like, or ribbon-like fiber bundle in the conductor solution to cause the conductor to impregnate and/or adhere to the base fibers; a reel unit that serves to perpendicularly raise the aforementioned base fibers from the conductor solution housed in the immersion container; an electrode which energizes the aforementioned perpendicularly raised base fibers while they travel, thereby electrochemically polymerizing and fixing the conductor that has impregnated and/or adhered to the base fibers; a dryer which conducts drying by blowing air toward the aforementioned base fibers in which the conductor has been polymerized and fixed; and a humidity controller which serves to regulate atmospheric humidity near the base fiber.

The device of the present invention preferably also has the following features.

II-(6): A configuration is preferably adopted wherein the electrode consists of multiple electrodes, and the multiple electrodes are comb teeth-like electrodes having comb teeth that are multiply provided in the lengthwise direction of the base fibers; where the aforementioned comb teeth-like electrodes are disposed so as to sandwich the base fibers from the two sides of a radial direction of the base fibers, and the multiple comb teeth are disposed so as to combine in a respectively alternating manner in a lengthwise direction of the base fibers from the two sides of a radial direction of the aforementioned base fibers; and the base fibers are energized by traveling while the multiple comb teeth provided in the comb teeth-like electrodes are pressed against the fibers from the two sides of a radial direction of said base fibers, and guide the fibers.

II-(7): The device for producing a conductive polymer fiber of the second aspect of the present invention preferably has a configuration wherein: the aforementioned electrode consists of multiple electrodes; the multiple electrodes are rotor electrodes that are multiply disposed in a lengthwise direction of the base fibers, and that are disposed so as to sandwich the base fibers from the both sides of a radial direction of the base fibers; the rotor electrodes disposed on one side in a radial direction of the base fibers are roller-shaped, and the rotor electrodes disposed on another side are pulley-shaped; the rotor electrodes that are disposed on both sides of the base fibers are disposed in a respectively alternating manner in a lengthwise direction of the base fibers; and the base fibers are energized by traveling between the respective multiple electrodes while the aforementioned roller-like rotor electrodes are pressed against the base fibers, and hollows formed in the pulley-like rotor electrodes provide guidance.

II-(8): In the device for producing a conductive polymer fiber of the second aspect of the present invention, it is more preferable to configure the multiple electrodes so that energization is performed while controlling an amount of the conductor that impregnates and/or adheres to the base fibers, by ordering an arrangement of a fiber bundle by pressing the roller-like rotor electrodes against the base fibers, and providing guidance with hollows in the pulley-like rotor electrodes.

(Third Aspect)

The third aspect of the present invention provides the following biological electrode.

III-(1): A biological electrode, which uses a conductive composite fiber containing a conductive polymer.

The aforementioned biological electrode preferably has the following features.

III-(2): With respect to the biological electrode of III-(1) above, the electrode is provided with a cord-like, band-like, or cloth-like contact, which is composed of the aforementioned conductive composite fibers.

III-(3): With respect to the biological electrode of III-(2) above, the aforementioned contact is formed by multiply bundling the aforementioned conductive composite fiber, or is formed by winding the aforementioned conductive composite fiber onto a metallic wire material.

III-(4): With respect to the biological electrode of any one of III-(1) to (3) above, the aforementioned conductive composite fibers are adsorbent or hydrophilic relative to skin.

III-(5): With respect to the biological electrode of any one of III-(2) to (4) above, the aforementioned contacts are supported by an arcuate or a hairpin-like frame.

III-(6): With respect to the biological electrode of any one of III-(2) to (4) above, the aforementioned contacts are disposed on a surface of a sheet-like base material.

III-(7): With respect to the biological electrode of III-(6) above, a stretchable holder is provided on a rear surface of the aforementioned sheet-like base material, and the aforementioned holder is disposed so as to be slidable along the aforementioned rear surface.

The third aspect of the present invention provides the following device for measuring biological signals.

III-(8): A device for measuring biological signals, provided with the biological electrode of any one of III-(1) to (7) above.

(Fourth Aspect)

The fourth aspect of the present invention provides the following electrode.

IV-(1): An implantable electrode, provided with a conductive composite fiber containing a conductive polymer.

The implantable electrode of the present invention preferably has the following features.

IV-(2): With respect to the implantable electrode of IV-(1) above, the aforementioned conductive composite fibers are formed into a rod-like or coiled form.

IV-(3): With respect to the implantable electrode of IV-(1) or (2) above, the aforementioned conductive composite fiber has been adhered to a distal end of a needle.

IV-(4): With respect to the implantable electrode of IV-(3) above, the aforementioned conductive composite fibers has been adhered to the aforementioned needle via water-soluble adhesive material.

IV-(5): With respect to the implantable electrode of any one of IV-(1) to (4) above, the aforementioned conductive composite fibers are in a dry contracted state.

IV-(6): With respect to the implantable electrode of any one of IV-(1) to (5) above, an electric wire made of metal, silicone or carbon is connected to the aforementioned conductive composite fiber.

IV-(7): With respect to the implantable electrode of IV-(1) to (6) above, the aforementioned conductive composite fiber is formed into a rod or cord shape, and is used as a core part, and at least a portion of a circumference of said core part is coated with water-resistant polymer to form a flow path for permeation of liquid from one end to another end of the aforementioned coated core part.

IV-(8): With respect to the implantable electrode of IV-(7) above, a liquid including a drug is contained in the aforementioned flow path.

IV-(9): A biological signals measuring device, provided with the implantable electrode of any one of IV-(1) to (8) above.

The conductive composite fiber of IV-(1) to (8) above may include any one or more of glycerol, sorbitol, ethylene glycol, squalane, silicone, mineral oil, or MPC (2-methacryloyloxyethylphosphorylcholine). By including these, the speed with which moisture is absorbed in biological tissue by the aforementioned conductive composite fiber is slowed, enabling slowing of the swelling speed of the aforementioned conductive composite fiber. As a result, it is possible to inhibit swelling of conductive composite fiber and reduction of its mechanical strength during an operation to implant the aforementioned conductive composite fiber into biological tissue.

A reservoir or chamber allowing introduction of a pharmaceutical solution may be connected to the aforementioned one end of the conductive composite fiber of IV-(7) above. By introducing a solution including any one or more of the drugs of, for example, glycerol, sorbitol, mannitol, fructose, NGF (nerve growth factor), BDNF (Brain-derived neurotrophic factor), SKF96365, cilostazol, gadolinium, NT3 (neurotrophin-3), GSNO (S-nitrosoglutathione), magnesium, TRIM (1-(2-Trifluoromethylphenyl)imidazole), EGTA (ethylene glycol tetraacetic acid), or ruthenium red into the aforementioned reservoir or chamber, the solution can permeate from the one end to the other end of the conductive composite fiber that has been subjected to the coating. That is, it is possible to release the solution from the other end within the biological tissue, and locally administer a drug or the like contained in the solution to the surroundings of the conductive composite fiber.

One or more types of the drug may impregnate or be applied to the conductive composite fiber of any one of IV-(1) to (8) above. In this case, as well, the aforementioned drug can be gradually released from the conductive composite fiber that has been set within biological tissue, and the drug can be locally administered to the surroundings of the conductive composite fiber.

Thread may be connected to the conductive composite fiber of IV-(1), (2), (5), (6), or (7). Furthermore, a surgical needle may be tied to the aforementioned thread. By introducing the thread into a living body in advance, and by pulling the thread, thread connected to the thread can be smoothly introduced into biological tissue.

Effects of the Invention

The present invention is able to obtain the following excellent effects.

(Effects of the First Aspect)

According to the first aspect of the present invention, it is possible to provide conductive polymer fibers which have excellent conductivity, strength in dry and wet states, and flexibility, as well as a biological electrode provided therewith.

According to the conductive polymer fibers of I-(1) of the present invention, fibers are obtained which combine the high strength and flexibility of the base fibers, and the conductivity and hydrophilicity of the PEDOT-PSS that is a conductive polymer.

According to the configuration of I-(2), as the moisture absorption of the PEDOT-PSS can be inhibited by an additive, and as reduced strength due to occurrence of a wet state can be prevented, the conductive polymer fibers are higher strength fibers.

According to the configuration of I-(3), by coating the circumference of the base fibers with a conductor, the conductivity of the conductive polymer fibers is further increased, and conduction brought about by contact with multiple conductive polymer fibers is further facilitated.

According to the configuration of I-(4), as the base fibers are impregnated with the conductor, there is no risk of separation between the conductor and the base fibers, and the obtained fibers have excellent long-term reliability.

According to the configuration of I-(5), as the metal or carbon is arranged between the conductor that is at the interior and on the circumference of the conductive polymer fibers, fiber of still higher conductivity is obtained. Moreover, as the metal or carbon is not exposed on the fiber surface, corrosion and degradation of the metal or carbon is prevented.

According to the configuration of I-(6), the conductor coats the circumference of the base material, with the result that the conductivity of the conductive polymer fiber is further enhanced, and conduction by contact with multiple conductive polymer fibers is further facilitated.

According to the configuration of I-(7), as the conductive polymer fibers are protected by an insulating layer, fiber of excellent durability is obtained.

According to the biological electrode of I-(8), conductive polymer fibers are provided that have excellent conductivity, and strength in dry and wet states, as well as excellent flexibility, with the result that there is a high degree of freedom of attachment sites on the surface of a living body or within it, workability during attachment operations is excellent, electrical measurement can be adequately conducted, and measurement can also be conducted over a relatively long period of time.

(Effects of Second Aspect)

According to the second aspect of the present invention, the following effects can be obtained.

According to the second aspect of the present invention, and according to the method of production of conductive polymer fibers of the present invention, as stated above, a method is adopted wherein base fibers impregnated with and/or adhering to a conductor containing PEDOT-PSS are energized by passing along a single electrode or between multiple electrodes while being perpendicularly raised from a conductor solution. By this means, productivity is improved, because the process of electrochemically polymerizing and fixing the conductor to the base fibers can be continuously conducted in a one-step process. Furthermore, by having the base fibers travel between electrodes while being perpendicularly raised, the conductor that is polymerized and fixed to the base fibers is uniformly diffused, enabling prevention of irregularities. It is therefore possible to produce with satisfactory productivity a conductive polymer fiber that is endowed with a high degree of biocompatibility and satisfactory uniformity, and that has excellent conductivity and durability.

Moreover, according to the device for producing conductive polymer fibers of the second aspect of the present invention, a configuration is adopted which is provided with a reel unit that perpendicularly raises base fibers impregnated with and/or adhering to a conductor containing PEDOT-PSS from a conductor solution in an immersion container, and a single electrode or multiple electrodes which energize(s) the base fibers while they travel. By this means, as stated above, the process which electrochemically polymerizes and fixes the conductor to the base fibers can be continuously conducted in a one-step process, thereby enabling improvement of productivity. Furthermore, by providing electrodes that energize the base fibers while they are being perpendicularly raised, the conductor that is polymerized and fixed to the base fibers is uniformly diffused, enabling prevention of irregularities. It is therefore possible to obtain with high productivity a conductive polymer fiber that is endowed with a high degree of biocompatibility and satisfactory uniformity, and that has excellent conductivity and durability.

When explained with greater specificity, the following effects can be obtained.

According to II-(1) to (8) of the second aspect, the following effects are obtainable.

According to the method for producing conductive polymer fibers configured as in II-(1), a method is adopted wherein base fibers that are impregnated with and/or adhere to a conductor containing PEDOT-PSS are energized by traveling between electrodes while being perpendicularly raised from a conductor solution, thereby electrochemically polymerizing and fixing the conductor to the base fibers.

Furthermore, according to this configuration, by having the base fibers travel between electrodes while being perpendicularly raised, the conductor that is polymerized and fixed to the base fibers is uniformly diffused, enabling prevention of irregularities, with the result that a conductive polymer fiber of excellent conductivity and durability is obtained.

In the case of II-(2), productivity is improved, because the process of electrochemically polymerizing and fixing the conductor to the base fibers can be continuously conducted in a one-step process.

Moreover, according to this configuration, comb teeth-like electrodes are used which have comb teeth that are multiply provided in the lengthwise direction of the base fibers, and the multiple comb teeth are disposed so as to combine in a respectively alternating manner in the lengthwise direction of the base fibers, from the both sides of the radial direction of the base fibers, with the result that it is possible to raise the efficiency of polymerization and fixation of the conductor to the base fibers by energizing the base fibers by repetitive contact with the multiple comb teeth.

According to the configuration of II-(4), a method is adopted wherein the base fibers are energized by traveling between the respective multiple electrodes while the aforementioned roller-like rotor electrodes are pressed against the base fibers, and hollows formed in pulley-like rotor electrodes provide guidance, thereby alleviating the friction associated with contact of the base fibers and the electrodes, and enabling prevention of peeling of the conductor that is fixed to the base fibers. Moreover, polymerization and fixation can be carried out with retention of a desired amount of PEDOT-PSS by conducting energization while controlling the amount of conductor that impregnates and/or adheres to the base fibers by ordering an arrangement of a fiber bundle.

According to the device for producing conductive polymer fiber of II-(5), the configuration is provided with a reel unit which perpendicularly raises base fibers that are impregnated with and/or adhere to a conductor containing PEDOT-PSS from a conductor solution in an immersion container, and an electrode which energizes the base fibers during travel, thereby electrochemically polymerizing and fixing the conductor to the base fibers. Furthermore, according to this configuration, as the conductor that is polymerized and fixed to the base fibers can be uniformly diffused to prevent irregularities by providing an electrode that conducts energization while the base fibers are being perpendicularly raised, it is possible to produce conductive polymer fiber that has excellent conductivity and durability. With respect to the aforementioned electrode in the device for producing conductive polymer fiber of the present invention, not only may a single electrode be used, but it is also possible to have a configuration that arranges multiple electrodes. In this case, productivity is improved, because the electrochemical polymerization and fixation of the conductor to the base fibers can be continuously conducted in one step.

According to the configuration of II-(6), as the configuration is such that comb teeth-like electrodes are provided as the multiple electrodes, and multiple comb teeth are disposed so as to combine in a respectively alternating manner in the lengthwise direction of the base fibers from the both sides of the radial direction of the base fibers, it is possible to raise the polymerization and fixation efficiency of the conductor relative to the base fibers by energizing the base fibers by repetitive contact with the multiple comb teeth.

According to the configuration of II-(8), as the multiple electrodes are configured from roller-like rotor electrodes disposed on one side in the radial direction of the base fibers, and pulley-like rotor electrodes disposed on the other side, the base fibers are energized by traveling between the respective multiple electrodes while the roller-like rotor electrodes press against the base fiber, and hollows formed in the pulley-like rotor electrodes provide guidance, thereby alleviating the friction associated with contact between the base fibers and the electrodes, and enabling prevention of peeling of the conductor that is fixed to the base fiber. Moreover, polymerization and fixation can be conducted with retention of a desired amount of PEDOT-PSS by conducting energization while controlling the amount of conductor that impregnates and/or adheres to the base fibers by ordering an arrangement of a thread-like fiber bundle with the aforementioned rotor electrodes.

(Effects of the Third Aspect)

According to the third aspect of the present invention, the following effects are obtainable.

The aforementioned biological electrode of the body surface attachment type of the third aspect of the present invention is provided with composite fibers that combine conductive polymer and flexible fiber material. Consequently, attachability relative to the surface of a living body is improved compared to before, and it is possible to downsize the electrode, and reduce the contact area of the skin. Moreover, as the biological electrode of the present invention is configured with flexible fiber material, little irritation is imparted to skin upon attachment, inhibiting occurrence of discomfort during attachment. Furthermore, as the composite fibers configuring the biological electrode of the present invention are suitably adsorbent relative to skin, there is no need to bring about close adhesion of skin and electrode by highly adhesive gel or tape or the like, as with conventional biological electrodes. That is, according to the biological electrode of the present invention, the burden on the subject (the person to whom it is attached) can be alleviated, providing a comfortable wear feeling.

When described with greater specificity, the following effects are obtainable.

The biological electrode and device of the aforementioned third aspect can provide the following effects.

The biological electrode of III-(1) uses conductive composite fibers that have conductivity, flexibility, and excellent tensile strength. Consequently, compared to conventional biological electrodes, there is little discomfort or damage to the wearer when it is attached, electrode resistance per unit area is low, precise transmission of biological signals is possible, and it is also amenable to size and weight reduction.

With respect to III-(2), as the form of the aforementioned contacts is suited to contact with skin or the surface of a living body, a more precise transmission of biological signals is possible, and discomfort or damage to the wearer is further mitigated.

With respect to III-(3), the aforementioned biological electrode is provided with contacts having the aforementioned configuration, thereby raising the structural strength of the aforementioned contacts and the biological electrode, and enabling further reduction of electrode resistance.

With respect to III-(4), the aforementioned conductive composite fibers are adsorbent and hydrophilic relative to skin, thereby enabling the biological electrode to be independently placed on a skin surface or surface of a living body, and further facilitating highly accurate transmission of biological signals with reduced noise. Moreover, according to the biological electrode, attachment can be conducted without using the adhesive and conductive paste or gel that is necessary to attach conventional biological electrodes to skin surfaces.

According to the biological electrode of III-(5), the biological electrode can be inserted between head hair, and the electrode surface can more easily contact the scalp.

According to the biological electrode of III-(6), the aforementioned contacts can stably contact a skin surface or living body surface over a wide area.

According to the biological electrode of III-(7), as the contacts disposed on the surface of a sheet-like base material can be pressed against a skin surface due to the stretchability of the holder, the contacts can be stably placed. Furthermore, while the holder slides over the rear surface of the sheet-like base material as it maintains this stable condition, the holder is capable of moving independently of the sheet-like base material, enabling variation in the relative positions of the holder and the skin surface. Consequently, biological signals can be stably transmitted even in the case where the wearer of the biological electrode moves his/her body.

With respect to III-(8), as the device for measuring biological signals, one may cite, for example, electrocardiographic measurement devices, pulse rate meters, electroencephalographic measurement devices, and so on. With respect to the devices for measuring biological signals, the biological electrode may not only have a function that receives signals from a biological surface, but also a function that transmits electrical signals (electrical stimuli).

It is preferable that apertures be provided in the sheet-like base material of III-(6) and (7), and in the sheet-like base material with which the biological electrode configuring the biological signal measurement device of III-(8) may be provided. Provision of apertures improves aeration between the sheet-like base material and the skin, enabling mitigation of skin steaming.

(Effects of the Fourth Aspect)

According to the fourth aspect of the present invention, the following effects can be obtained.

According to the implantable electrode of the aforementioned fourth aspect of the present invention, as the conductive composite fibers configuring the electrode are flexible, and have excellent biocompatibility, it is possible to reduce invasiveness with respect to biological tissue that is implanted. Moreover, as the conductive polymer contained in the conductive composite fibers can detect weak electrical signals from within a living body, highly accurate transmission and receipt of signals can be conducted between an external device and an electrode implant.

Furthermore, as mechanical strength is increased by the fiber material composing the conductive composite fibers, the electrode is not damaged by external force during implantation, and has excellent durability after implantation.

As the aforementioned implantable electrode with which the device for measuring biological signals of the present invention is provided has a low degree of invasiveness relative to biological tissue, highly accurate transmission and receipt of signals can be conducted between the electrode implant and an externally situated measurement device without impairing the essential functions of the biological tissue.

When explained with greater specificity, the following effects are obtainable.

According to the electrode and device of the aforementioned fourth aspect, the following effects can be obtained.

According to the implantable electrode of IV-(1), as the conductive composite fibers composing the electrode have excellent flexibility and biocompatibility, it is possible to reduce invasiveness with respect to biological tissue that is implanted. In addition, as the conductive polymer contained in the conductive composite fibers can transmit weak electrical signals from within a living body, highly accurate transmission and receipt of signals can be conducted between an electrode implant and an external device. Furthermore, as mechanical strength is increased by the fiber material composing the conductive composite fibers, the electrode is not damaged by external force during implantation, and has excellent durability after implantation.

According to IV-(2), as conductive composite fibers molded into a rod shape can be inserted like a needle during implantation, invasiveness relative to biological tissue can be further reduced. Conductive composite fibers molded into a coil shape (helical shape) almost never cause positional deviation within biological tissue that is implanted, and enable highly accurate transmission and receipt of signals between an electrode implant and an external device.

According to IV-(3), by a simple operation wherein the aforementioned needle which has the aforementioned conductive composite fibers attached to its distal end inserts (is inserted) into biological tissue, the aforementioned conductive composite fibers can be easily placed within biological tissue with little invasiveness. Moreover, by a simple operation wherein the needle is withdrawn while the implanted conductive composite fibers remain within the body, the needle which is unnecessary for receipt and transmission of signals is removed easily from the body, enabling completion of placement of the conductive composite fibers with little invasiveness.

According to IV-(4), when the needle is inserted into biological tissue, the adhesive material is dissolved by absorption of moisture such as body fluid, enabling easy dissolution of the adhesion between the needle and the conductive composite fibers. After dissolution of the adhesion, the needle can be withdrawn from the living body, and the conductive composite fibers can remain within the biological tissue.

According to IV-(5), as conductive fibers in a dry contracted state have relatively high mechanical strength even while being flexible, it is possible to prevent breakage (fracture) of the conductive fibers when they are placed in (inserted into) biological tissue. Moreover, as the physical volume of conductive fibers in a dry contracted state is relatively small, invasiveness during placement in (insertion into) biological tissue can be reduced.

According to IV-(6), by means of the electric wire, an external device can be electrically connected to the conductive composite fibers that are implanted in biological tissue.

According to IV-(7), one end of the core part is connected to a reservoir or a chamber provided with a tube connector in which a drug solution or the like is stored, and the other end of the core part is placed at a specified position in biological tissue, whereby the drug solution or the like penetrates (permeates) the conductive composite fiber composing the core part, enabling transport of the drug solution to the interior of the biological tissue where the other end is placed.

According to IV-(8), the drug (pharmaceutical agent) can be administered to the site where the electrode is implanted via the flow path. The drug is preferably a drug having pharmacological action that inhibits or promotes biological reactions. As the aforementioned drug, one may cite, for example, a drug which reduces damage to biological tissue, a drug which promotes repair of biological tissue, a drug which causes growth of biological tissue, and so on.

According to IV-(9), as the invasiveness of the implantable electrode relative to biological tissue is low, signal transmission and receipt can be conducted with a high degree of accuracy between an electrode implant and an externally situated measurement device without impairing the essential functions of the biological tissue.

Otherwise, in addition to monofilament fibers, the base fibers described in the present invention also include, for example, twist yarns of a desired thickness obtained by intertwining multiple base fibers. The form of the base fiber of the present invention is not limited to the aforementioned thread form, and also includes, for example, forms that are cord-like, cloth-like, ribbon-like, and so on.

BRIEF DESCRIPTION OF THE DRAWINGS

FIG. 21A is a schematic view which shows an example of a cross-sectional structure of a contact, wherein the left portion shows a cross-section along line X-X of the right portion.

FIG. 21B is a schematic view which shows a cross-sectional structure of a contact 321 of a second embodiment of the third aspect, wherein the left portion shows a cross-section of line X-X of the right portion.

FIG. 23A is a graph which shows human brain waves (C3, C4, 50 $\mu$V, 400 msec/div) measured by a hairpin-like electrode for brainwave use.

BEST MODE FOR CARRYING OUT THE INVENTION

Preferred examples and embodiments of the present invention pertaining to the first to the fourth aspects of the present invention are described below with use of drawings. However, the present invention is not limited by any of the following examples and embodiments. For example, components and conditions of these preferred examples and embodiments may be appropriately combined. Moreover, preferred examples may be used interchangeably among the respective aspects, and other components may be combined to an extent that is not problematic. Modification of positions, quantities, sizes, amounts, and the like are possible within a scope that does not deviate from the intent of the present invention.

Figure 1:
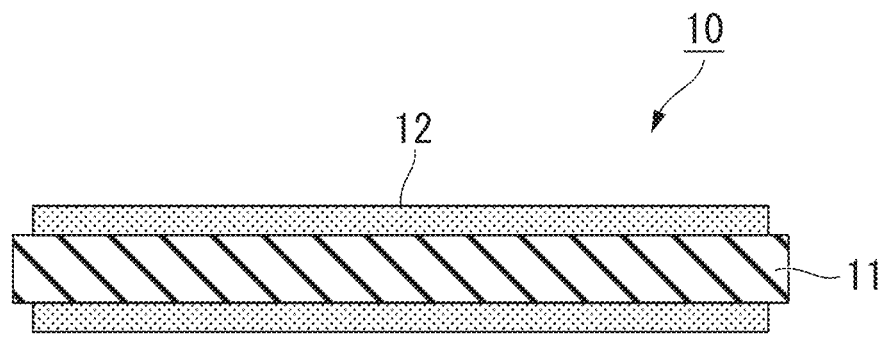
FIG. 1 is a schematic view which shows a lengthwise cross-section in an example of a conductive polymer fiber of the present invention.

For example, the preferred example given in the description of FIG. 1 may also be preferentially used in other examples of this aspect, unless otherwise specified.

Regarding the First Aspect

A first embodiment of the first aspect of the present invention is described below with reference to drawings, but the present invention is not limited by the pertinent embodiment.

The first embodiment of the first aspect of the present invention relates to a conductive polymer fiber, and a biological electrode. More specifically, it relates to a conductive polymer fiber in which a conductive polymer impregnates or adheres to a base fiber, and to a biological electrode provided with the aforementioned conductive polymer fiber.

First Embodiment of First Aspect

Figure 3:
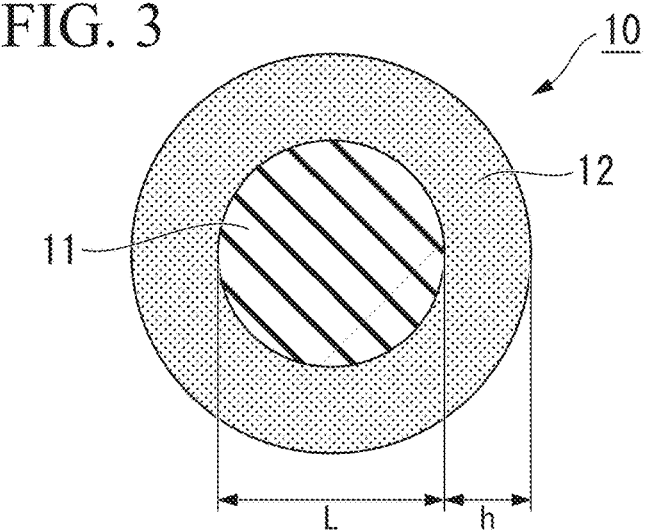
FIG. 3 is a schematic view which shows a cross-section in a direction that is orthogonal to the lengthwise direction in an example of the conductive polymer fiber of the present invention.

A conductive polymer fiber 10 of the present invention shown in FIG. 1 (first embodiment) is a fiber wherein a base fiber 11 is coated with a conductor 12 containing PEDOT-PSS {poly(3,4-ethylenedioxythiophene)-poly(styrene sulfonic acid)} as conductive polymer. FIG. 1 is a cross-sectional view in the lengthwise direction of the conductive polymer fiber 10, and FIG. 3 is a cross-sectional view in a direction orthogonal to the lengthwise direction. As the base fiber 11 is used as the core of the conductive polymer fiber 10, and as its circumference is coated with the conductor 12, the adhesive area of the two is large, constituting a composite fiber with sufficient mutual adhesion. When this configuration exists, the conductor 12 is reinforced by the base fiber 11, with the result that strength can be increased compared to fiber that consists only of the conductor 12. In particular, strength in wet and dry states is excellent. Moreover, the flexibility of the base fiber 11 at the core is imparted to the conductive polymer fiber 10.

There are no particular limitations on the type of the base fiber 11, provided that it is composed of a polymer. For example, one may use synthetic fiber, vegetal fiber, animal fiber, and the like. It may consist of a single material, or a mixed material.

As the aforementioned synthetic fiber, one may cite, for example, nylon, polyester, acrylic, aramid, polyurethane, carbon fiber, and so on. As the aforementioned vegetal fiber, one may cite, for example, cotton, hemp, jute, and so on. As the aforementioned animal fiber, one may cite, for example, silk, wool, collagen, elastic fiber composed of animal tissue, and so on.

Among the enumerated base fiber materials, it is preferable to use animal-based fiber (protein-containing fiber), which has excellent adhesivity with the conductor 12, high strength in dry and wet states, and flexibility appropriate for applications to clothing and the like. Furthermore, silk fiber is more preferable, because it has particularly excellent adhesivity and hydrophilicity relative to the below-mentioned PEDOT-PSS.

The base fiber preferably consists of silk alone, but mixed material is also preferable if necessary. In the case of a silk mixture, the silk content may be from 0.1% to less than 100%, or from 1% to 95%, or from 3% to 90%, or from 10% to 80%, or from 30% to 70%, or from 40% to 60%. It is preferable to suitably mix it with other material according to the intended use.

As silk fiber that may be used with the base fiber 11, one may cite, for example, natural silk fiber of silkworms, spiders, and bees, as well as artificial silk fiber using gene recombination technology. Silk contains protein referred to as fibroin, and is fiber that has excellent hydrophilicity, biocompatibility, and stainability, as when used in clothing and surgical thread, and is one of the fibers that has been used by humanity since ancient times. Consequently, it may be optimally used as the base fiber 11.

The silk fiber used in the base fiber 11 may be either unprocessed raw silk from which the sericin that is the gelatinous component has not been removed, or refined silk from which the sericin has been partially or fully removed. Refined silk is preferable from the standpoint of raising adhesivity with the conductor 12, and fiber strength.

There are no particular limitations on the diameter (thickness) of the base fiber 11, and it may be suitably selected according to application. As examples of diameter, one may cite, for instance, ranges of 0.1 µm to 1 mm, 1 µm to 1 mm, 1 µm to 0.5 mm, and so on. For example, a diameter of 1 µm to 100 µm is preferable when used in clothing, biological electrodes, biointerfaces, and the like.

There are no particular limitations on the length of the base fiber 11, and it may be suitably selected according to application. For example, one may set a length of 10 µm to 10 cm as an electrode for implantation into biological tissue, 1 mm to 50 cm for use in a biointerface on a body surface, 1 cm to 100 m as fiber material to be woven or knitted into an article of clothing, and so on, but one is not limited thereto, and the selection may be made according to necessity.

There are no particular limitations on the base fiber 11 (41), and it may be selected according to necessity. For example, one may use twisted filament of a desired thickness obtained by twisting together multiple base fibers (see the example shown in FIG. 6), and blended yarn that blends different types of base fiber. The form of the base fiber is not limited to the aforementioned thread form, and one may also use without problem a base fiber that is cord-like, cloth-like, ribbon-like, and so on. For purposes of enhancing the hydrophilicity of the base fiber 11, it is also acceptable to use a base fiber that has been subjected to plasma treatment, pore treatment, or chemical coating.

The conductor 12 includes conductive polymer, and may be composed only of conductive polymer, or may also include other additives.

The conductive polymer used in the present invention is PEDOT-PSS {poly(3,4-ethylenedioxythiophene)-poly(styrene sulfonic acid)} which has excellent conductivity and hydrophilicity. PEDOT-PSS is a conductive polymer which can be obtained by polymerizing 3,4-ethylenedioxythiophene, which is a monomer, in the presence of poly(4-styrene sulfonic acid)}. PPS functions as a dopant that imparts a negative charge to PEDOT. In the present invention, it is preferable to include a dopant in the conductive polymer from the standpoint of raising the conductivity of the conductive polymer fiber.

The present inventors discovered that the adhesivity of PEDOT-PSS and fiber containing protein such as silk is particularly excellent, and that the adhering surfaces of the two do not easily come apart. Based on this finding, in the present invention, it is more preferable to use silk fiber as the base fiber 11, and PEDOT-PSS as the conductive polymer containing the conductor 12.

As other conductive polymers that may be used, polyaniline sulfonic acid and polypyrrole can be cited. With respect to the conductive polymer containing the conductor 12, one type may be used, or two or more types may be used in combination.

There are no particular limitations on the molecular weight of the conductive polymer used in the present invention. For example, molecular weights in a range from several thousand to several tens of thousand may be used, and may be optionally selected according to necessity. To cite specific examples, polystyrene-converted weight average molecular weight (Mw) may be in a range of 1000-900000, a range of 3000-450000, or a range of 5000-50000, but one is not limited to these ranges.

As the method for forming the conductor 12, one may cite a method which forms a conductor 12 composed only of conductive polymer by coating the base fiber 11 with a solvent containing conductive polymer such as PEDOT-PSS and a diluting solvent, and by drying the solvent. However, the conductor 12 may also contain additives other than the conductive polymer.

As the aforementioned additives, one may cite, for example, glycerol, sorbitol, polyethylene glycol-polypropylene glycol copolymer, ethylene glycol, sphingosine, phosphatidylcholine, and so on. One type of additive may be included in the conductor 12, or two of more types may be used in combination.

The above-cited additives may be used for the purpose of adjusting the wetting properties of conductive polymer fiber such as PEDOT-PSS, and for the purpose of improving compatibility with biological tissue (skin or tissue) when used as a biological electrode by imparting flexibility.

Otherwise, as specific examples of the aforementioned adjustment of wetting properties, one may cite, for example, adjustment of water absorbency, prevention of excessive swelling/contraction during wetting/drying, and so on.

It is preferable to use PEDOT-PSS and the aforementioned additives in combination, because adjustment of the wetting properties of the conductor 12 is facilitated, and prevention of excessive swelling and drying is particularly facilitated. As to the reasons for this, it would seem that one factor is that inclusion of additives in advance as well as PEDOT-PSS that has a high degree of water absorbency reduces the scope for subsequent infiltration of moisture.

With respect to additives used for the purpose of adjusting the wetting properties of PEDOT-PSS, and further imparting flexibility, among the foregoing examples, glycerol, sorbitol, polyethylene glycol, and polyethylene glycol-polypropylene glycol copolymer are particularly preferable.

Even when used in a high humidity environment, the conductive polymer fiber 10 having the conductor 12 containing the aforementioned additives and PEDOT-PSS does not exhibit excessive moisture absorption, and has a high degree of fiber strength, and excellent conductivity. As it also combines excellent flexibility, the rough feel (rigidity) of PEDOT-PSS is moderated, and as it has excellent tactility and compatibility with biological tissue, it can compose biological electrodes that are capable of low-noise measurement of biological signals.

As additives contained in the conductor 12, one is not limited to the foregoing examples. For example, one may also use known organic solvents such as surface active agents, alcohols, natural polysaccharides, sugar alcohols, acrylic resins, and dimethyl sulfoxide.

As the aforementioned surface active agents, one may cite known cationic surface active agents, anionic surface active agents, and non-ionic surface active agents. These surface active agents may be used alone or in combinations of two or more.

As the aforementioned cationic surface active agents, one may cite, for example, quaternary alkyl ammonium salt, halogenated alkylpyridinium, and so on.

As the aforementioned anionic surface active agents, one may cite, for example, alkyl sulfate, alkylbenzene sulfonate, alkyl sulfosuccinate, fatty acid salt, and so on.

As the aforementioned non-ionic surface active agents, one may cite, for example, polyoxyethylene, polyoxyethylene alkyl ether, and so on.

As the aforementioned alcohols, one may widely use known monovalent alcohols and polyvalent alcohols. With respect to these alcohols, one type may be used alone, or two or more types may be used in combination.

As monovalent alcohols, one may cite, for example, methanol, ethanol, propyl alcohol, isopropyl alcohol, butanol, and so on. The carbon skeleton composing these alcohols may be straight-chained, branched, or cyclic.

As polyvalent alcohols, one may cite, for example, glycols such as ethylene glycol; chain polyvalent alcohols such as glycerin; cyclic polyvalent alcohols such as glucose and sucrose; polymer polyvalent alcohols such as polyethylene glycol or polyvinyl alcohol, and polyethylene glycol-polypropylene glycol copolymer; and so on.

As natural polysaccharides, one may cite, for example, chitosan, chitin, glucose, aminoglycan, and so on.

As sugar alcohols, one may cite, for example, sorbitol, xylitol, erythritol, and so on.

As the aforementioned acrylic resin, one may cite, for example, polyacrylic acid, polymethyl methacrylate, methyl polymethacrylate resin, and so on.

There are no particular limitations on a thickness h of the conductor 12 that coats the circumference of the base fiber 11, and it may be selected at one's discretion. Any thickness is acceptable, provided that the effects of the present patent application are obtained. For example, thickness may be 0.001 to 2-fold a diameter L of the base fiber 11. The thickness h may be selected according to necessity, and, for example, it is acceptable to have a thickness that is 0.01 to 1-fold, a thickness that is 0.001 to 0.1-fold, a thickness that is 1 to 2-fold, or a thickness that is 0.1 to 1-fold the diameter L of the base fiber 11. More specifically, for example, in the case where silk fiber of silkworms of 2-3 denier (D)—i.e., silk fiber with a fiber diameter of approximately 10-15 microns—is used as the core, a thickness of 0.01-10 microns is acceptable. Fiber diameter and the like may be measured by an optional method, and can be confirmed by such means as electron microscope photographs.

If necessary, a less-than-complete coating of the base fiber with the conductor is also acceptable. In the present invention, the thickness may mean the length of a line which starts from a center of the base fiber to a surface and an end thereof is covered by the conductor.

By coating the circumference of the base fiber 11 with the conductor 12, the conductivity of the conductive polymer fiber 10 is raised, and conduction by contact of multiple conductive polymer fibers 10 is facilitated. Moreover, with the aforementioned thickness range, it is possible to obtain a fiber having more excellent conductivity without impairing the flexibility of the conductive polymer fiber 10. Within the aforementioned range, the greater is the thickness, the higher is the conductivity of the fiber that can be obtained. In short, the conductivity or electrical resistance of the conductive polymer fiber 10 can be adjusted by adjusting the thickness of the conductor 12.

\<Conductive Polymer Fiber Production Method (1a)\>

The following method may be cited as an exemplary method for coating the surface of the base fiber 11 with the conductor 12 or causing adhesion of the conductor 12 to form the conductive polymer fiber 10 shown in FIG. 1.

First, an aqueous solution containing conductive polymer (e.g., a commercial PEDOT-PSS solution (Heraeus, Ltd.: CLEVIOS P)) is made to adhere to the surface of the base fiber 11 in a solution bath. Thereafter, or after uniformly applying the aforementioned solution to the surface of the base fiber 11 using a roller or a brush, a portion of the moisture contained in the aforementioned solution is removed by drying. Subsequently, an organic solvent such as acetone, methanol, ethanol or the like, or a fixing solution such as magnesium chloride solution is applied to gelatinize the conductive polymer of PEDOT-PSS or the like. By this means, a method which fixes the conductor 12 containing conductive polymer such as PEDOT-PSS to the surface of the base fiber 11 (hereinafter referred to as "production method 1a") can be exemplified. As an example of the aforementioned aqueous solution, one may cite an aqueous solution containing conductive polymer of PEDOT-PSS or the like at a concentration of 0.1-50 (v/v) %. This concentration may be selected as necessary. For example, a concentration such as 1-30%, 30-50%, or 0.5-15% is also acceptable. Otherwise, the aforementioned aqueous solution may contain the aforementioned additives as necessary.

In the present invention, as an aqueous solution containing conductive polymer, apart from the cited CLEVIOS P, any solution containing PEDOT-PSS can be used.

\<Method for Causing Inclusion of Additives\>

As a method for causing inclusion of additives in the conductor 12, one may cite a method wherein the conductor 12 that was applied to the base fiber 11 by production method 1a is dried, after which the additive is applied to the surface of the obtained conductive polymer fiber 10, or a method wherein a conductive polymer fiber 10 is immersed in a solution containing the additive for a prescribed time, after which the excess additive solution remaining on the surface is removed. As another method, one may use a mixed solution obtained by mixing the additive in the solution containing the conductive polymer that is used to be coated onto the surface of the base fiber 11, and together apply the conductive polymer and additive, or perform immersion therein.

As an example of the aforementioned mixed solution, one may cite an aqueous solution containing a conductive polymer such as PEDOT-PSS at a concentration of 0.1-50 (v/v) %, and an additive such as glycerol at a concentration of 0.1-50 (v/v) %.

There are no particular limitations on the concentration of the additive in the conductor 12 in the present invention, and it may be set at, for example 0.1-50 wt %. This concentration may be selected as necessary, and, for example, 1-20 wt %, 20-50 wt %, or 0.1-5 wt % is also acceptable.

Second Embodiment of First Aspect

Figure 2:
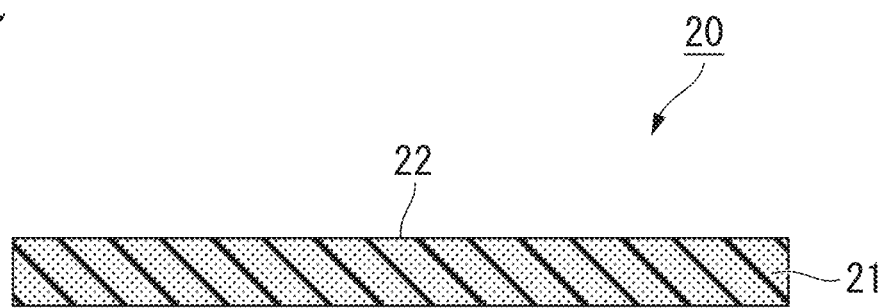
FIG. 2 is a schematic view which shows a lengthwise cross-section in an example of the conductive polymer fiber of the present invention.
Figure 4:
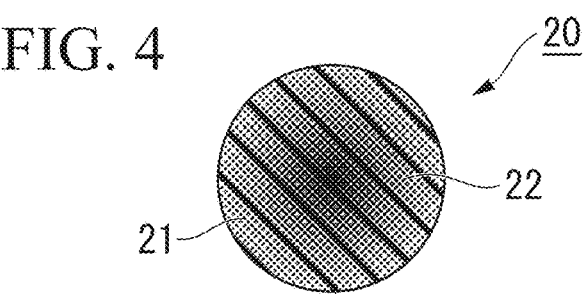
FIG. 4 is a schematic view which shows a cross-section in a direction that is orthogonal to the lengthwise direction in an example of the conductive polymer fiber of the present invention.

A conductive polymer fiber 20 of the present invention shown in FIG. 2 (second embodiment) is fiber in which a base fiber 21 is impregnated with a conductor 22 containing conductive polymer. FIG. 2 is a cross-sectional view in the lengthwise direction of the conductive polymer fiber 20, and FIG. 4 is a cross-sectional view in a direction orthogonal to the lengthwise direction.

As the conductor 22 permeates the interior of the base fiber 21, the two constitute an integrated composite fiber.

When this configuration exists, there is no risk that the conductor 22 may come apart from the base fiber 21. Moreover, as the conductor 22 is reinforced by the base fiber 21, strength can be increased compared to fiber composed of the conductor 22 alone, and it also endowed with the flexibility of the base fiber 21.

Otherwise, in the present invention, the entirety of the internal space of the base fiber may be filled by the conductor, but it is also acceptable if there is unfilled space. The conductor preferably reaches to the center of the interior of the base fiber, but there may also be portions where it does not reach there as necessary.

With respect to the materials composing the base fiber 21 and the conductor 22, the materials composing the base fiber 11 and the conductor 12 described in the first embodiment may be applied. As with the first embodiment, the conductor 22 preferably contains the aforementioned additives.

<Conductive Polymer Fiber Production Method (1b)>

As with the conductive polymer fiber 20 shown in FIG. 2, as a method of immersing the conductor 22 in the base fiber 21, an aqueous solution containing conductive polymer (e.g., a commercial PEDOT-PSS solution (Heraeus CLEVIOS P)) is immersed in the base fiber 21 for a prescribed time in a solution bath, after which a portion of the moisture contained in the aforementioned solution is removed by driving, and then an organic solvent such as acetone, methanol, ethanol or the like, or a fixing solution such as magnesium chloride solution is applied to gelatinize the PEDOT-PSS. By this means, a method which fixes the conductor 22 containing PEDOT-PSS to the surface of the base fiber 21 can be exemplified (hereinafter referred to as "production method 1b").

Otherwise, the aforementioned aqueous solution may contain the aforementioned additives as necessary.

As a method for accelerating permeation of a solution containing a conductive polymer in the base fiber 21, one may cite a method which conducts immersion with adjustment of the pH of the aforementioned solution, a method which subjects the base fiber 21 to mechanical operations such as tension or compression or the like during immersion, a method which heats the aforementioned solution during immersion, a method which conducts treatment such as pressure reduction or pressure application during immersion, and so on. Specifically, in the case where the base fiber 21 of silk or the like is immersed in a PEDOT-PSS solution, the pH of the aforementioned solution is preferably adjusted from 1-6.

Third Embodiment of the First Aspect

Figure 5:
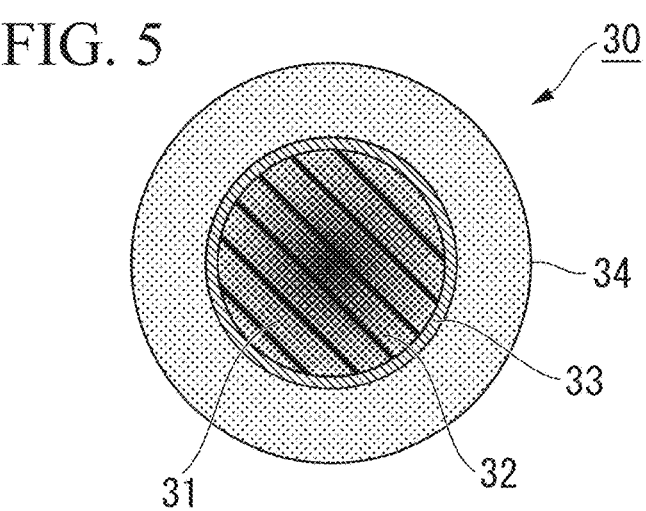
FIG. 5 is a schematic view which shows a cross-section in a direction that is orthogonal to the lengthwise direction in an example of the conductive polymer fiber of the present invention.

With respect to a conductive polymer fiber 30 of the present invention shown in FIG. 5 (third embodiment), a base fiber 31 is impregnated with a conductor 32 containing conductive polymer, the circumference of the base fiber 31 is coated with a metal 33, and the circumference of the coated metal or carbon 33 is also coated with a conductor 34. FIG. 5 is a cross-sectional view in a direction orthogonal to the lengthwise direction of the conductive polymer fiber 30.

Unless otherwise specified, "metal or carbon" is referred to below as "metal."

The third embodiment combines the above-described advantages of the first embodiment and the second embodiment. In addition, the coated metal 33 itself contributes to improving the conductivity of the conductive polymer fiber 30. As the metal 33 is interposed between the conductor 32 and the conductor 34, the metal 33 is not exposed on the fiber surface, thereby preventing corrosion or deterioration of the metal 33. It is also acceptable to have a portion of the metal 33 exposed on the fiber surface as necessary.

The materials composing the base fiber 31 and the conductors 32 and 34 may apply the materials composing the base fibers and the conductors described in the first embodiment and the second embodiment. As in the first embodiment and the second embodiment, the conductors 32 and 34 preferably contain the aforementioned additives. The material composing the conductor 32 and the material composing the conductor 34 may be identical, or may differ.

There are no particular limitations on the type of metal 33, and one may cite, for example, titanium, gold, silver, copper, carbon, and so on. Of these metals, gold is preferable due to its corrosion resistance, conductivity, and ductility.

The aforementioned carbon preferably contains carbon atoms as the primary raw material, and examples of the primary raw material include, for example, carbon black, glassy carbon, graphene, carbon nanotube, and fullerene. The carbon content in these carbon materials is preferably 80-100 mass %, more preferably 90-100 mass %, and still more preferably 95-100 mass %.

The metal 33 may use a single type of metal, or it may use two or more types of metal in combination.

There are no particular limitations on the thickness of the metal 33 (metal layer or carbon layer) that coats the circumference of the base fiber 31, and it may be suitably changed according to the type of metal. For example, one may cite a range of 0.1 nm to 1 mm. For instance, in the case where gold is used, its thickness may be set at 1 nm to 2 µm. The metal layer 33 may be formed by known film formation method such as the sputtering method or the non-electrolytic plating method. A carbon layer may be formed by a known film formation method such as carbon deposition.

<Conductive Polymer Fiber Production Method (2a)>

The following method may be cited as a method for producing the conductive polymer fiber 30.

First, by means of a known film formation method, the metal 33 is coated onto the conductive polymer fiber 20 obtained by production method 1b. The fiber obtained thereby is immersed in an aqueous solution containing conductive polymer (e.g., a commercial PEDOT-PSS solution (Heraeus CLEVIOS P)), and a direct current voltage of +0.5 V to 20 V is applied using this metal 33 as an electrode, thereby electrochemically fixing the conductive polymer of PEDOT-PSS or the like to the surface of the metal 33 to produce the conductive polymer fiber 30. This method is hereinafter referred to as production method 2a.

In this instance, a method which forms the metal layer over the circumference of the conductive polymer fiber 20 is exemplified, but it is also acceptable to adopt a method wherein a metal layer is simply formed on a base fiber, and a conductive polymer is similarly electrically fixed to the circumference of the aforementioned metal layer.

Here, the conductive polymer fiber 30 is obtained with a more excellent conductivity by adding ethylenedioxythiophene (EDOT) to the aforementioned solution. The amount of ethylenedioxythiophene may be selected at one's discretion. For example, a 0.1 w/v % solution of ethylenedioxythiophene (Heraeus CLEVIOS M V2) or the like may be added to the aforementioned solution.

<Conductive Polymer Fiber Production Method (2b)>

One may also cite a method wherein the conductive polymer is electrochemically fixed without formation of the metal 33. That is, the conductive polymer fiber 20 obtained by production method 1b is already conductive. Utilizing this conductivity, the conductive polymer fiber 20 obtained by production method 1b is added to a solution containing a conductive polymer (e.g., a commercial PEDOT-PSS solution (Heraeus CLEVIOS P)), and a direct current voltage of +0.5 V to 20 V is applied therein, thereby enabling production of conductive polymer fiber wherein the conductive polymer of PEDOT-PSS or the like is electrochemically fixed to the surface of the circumference of the conductive polymer fiber 20. This method is hereinafter referred to as production method 2b. Otherwise, the aforementioned additives may be included in the aforementioned aqueous solution as necessary.

A figure depicting the configuration of the conductive polymer fiber obtained by production method 2b is omitted, but it is a configuration wherein the metal 33 is removed from the conductive polymer fiber 30 shown in FIG. 5, and the aforementioned metal 33 is replaced by the conductor 34.

Fourth Embodiment

Figure 6:
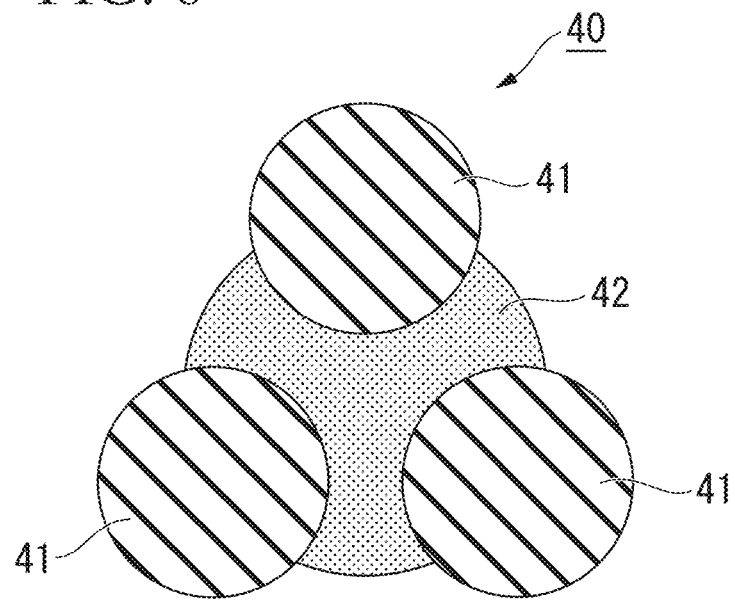
FIG. 6 is a schematic view which shows a cross-section in a direction that is orthogonal to the lengthwise direction in an example of the conductive polymer fiber of the present invention.

With respect to the conductive polymer fiber 40 of the present invention shown in FIG. 6 (fourth embodiment), a conductor 42 containing a conductive polymer is arranged between multiple base fibers 41 with close adhesion to the base fiber 41. FIG. 6 is a cross-sectional drawing in a direction orthogonal to the lengthwise direction of the conductive polymer fiber 40. The number of base fibers may be selected at one's discretion, and is an integer of two or more. For example, a number such as 2, 3, 4, 5, 6, 7, or 8 is acceptable. A number in a range of 1-30, or a number in a range of 1-1000 may be used. The conductive polymer fiber 40 may be formed into a high order structure such as twisted cord, cloth, or nonwoven cloth by intertwining and/or weaving together multiple base fibers 41. As in the example shown in FIG. 6, the conductive polymer fiber 40 may be configured as a high order structure such as twisted cord, cloth, or nonwoven cloth by arranging the conductor 42 containing PEDOT-PSS, which is a conductive polymer, among multiple base fibers 41 with close adhesion to the base fiber, and by intertwining and/or weaving together the multiple base fibers 41.

As the conductor 42 assumes the role of bonding the multiple base fibers 41, the strength of the aforementioned high order structure can be increased. Furthermore, as a relatively large amount of the conductor 42 can be placed among the multiple base fibers 41, a conductive polymer fiber of more excellent conductivity is obtained. The reference amount compared here is the amount of conductor placed on the surface of a single base fiber.

There are no particular limitations on the method for producing the conductive polymer fiber 40. For example, one may cite a method wherein the aforementioned high order structure is immersed in a solution containing conductive polymer, and this is dried.

The fiber interval between the multiple base fibers may be selected at one's discretion. For example, the fiber interval between base fibers 41 may be set at 0.01-3 times the diameter of the base fiber. For example, in the case where a base fiber 41 with a diameter of 10 µm to 15 µm is used, it may be set to 0.01 µm to 50 µm. When the fiber interval is within such a range, a sufficient amount of the conductor 42 can be placed between the fibers.

The materials composing the base fiber 41 and the conductor 42 may apply the materials composing the base fiber and the conductor described in the first embodiment. As in the first embodiment, the conductor 42 preferably contains the aforementioned additives.

Fifth Embodiment of the First Aspect

Figure 7:
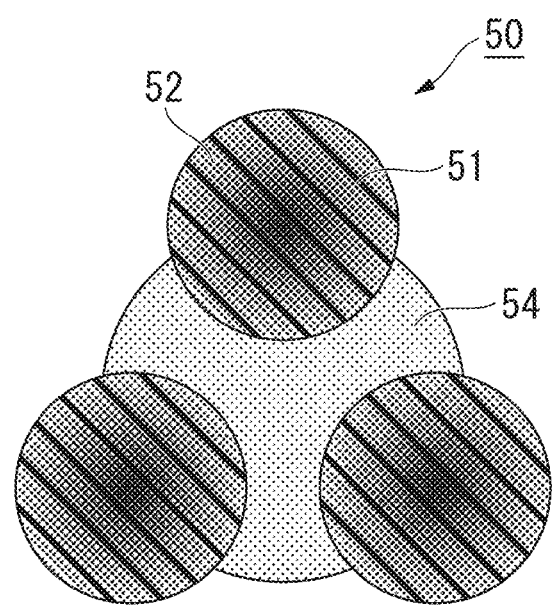
FIG. 7 is a schematic view which shows a cross-section in a direction that is orthogonal to the lengthwise direction in an example of the conductive polymer fiber of the present invention.

A conductive polymer fiber 50 of the present invention shown in FIG. 7 (fifth embodiment) is a fiber wherein a conductor 54 containing conductive polymer is placed between multiple base fibers 51 that are internally impregnated with a conductor 52 containing conductive polymer, and closely adheres to the base fiber 51. FIG. 7 is a cross-sectional view in a direction orthogonal to the lengthwise direction of the conductive polymer fiber 50.

Apart from the internal impregnation of the base fiber 51 with the conductor 52, the configuration of the fifth embodiment is identical to the configuration of the fourth embodiment. In the present embodiment, conductivity is further enhanced by the conductor 52.

The material composing the conductor 52 and the material composing the conductor 54 may be identical, or may differ. The production method of the fifth embodiment may apply the above-described production methods of the first to the fourth embodiments.

Sixth Embodiment of the First Aspect

Figure 8:
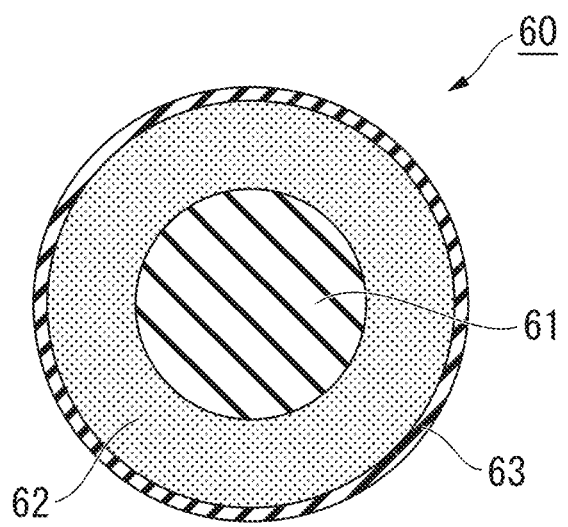
FIG. 8 is a schematic view which shows a cross-section in a direction that is orthogonal to the lengthwise direction in an example of the conductive polymer fiber of the present invention.

A conductive polymer fiber 60 of the present invention shown in FIG. 8 (sixth embodiment) is fiber constituted by coating a base fiber 61 with a conductor 62 containing conductive polymer, and coating the circumference thereof with an insulating layer 63. FIG. 8 is a cross-sectional view in a direction orthogonal to the lengthwise direction of the conductive polymer fiber 60.

As the base fiber 61 and the conductor 62 are protected by the insulating layer 63, fiber of excellent durability is obtained. A configuration may also be adopted as necessary wherein a portion of the insulating layer 63 is removed to expose a portion of the conductor 62 at the surface of the fiber.

Known insulating materials may be applied as the material of the insulating layer 63. From the standpoints of biocompatibility and flexibility, polytetrafluoroethylene (PTFE) and silicone resin (silicone rubber) are preferable. There are no particular limitations on the thickness of the insulating layer 63. It may be selected at one's discretion, and may be set within a range of, for example, 0.1 µm to 3 mm, 0.1 µm to 2 mm, 1 µm to 2000 µm, 10 µm to 500 µm, or the like. The base fiber 61 and the conductor 62 may be coated with the insulating layer 63 by known resin coating methods.

<Biological Electrode>

As the conductive polymer fiber of the present invention has sufficient strength, conductivity, and flexibility even under high-humidity usage conditions, it is not only suitable for use in biological electrodes and biointerfaces, but also in clothing.

By multiply bundling the conductive polymer fiber of the present invention to configure thread or cord, it is possible to obtain conductivity that is sufficient for measurement of biological signals. As PEDOT-PSS which is a conductive polymer is combined with the aforementioned fiber, conduction can be immediately obtained by contact of the aforementioned fiber and a measurement object. Accordingly, biological signals can be stably recorded over a long period by having the aforementioned fiber (thread) contact the measurement object, or by tying it, wrapping it, sewing it, or tucking it thereto/therein.

In the case where a biological electrode is fabricated using the conductive polymer fiber of the present invention as the electrode, it is possible to offer a biological electrode in various forms such as that of a cloth, belt, or strap by tying, weaving, stitching, or bundling thread that bundles the aforementioned fiber. Furthermore, a patch-like (cloth-like) biological electrode can also be produced by combining this conductive polymer fiber, and molding it into nonwoven cloth or the like.

Regarding the Second Aspect

The second aspect of the present invention relates to a method and a device for producing conductive polymer fiber. In particular, it relates to a method and a device for producing conductive polymer fiber wherein a conductor containing conductive polymer impregnates or adheres to an insulating fiber (fiber bundle).

An embodiment of the method and the device for producing conductive polymer fiber of the second aspect of the present invention is described below with appropriate reference mainly to FIG. 13 to FIG. 18, but the second aspect of the present invention is not limited to the below embodiment. Now, FIGS. 13-16 are schematic drawings which show devices for producing conductive polymer fiber described in the present embodiments. FIG. 1, 3, 6, and the like are schematic drawings which show examples of the conductive polymer fiber obtained by the production method and the production device of the present embodiment.

(Conductive Polymer Fiber)

The production method and production device of the second aspect of the present invention are capable of preferentially forming the conductive polymer fiber described in the aforementioned first aspect. The preferred conditions stated in the first aspect can also be used here. For example, the conductive polymer fiber recorded in FIG. 1, 3, or 6 can be easily formed. In the present aspect, it is more preferable to use PEDOT-PSS as the conductive polymer contained in the conductor 12, but the base fiber used in the present embodiments is not limited to silk fiber, and other common fiber materials may be used without any restriction. It is sufficient if incorporation of PEDOT-PSS as the conductive polymer is required.

In the present aspect, when producing the conductive polymer fiber 10 by the production method and production device described below, first, the conductor 12 is made to impregnate and/or adhere to the base fiber 11 by immersing the base fiber 11 in a solution of the conductor 12. At this time, with respect to the solution of the conductor 12, a diluting solvent may be included in addition to the PEDOT-PSS that is the conductive polymer, and additives apart from the conductive polymer may also be included as necessary.

(Method and Device for Producing Conductive Polymer Fiber)

An embodiment of the method and device for producing the conductive polymer fiber of the present invention is described in detail below with reference mainly to FIG. 13-16.

(Production Device)

First, the production device used in the present embodiment is described in detail.

Figure 13:
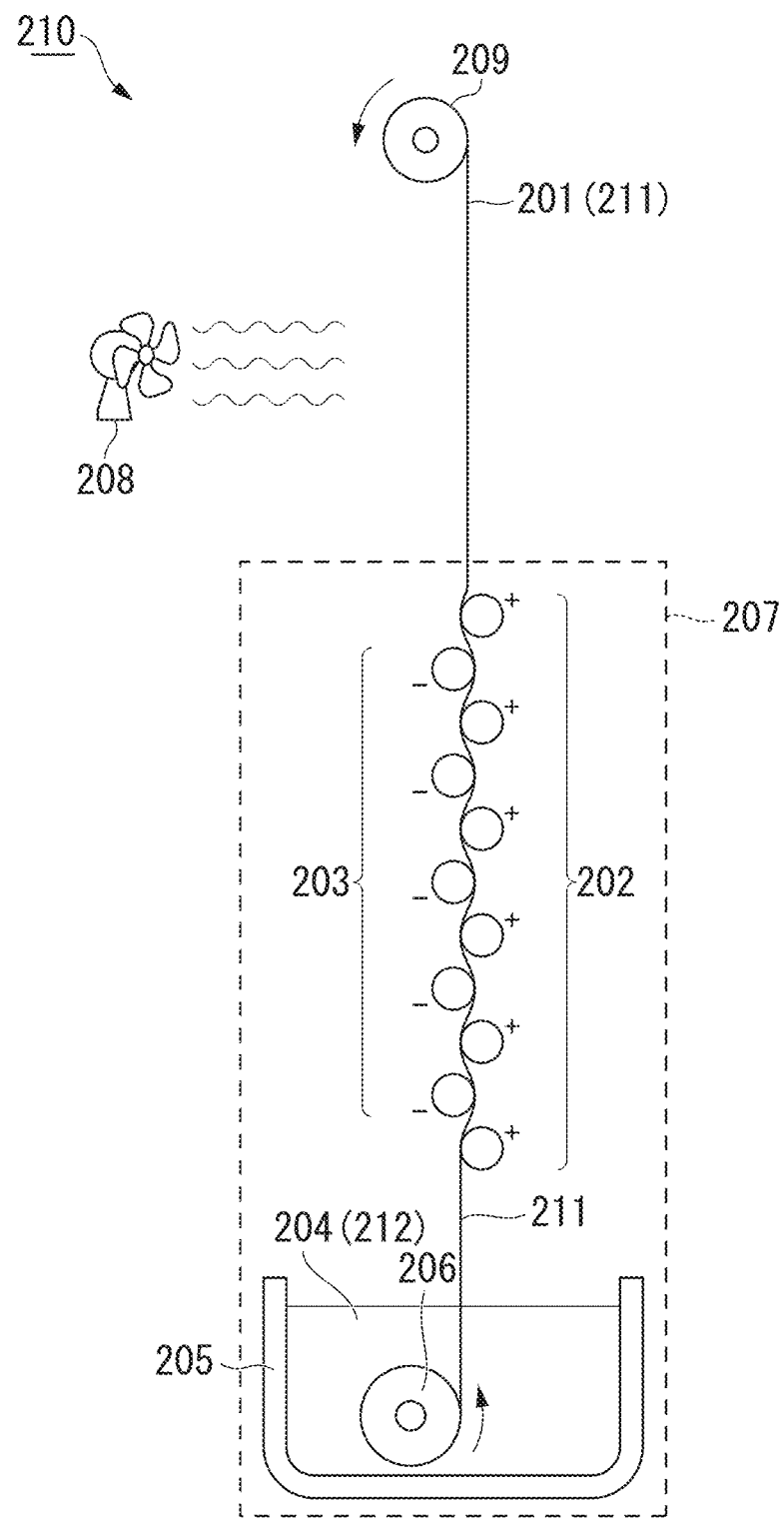
FIG. 13 is a figure which schematically shows an embodiment of a method and a device for producing the conductive polymer fibers of the present invention, and is a schematic diagram which serves to describe an example of configuration of a device for producing conductive polymer fibers.

A device for producing conductive polymer fiber (hereinafter abbreviated as "production device") 210 shown in FIG. 13 is provided with an immersion container 205. The immersion container 205 internally houses a conductor solution 204 that contains PEDOT-PSS {poly(3,4-ethylenedioxythiophene)-poly(styrene sulfonic acid)} as conductive polymer, and is an immersion container which serves to immerse an insulating base fiber 211 composed of thread-like, cord-like, cloth-like, or ribbon-like fiber bundles in the conductor solution 204 to cause a conductor (see a conductor 212 shown in FIG. 17A, 17B, and so on) to impregnate and/or adhere to the base fiber 211. In addition, the production device 210 is provided with a reel unit 209 which serves to perpendicularly raise the base fiber 211 from the conductor solution 204 housed in the immersion container 205, and multiple electrodes 202 and 203 which electrochemically polymerize and fix the conductor 212 that impregnates and/or adheres to the base fiber 211 by energizing the perpendicularly raised base fiber 211 while it travels. The production device 210 described in the present embodiment is also provided with a dryer 208 which conducts drying by blowing air toward the base fiber 211 on/in which the conductor 212 has been polymerized and fixed, and a chamber (including a humidity regulator) 207 capable of adjusting atmospheric humidity in the vicinity of the base fiber 211 to constitute the skeletal framework.

As stated above, the immersion container 205 is a container which internally houses the conductor solution 204 containing PEDOT-PSS as conductive polymer, and may consist of a conventional known container. A bobbin 206 is housed within the immersion container 205 so as to be immersed in the conductor solution 204. The insulating base fiber 211 composed of thread-like, cord-like, cloth-like, or ribbon-like fiber bundles that is wound around the bobbin 206 is immersed in the conductor solution 204, thereby causing the conductor 212 to impregnate and/or adhere to the base fiber 211.

In the present embodiment, a conventional known bobbin may be used as the bobbin 206. For example, a bobbin may be used which is configured in the form of a roll bobbin or the like, and which is capable of being turned by a motor or the like, thereby enabling winding of the base fiber 211. Around this bobbin 206 is wound a base fiber 211 to which the treatment that causes impregnation and/or adhesion of the conductor 212 thereto has not been conducted. The base fiber 211 that is wound around the bobbin 206 is played out, as the post-treated base fiber 211, i.e., a conductive polymer fiber 201, is reeled in by the below-described reel unit 209. The form of the bobbin 206 is not limited to the aforementioned roll bobbin. For example, in the case where a cloth-like or cord-like base fiber is used, a winding shaft adapted to that form may be used.

The reel unit 209 perpendicularly raises the base fiber 211 at a constant speed from the conductor solution 204 housed in the immersion container 205, taking in and winding the base fiber 211 around it. Here, as with the aforementioned bobbin 204, a turnable reel may be used that has the form of a roll bobbin or the like. As described in detail below, the reel unit 209 has a configuration which can adjust the travel speed of the base fiber 211 to adjust the amount of the conductor 212 that is electrochemically polymerized and fixed on/in the base fiber 211.

In the present embodiment, by perpendicularly raising the base fiber 211 from the conductor solution 204 by the reel unit 209, the amount of conductor 212 that impregnates and/or adheres to the base fiber 211 is kept constant, thereby producing uniform electrochemical polymerization and fixation by energization.

As shown in FIG. 13, in the production device 210, multiple electrodes 202 and 203 are alternately provided which energize the traveling base fiber 211 that is perpendicularly raised by the reel unit 209, and which electrochemically polymerize and fix the conductor 212 that impregnates and/or adheres to the base fiber 211. These multiple electrodes 202 and 203 are multiply provided in the lengthwise direction of the base fiber 211, and are respectively disposed on both sides in the lateral direction of the base fiber 211, resulting in a configuration where the base fiber 211 is interposed between the multiple electrodes 202 and 203. A constant current or a constant voltage is impressed on these multiple electrodes 202 and 203 from a direct-current stabilized power supply (not illustrated in the drawing).

The multiple electrodes 202 and 203 may also be disposed vertically, provided that the effects of the invention of the present patent application are obtained. A distance is preferably provided between the electrodes so that they do not contact each other, but the distance may be selected at one's discretion. The number of electrodes may also be selected at one's discretion, and there should be one or more electrode combinations of positive terminal and negative terminal. For example, the aforementioned combination(s) may be within a range from 1 to 10, or a range from 2 to 8, or a range from 3 to 5.

In the example shown in FIG. 13, the multiple electrodes 202 are positive terminals, and the multiple electrodes 203 are negative terminals. By this means, in FIG. 13, the base fiber 211 impregnated with and/or adhering to the conductor 212 transits the various electrodes in the order of "positive terminal (+)"-"negative terminal (−)"-"positive terminal (+)"-"negative terminal (−)" while traveling perpendicularly. In this manner, the positive terminal and the negative terminal are alternately applied.

The multiple electrodes 202 and 203 are, for example, composed of conductive metal material or carbon material, and energize the base fiber 211 in the lengthwise direction while contacting the aforementioned base fiber 211 that travels perpendicularly. Thus, the traveling base fiber 211 is energized between the electrodes, whereby the PEDOT-PSS contained in the conductor 212 that impregnates and/or adheres to the base fiber 211 is polymerized, and electrochemically fixed by polymerization.

As these multiple electrodes 202 and 203, one may use without any restriction known electrodes of various forms that have previously been used in the electrode field such as metal rods or metal plates with smooth surfaces. In particular, in the case where comb teeth-like electrodes are adopted that have multiple comb teeth (electrodes), it is possible to further raise the efficiency of the electrochemical polymerization and fixation of the conductor 212 relative to the base fiber 211.

Figure 14:
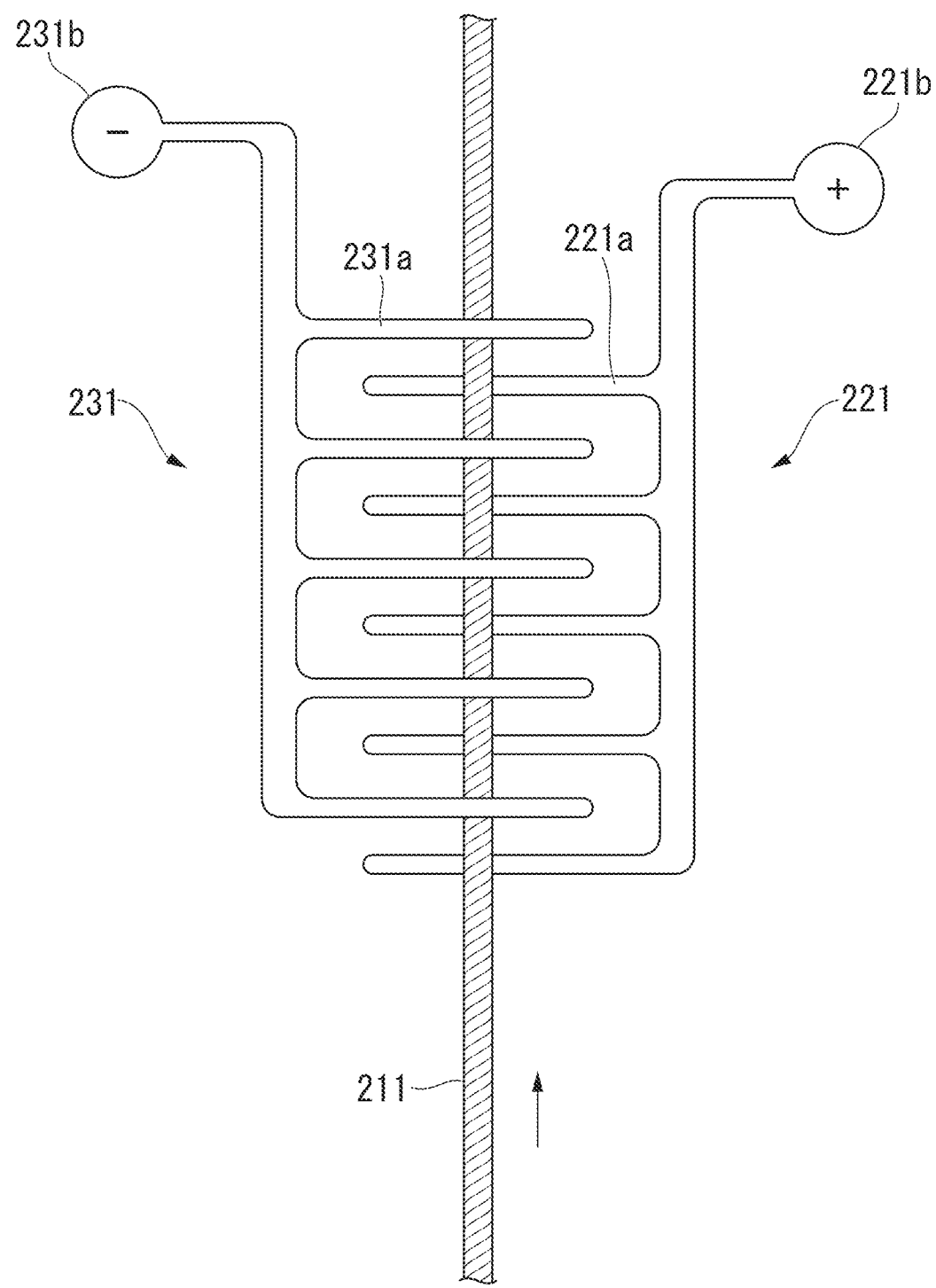
FIG. 14 is detail enlargement which schematically shows an example of an embodiment of the method and the device for producing the conductive polymer fibers of the present invention, and is a drawing which shows a situation where comb teeth-like electrodes are disposed on both sides of base fibers.

FIG. 14 shows a detail enlargement of an example where the multiple electrodes (code numbers 202 and 203) shown in FIG. 13 are configured from the comb teeth-like electrodes 221 and 231 having multiple comb teeth. The number of comb teeth may be selected at one's discretion. The comb teeth-like electrodes 221 and 231 shown in FIG. 14 have comb teeth 221a and 231a that are multiply provided in the lengthwise direction of the base fiber 211, and are disposed so as to sandwich the aforementioned base fiber 211 from both sides in the radial direction of the base fiber 211. The multiple comb teeth 221a and 231a are disposed so as to respectively combine in an alternating manner in the lengthwise direction of the base fiber 211 from both sides in the radial direction of the base fiber 211. The comb teeth-like electrodes 221 and 231 energize the base fiber 211 that is compelled to travel in the direction of the arrow mark in FIG. 14, while the multiple comb teeth 221a and 231a are pressed against the base fiber 211 from both sides in the radial direction of the base fiber 211, and guide it. During this time, the comb teeth-like electrodes 221 and 231 are supplied with a constant current or constant voltage by connection of a direct-current stabilized power supply, which is not illustrated in the drawing, to the terminals 221b and 231b.

As stated above, by alternately arranging positive terminals (comb teeth 221a) and negative terminals (comb teeth 231a) along the travel direction of the base fiber 211, the comb teeth-like electrodes 221 and 231 repeatedly energize the aforementioned base fiber 211 in a short time by contact with the base fiber 211, enabling polymerization and fixation of the PEDOT-PSS.

In the present embodiment, first, the base fiber 211 is compelled to travel in the vertical direction, whereby the conductor 212 that is fixed thereto is uniformly dispersed over the interior and exterior of the fiber bundle composed of the base fiber 211, preventing irregularities. Furthermore, by using the comb teeth-like electrodes 221 and 231 as the multiple electrodes, and by continuously arranging the comb teeth (positive terminals) 221a and the comb teeth (negative terminals) 231a in an alternating manner, polymerization and fixation of the conductor 212 relative to the base fiber (fiber bundle) 211 can be conducted several times in one transit.

Moreover, as the configuration is such that each of the multiple comb teeth (electrodes) 221a and 231a are connected in alignment, applied voltage can be set low, because the combined resistance between electrodes is reduced. Generally, when the voltage applied to the respective electrodes is set high, problems such as degradation tend to occur due to the electrolysis of water and the heating of polymer. It is therefore preferable to set applied voltage as low as possible within a range enabling polymerization and fixation. Thus, when the voltage applied to the electrodes is set low, it is necessary to have an efficient flow of the current required for polymerization of polymer. From this standpoint, as well, it is preferable to use the comb teeth-like electrodes 221 and 231 of the foregoing configuration. During this time, the voltage applied to the comb teeth-like electrodes 221 and 231 can be set at one's discretion, and can, for example, be set to a range of 0.1-18 (V).

In the present embodiment, the configuration using the comb teeth-like electrodes 221 and 231 which constitute multipolar electrodes provided with the multiple comb teeth 221a and 231a utilizes the characteristic that PEDOT-PSS (conductor 212) that has already been electrochemically polymerized normally does not undergo decomposition after polymerization even under a reverse current flow. Consequently, during the process in which the base fiber 211 travels through the comb teeth-like electrodes 221 and 231, polymerization and fixation is conducted when a positive terminal (+ pole) is approached, and electrochemical polymerization is repeated by travel between the comb teeth-like electrodes 221 and 231 that constitute multipolar electrodes, laminating the conductor 212 containing PEDOT-PSS onto the base fiber 211.

There are no particular limitations on the size of the comb teeth-like electrodes 221 and 231, and the distance between comb teeth (distance between electrodes) of the multiple comb teeth 221a (231a) is preferably in a range of 1-50 mm, and is preferably about 10 mm from the standpoint of treatment efficiency of electrochemical polymerization and fixation.

The multiple electrodes (code numbers 202 and 203) shown in FIG. 13 are not limited to the comb teeth-like electrodes 221 and 231 described above. For example, the multiple electrodes may be configured from rotor electrodes 222 and 232 which are multiply disposed in the lengthwise direction of the base fiber 211, and which are disposed so as to sandwich the aforementioned base fiber from both sides in the radial direction of the base fiber 211, as shown in the detail enlargements of FIG. 15A-15C. In the example shown in FIG. 15A-15C, the rotor electrodes 232 disposed on one side in the radial direction of the base fiber 211 are roller shaped, and the rotor electrodes 222 disposed on the other side are pulley shaped. These rotor electrodes 222 and 232 are respectively disposed in an alternating manner in the lengthwise direction of the base fiber 211.

Figure 15A:
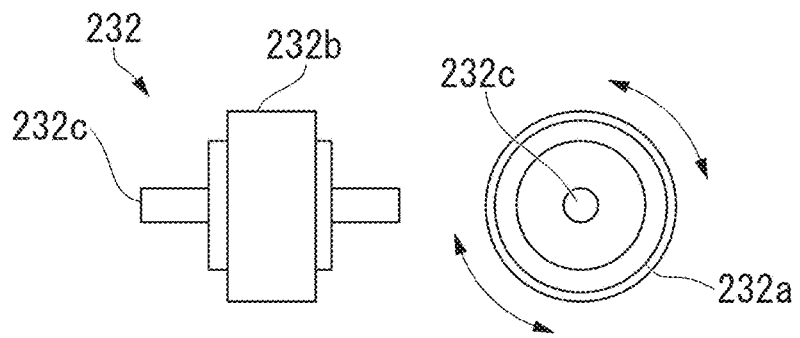
FIG. 15A is a detail enlargement which schematically shows an example of an embodiment of the method and the device for producing the conductive polymer fibers of the present invention, and is a drawing which shows an example of a roller-like rotor electrode.
Figure 15B:
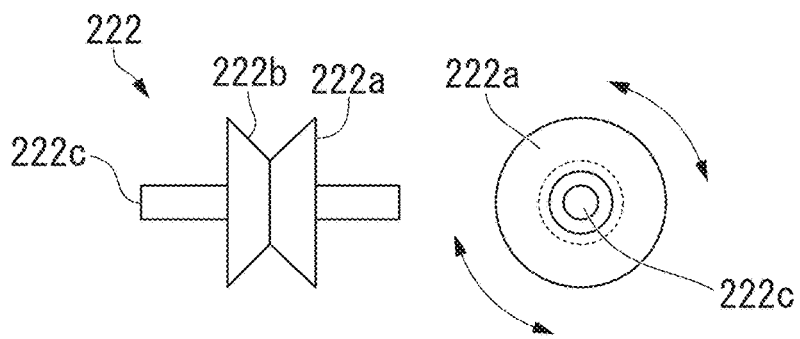
FIG. 15B is a drawing which shows an example of a pulley-like rotor electrode.
Figure 15C:
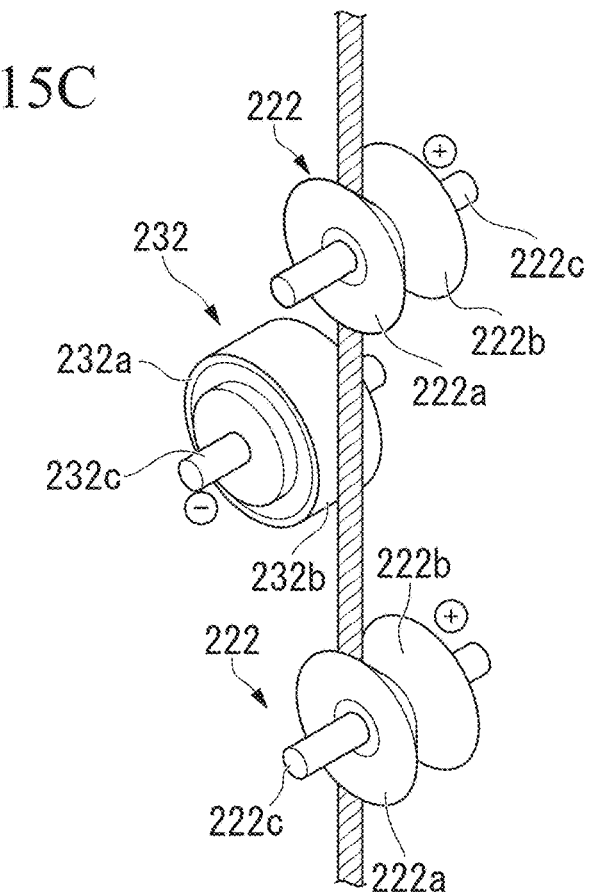
FIG. 15C is a drawing which shows an example of a situation where roller-like rotor electrodes and pulley-like rotor electrodes are alternately combined in the lengthwise direction of base fibers.

As shown in FIG. 15C, when the rotor electrodes 222 and 232 are used as the multiple electrodes, the base fiber 211 is energized by traveling between the respective multiple electrodes 222 and 232, while the roller-shaped rotor electrodes 232 press against the base fiber 211, and guidance is provided by the hollows 222b formed in the pulley-shaped rotor electrodes 222.

As shown in FIG. 15A, the roller-shaped rotor electrodes 232 are considered as negative terminals (−) in the present embodiment, and are configured by joining a metal shaft 232c to a roller 232a. As the (−) side of the direct-current stabilized power supply (not illustrated in the drawings) is connected to the metal shaft 232c, metal material having conductivity is used as this metal shaft 232c. With respect to the roller 232a, for example, a metallic compact roller is used which is composed of stainless steel, and which incorporates a rotatable ball bearing.

As shown in FIG. 15C, the roller-shaped rotator electrode 232 is contacted at its outer circumferential surface 232b by the base fiber 211 that travels in the vertical direction. Consequently, although the size of the roller 232a may be selected as necessary, taking into consideration the travel speed and the like of the base fiber 211, for example, a roller with a diameter of about 6 mm and a width of about 3 mm can be used.

As shown in FIG. 15B, the pulley-shaped rotor electrodes 222 are considered as positive terminals (+) in the present embodiment, and are configured by joining a pulley 222a formed with a hollow 222b on its circumferential surface to a metal shaft 222c. As the (+) side of the direct-current stabilized power supply (not illustrated in the drawings) is connected to the metal shaft 222c, a metal material having conductivity is used as this metal shaft 222c, as in the case of the roller-shaped rotor electrode 232. As the pulley 222a, for example, a metallic compact pulley is used which is composed of stainless steel, and which incorporates a rotatable ball bearing.

As shown in FIG. 15C, the pulley-shaped rotor electrode 222 is contacted at the hollow 222b, which is formed on the circumferential surface thereof, by the base fiber 211 that travels in the vertical direction, and guides the fiber. Consequently, although the size of the pulley 222a may be selected as necessary as in the case of the roller-shaped rotor electrode 232, taking into consideration the travel speed and the like of the base fiber 11, for example, a pulley with a diameter of about 8 mm and a width of about 4 mm may be used.

In the present embodiment, as shown in FIG. 15C, the pulley-shaped rotor electrodes 222 and the roller-shaped rotor electrodes 232 are configured to be alternately disposed, i.e., to alternately dispose positive terminals (+) and negative terminals (−), along the vertical travel direction of the base fiber 211 (see also code numbers 202 and 203 in FIG. 15A-15C).

The base fiber (fiber bundle) 211 that is impregnated with and/or adheres to the conductor 212 then contacts the metallic pulley-shaped rotor electrodes (positive terminals) 222 and roller-shaped rotator electrodes (negative terminals) 232 that are respectively fixed to the metal shafts 222c and 232c, and that incorporate bearings. By supplying power at constant current or low-voltage from a direct-current stabilized power supply (not illustrated in the drawings) to these respective rotor electrodes 222 and 232, the conductor 212 containing PEDOT-PSS is electrochemically polymerized, and fixed to the base fiber 211.

In the case where the rotor electrodes 222 and 232 described above are used, the amount of electricity required to polymerize and fix the conductor 212 containing PEDOT-PSS may be selected at one's discretion. For example, when silk thread with a diameter of approximately 280 μm (No. 9 silk thread, produced by Fujix, Ltd.) is used as the base fiber, it is possible to obtain satisfactory polymerization and fixation of 0.1-6 mC, and particularly of about 3 mC, per 10 mm.

The rotor electrodes 222 and 232 described above rotate together with the traveling base fiber 211. As the friction associated with contact is reduced by this, it is possible to prevent friction-induced peeling of the conductor 212 containing PEDOT-PSS that is electrochemically fixed to the base fiber 211. That is, surface breakdown of the polymer in the conductive polymer fiber 201 can be avoided.

In the production device 210 of the present embodiment, an arrangement of a thread-like fiber bundle can be ordered by having the roller-shaped rotor electrodes 232 press against the base fiber 211, and by providing guidance with the hollows 222b of the pulley-shaped rotor electrodes 222. By this means, it is possible to adopt a configuration that enables energization to be conducted while controlling the amount of conductor 212 that impregnates and/or adheres to the base fiber 211. In this case, for example, regulation is conducted with respect to the form and dispositional format of the pulley-shaped rotor electrodes 222 and the roller-shaped rotor electrodes 232, as well as the tensile force, travel speed, and turning condition of the base fiber (fiber bundles) 201. By this means, with respect to the base fibers, it is possible to adjust opening, bundling function, fiber interval, fiber bundle arrangement (form), and so on.

By adjusting the interval between the respective fibers with the above-described adjustment, for example, it is then possible to retain and fix an optional amount of conductor 212 (42) among the respective base fibers, as in the example shown in FIG. 6. In particular, it becomes possible to conduct adjustment into the various forms stated above by implementing form sets of the base fibers (fiber bundles) 211 utilizing the pulley-shaped rotor electrodes 222 and the roller-shaped rotor electrodes 232.

As set forms of fiber bundles, one may cite various forms such as, for example, the presence or absence of twisting of fiber bundles, cross-sectional forms of fiber bundles (flattened, true circle, ellipse, square, etc.), and turning of fiber fascicles (straightening of fascicle of fiber bundles by reversing twist, or further application of twisting). Form sets should be implemented by suitably selecting these with adjustments. In the present embodiment, by implementing the aforementioned form sets of fiber bundles, it is possible to obtain composite fiber bundles of the conductive polymer fiber 201 that are set (formed) into prescribed forms. When forming such composite fiber bundles, as in the example shown in FIG. 6, a high order structure such as twisted cord, cloth, or nonwoven cloth can be made by arranging the conductor 212 (42) containing the PEDOT-PSS that is a conductive polymer among multiple base fibers 211 (41)

with close adhesion to the base fiber 211 (41), and by intertwining and/or weaving together the multiple base fibers 211 (41).

As shown in FIG. 13, in addition to the foregoing configuration, the production device 210 of the present embodiment may also be provided with a dryer 208 that blows air toward the base fiber 211 in/on which the conductor 212 is polymerized and fixed, and a chamber (including a humidity regulator) 207 which regulates atmospheric humidity in the vicinity of the base fiber 211.

The chamber 207 is provided with an air conditioning function (humidity regulator), and constantly maintains a concentration (PEDOT-PSS concentration) of the conductor 212 by maintaining internal humidity at a high humidity. As this type of chamber 207, one may use, without any restriction, a constant temperature/constant humidity tank of a size enabling housing of the multiple electrodes 202 and 203 and the immersion container 205, which has been conventionally used in this field.

The dryer 208 blows dry air of low humidity toward the base fiber 211 in/on which the conductor 212 has been polymerized and fixed (the conductive polymer fiber 201), and dries it. For example, conventional air-blowing dryers configured from a motor, a fan, and the like may be adopted without any restriction.

In the present embodiment, it is also possible to conduct moisture adjustment for the PEDOT-PSS solution (conductor 212) that impregnates the base fiber (fiber bundle) 211 by using the aforementioned chamber, and conducting humidity adjustment in the vicinity of the multiple electrodes 202 and 203.

In the case where the chamber is given a 3-part configuration to independently regulate humidity in each part, it is possible to have settings like those shown in the following (A)-(C).

(A) Immersion container: the humidity control of the part is adjusted to a range of 50-100%, in order to prevent evaporation of moisture from the conductor solution containing PEDOT-PSS, and constantly maintain a concentration of PEDOT-PSS.

(B) Multiple electrodes: adjustment of the moisture of the conductor solution containing PEDOT-PSS that impregnates the fiber is conducted by controlling humidity from high humidity to low humidity, e.g., in a range of 99-10%.

(C) Dryer: a function for blowing dry air (e.g., the humidity setting is in a range of 0-40%) can be added, in order to accelerate drying of the base fiber in/on which the conductor has been polymerized and fixed (the conductive polymer fiber) by circulation of low-humidity dry air.

In addition to the respective configurations described above, although omitted from the drawings, the production device of the present embodiment may also be provided with, for example, a container-like disinfectant and cleaning unit which conducts fixation and sterilization/disinfection of residual monomers by an ethanol or acetone bath. Furthermore, the disinfection and cleaning unit may be additionally provided with a configuration enabling removal of residual monomers by a cleaning bath of physiological saline solution or the like.

Figure 16:
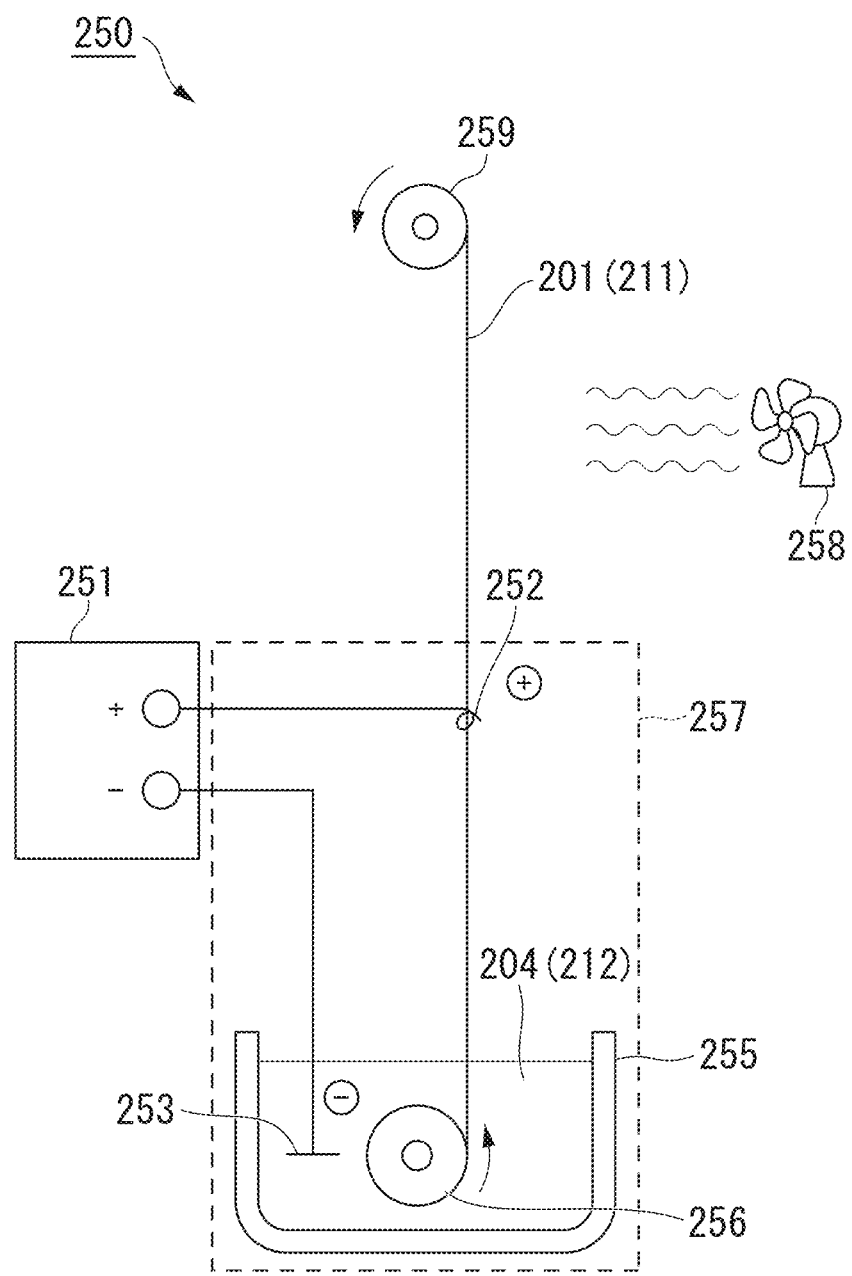
FIG. 16 is a diagram which schematically shows another example of an embodiment of the method and the device for producing the conductive polymer fibers of the present invention, and is a drawing which shows the case where a single electrode is used.

Moreover, the electrodes used in the present invention are not limited only to multiple electrodes like those shown in FIG. 13-15. It is also acceptable to have, for example, a production device 250 provided with monopolar (individual) electrodes 252 and 253, as shown in FIG. 16. This production device 250 is provided with an immersion container 255 which houses a PEDOT-PSS solution 204. It also includes: an electrode (negative electrode) 253 consisting of a metal plate or the like, which is installed in the PEDOT-PSS solution inside the immersion container 255; an electrode (positive terminal) 252 consisting of a metal rod or the like, which is installed outside the immersion container 255, and which contacts the base fiber 211; a bobbin 256 which is installed inside the immersion container 255, and around which is wound the base fiber 211; a chamber 257 with internal humidity regulation, which houses each electrode 252, 253, the immersion container 255, and the bobbin 256; a direct-current stabilized power supply 251 which supplies current to the electrodes 252 and 253; a dryer 258 which conducts air-blow drying of the base fiber 201 (conductive polymer fiber 201); and a reel unit 259 which takes in the conductive polymer fiber 201 after completion thereof.

When this type of production device 250 provided with the individual (monopolar) electrodes 252 and 253 is used, the base fiber 211 travels between the electrodes while being raised perpendicularly, whereby the conductor 212 which is polymerized and fixed in the base fiber 211 can be uniformly dispersed, preventing irregularities, with the result that it is possible to manufacture conductive polymer fiber 201 of excellent conductivity and durability.

(Production Method)

A procedure of a method for producing the conductive polymer fiber 201 using the above-described production device 210 is described below with reference to the same drawings (FIG. 13-15) used to describe the aforementioned production device.

A method for producing the conductive polymer fiber 201 described in the present embodiment is sequentially provided with the respective steps shown in (1)-(3) described below, and each of these steps (1)-(3) are also conducted while regulating atmospheric humidity.

(1) An immersion step in which the insulating base fiber 211 composed of thread-like fiber bundles is immersed in a conductor solution containing PEDOT-PSS as conductive polymer, thereby causing the conductor 212 to impregnate and/or adhere to the base fiber 211.

(2) A fixation step in which the conductor 212 that impregnates and/or adheres to the base fiber 211 is electrochemically polymerized and fixed by energizing the base fiber 211 by compelling it to travel between the multiple electrodes 202 and 203 while being perpendicularly raised from the conductor solution.

(3) A drying step in which the base fiber 211 in/on which the conductor 212 has been polymerized and fixed is dried by air blowing.

(Immersion Step)

In the immersion step, as stated above, the base fibers 211 are immersed in the conductor solution containing PEDOT-PSS as conductive polymer, thereby causing the conductor 212 to impregnate and/or adhere to the base fibers 211.

Specifically, a conductor solution containing PEDOT-PSS which is a conductive polymer is stored in the immersion container 205, as shown in FIG. 13, and the base fibers (fiber bundles) 211 are immersed in this solution. By this step, the conductor 212 having conductivity impregnates and/or adheres to the base fibers 211, with the result that the base fibers 211 have conductivity.

When adjusting a conductor solution containing conductive polymer like that described above, for example, additives and the like can also be added as necessary to a commercial PEDOT-PSS solution (Heraeus, Ltd.: CLEVIOS P and the like). That is, a method may also be applied wherein a mixed solution is prepared in which an additive is mixed with the conductor solution containing PEDOT-PSS, and the conductive polymer and additive are simultaneously applied to or used to immerse the base fibers 211. Such a mixed solution may be selected at one's discretion. As one example, one may cite an aqueous solution containing a concentration of 0.1-50 (V/V) % of conductive polymer such as PEDOT-PSS, and 0.1-50 (V/V) % of an additive such as glycerol. There are no particular limitations on the additive concentration in the conductor solution, and it may, for example, be in a range of 0.1-50 wt %.

(Fixation Step)

Next, in the fixation step, the base fibers 211 are energized by traveling between the multiple electrodes 202 and 203 while being perpendicularly raised from the solution. By this means, the conductor 212 that impregnates and/or adheres to the base fibers 211 is electrochemically polymerized and fixed.

Specifically, for example, the base fibers (fiber bundles) 211 in/on which the conductor 212 is impregnated and/or adheres are compelled to travel by being perpendicularly raised from the solution by the reel unit 209, as shown in FIG. 13. Thus, by causing the base fibers 211 to travel while being perpendicularly raised, a condition is produced in which the conductor 212 is free of gravity-induced eccentricity, and impregnates and/or adheres to the base fibers 211 with uniform dispersion.

Then, in the fixation step, the multiple electrodes 202 and 203 shown in FIG. 13 are used to energize the base fibers 211 while making contact so as to sandwich them from both sides in the radial direction. Thus, the base fibers (fiber bundles) 211 in/on which the conductor 212 containing PEDOT-PSS is impregnated and/or adheres are brought into contact with the electrodes 202 and 203, to cause a current flow, whereby the conductor 212 containing PEDOT-PSS adhering to the interior and exterior of the fiber bundles is electrochemically polymerized and fixed, and the conductive polymer fibers 201 are obtained which are composite fibers of the base fibers (fiber bundles) 211 and the conductor 212 containing PEDOT-PSS.

In the fixation step, the above-described comb teeth-like electrodes 221 and 231 having multiple comb teeth 221a and 231a shown in FIG. 14 may be used as the multiple electrodes. In this case, the comb teeth-like electrodes 221 and 231 are disposed so as to sandwich the aforementioned base fibers 211 from both sides in the radial direction of the base fibers 211, and the multiple comb teeth 221a and 231a are disposed so as to be positioned in an alternating manner in the lengthwise direction of the base fibers 211 from both sides in the radial direction of the base fibers 211. A method can then be adopted wherein the base fibers 211 are energized by perpendicularly traveling while the multiple comb teeth 221a and 231a provided in the comb teeth-like electrodes 221 and 231 press against the base fibers (fiber bundles) 211 from both sides in the radial direction, and provide guidance.

In the fixation step, as the multiple electrodes, it is also possible to use the rotor electrodes 222 and 232 shown in FIG. 15A-15C, which are multiply disposed in the lengthwise direction of the base fibers 211, and which are disposed so as to sandwich the base fibers 211 from both sides in the radial direction of the aforementioned base fibers 211.

That is, using the roller-shaped rotor electrodes 232 disposed on one side in the radial direction of the base fibers 211 and the pulley-shaped rotor electrodes 222 disposed on the other side, the rotor electrodes 222 and 232 disposed on both sides of the base fibers 211 are disposed in an alternating manner in the lengthwise direction of the base fibers 211. A method can then be adopted wherein the base fibers 211 are energized by traveling between the respective multiple electrodes while the roller-shaped rotor electrodes 232 press against the base fibers (fiber bundles) 211, and guidance is provided by the hollows 222b formed in the pulley-shaped rotor electrodes 222.

Furthermore, in the fixation step, a method can be adopted wherein energization is conducted while controlling the amount of the conductor 212 that impregnates and/or adheres to the base fibers 211 by ordering an arrangement of a thread-like fiber bundle by having the base fibers 211 pressed by the roller-shaped rotor electrodes 232, and guided by the hollows 222b in the pulley-shaped rotor electrodes 222, as described with respect to the foregoing production device configuration.

(Drying Step)

Next, in the drying step, the conductive polymer fibers 201 are dried by blowing low-humidity dry air toward the base fibers 211 in/on which the conductor 212 is polymerized and fixed, i.e., the conductive polymer fiber 201.

Specifically, as shown in FIG. 13, for example, dried air is blown toward the base fibers (fiber bundles) 211 in/on which the conductor 212 has been electrochemically polymerized and fixed in the aforementioned fixation step, using the dryer 208 provided with a humidity regulation means (not illustrated in the drawing) and an air blowing means. By this means, the water (solvent) contained in the solution of the conductor 212 containing PEDOT-PSS is removed by drying.

Subsequently, with the production method of the present embodiment, it is preferable to remove the unpolymerized PEDOT-PSS and the solvent by cleaning the conductive polymer fibers 201 using, for example, an electrolytic solution consisting of physiological saline water or the like.

Furthermore, in the present embodiment, drying is preferably conducted after performing cleaning and disinfection of the conductive polymer fibers 201 using an ethanol solution.

Although detailed description is omitted, in the production method of the present embodiment, it is also possible to manufacture the conductive polymer fibers 201 using the production device 250 provided with the monopolar (individual) electrodes 252 and 253 shown in FIG. 16.

According to the above-described method for producing the conductive polymer fibers 201 of the present invention, as stated above, a method is adopted wherein the base fibers 211 in/on which the conductor 212 containing PEDOT-PSS is impregnated and/or adheres are energized by traveling between the multiple electrodes 202 and 203 while being perpendicularly raised from the conductor solution. As the process in which the conductor 212 is electrochemically polymerized and fixed in the base fibers 211 can be continuously conducted in a one-step process by this method, productivity is improved. Furthermore, by having the base fibers 211 travel between the multiple electrodes 202 and 203 while being perpendicularly raised, the conductor 212 that is polymerized and fixed in the base fibers 211 is uniformly dispersed, enabling prevention of irregularities. It is therefore possible to manufacture with good productivity the conductive polymer fibers 201 which are provided with a high degree of biocompatibility and satisfactory uniformity, as well as excellent conductivity and durability.

Moreover, according to the conductive polymer fiber production device 210 of the present invention, a configuration is adopted which is provided with the reel unit 209 that perpendicularly raises the base fibers 211 in/on which the conductor 212 containing PEDOT-PSS is impregnated and/or adheres from a conductor solution in the immersion container 205, and the multiple electrodes 202 and 203 which energize the base fibers 211 during travel. As the process in which the conductor 212 is electrochemically polymerized and fixed in the base fibers 211 can be continuously conducted in a one-step process by this method, productivity can be improved. Furthermore, by providing the multiple electrodes 202 and 203 which energize the base fibers 211 while they are perpendicularly raised, the conductor 212 that is polymerized and fixed in the base fibers 211 is uniformly dispersed, enabling prevention of irregularities. It is therefore possible to obtain with good productivity the conductive polymer fibers 201 which are provided with a high degree of biocompatibility and satisfactory uniformity, as well as excellent conductivity and durability.

Regarding the Third Aspect

The third aspect of the present invention relates to a biological electrode and a biological signal measurement device. In further detail, the present invention relates to a biological electrode of the body surface attachment type utilizing composite material of conductive polymer and fiber (hereinafter "conductive composite fiber"), and to a biological signal measurement device provided with the biological electrode. In the present aspect, the fiber described in the first aspect of the present invention can be preferentially used.

Embodiments of the third aspect of the present invention are described below with reference to drawings, but the present invention is not limited by the pertinent embodiments.

<<An Example Using a Biological Electrode as a Brainwave Measurement Electrode>>

In recent years, brainwave measurement is not only being conducted by testing in medical facilities, but applications are also advancing with respect to home-based brainwave testing, telemedicine, health information and ubiquitous healthcare systems, and the like.

Furthermore, applications are also anticipated outside of the medical treatment field with respect to psychological research involving measurement of event-related potential, engineering such as BCI (brain computer interface), and the welfare and nursing-care field.

In brainwave measurement, it is necessary to attach the electrode with avoidance of the hair that exists on the scalp.

With respect to brainwave measurement using conventional biological electrodes, in order to stably fix the electrodes, the electrodes are fixed to skin using an adhesive agent, or the electrodes are fixed by pressure from above using a head cap that covers the entire head, and/or the electrodes are prevented from coming off by copious amounts of paste or gel between the electrodes and the scalp. However, these countermeasures have many inconveniences associated with attachment, impose a large burden on the subject, and are particularly problematic when conducting continuous measurement of brain waves over a long period. Moreover, as the external appearance of the electrodes creates significant discomfort in the subject or in bystanders, utilization of brain waves beyond medical treatment applications has not become widely generalized.

As the biological electrode of a first embodiment of the third aspect of the present invention described below utilizes the conductivity of conductive polymer, it becomes possible to downsize the electrode, and decrease the skin contact area. Furthermore, this electrode which is composed by flexible fiber material imparts little irritation to skin when attached, and inhibits discomfort during attachment. There is also no need to seal the skin with highly viscous gel or tape or the like as with conventional biological electrodes. As the biological electrode of the first embodiment of the third aspect of the present invention has an excellent wear feeling, is capable of continuous use, and has an external appearance that causes no discomfort during attachment, it can also be preferentially used, for example, in brainwave measurement applications.

First Embodiment of Third Aspect

The biological electrode of the first embodiment is provided with cord-like contacts composed of conductive polymer fiber. It is capable of measuring brain waves by attachment of the aforementioned contacts to the scalp in the gaps between scalp hair (see FIGS. 19A-19D, and FIGS. 20A-20D).

A biological electrode 310 shown in FIGS. 19A-19D is at least provided with cord-like contacts 311 composed of conductive polymer fiber, first frames 312, and a second frame 313 (connecting parts). The two ends of the contact 311 are connected with the two ends of the arcuate first frame 312. The flexible form of the contact 311 is provided by the first frame. Tension may be imparted to the contact 311 by the first frame 312. The second frame 313 that is laid across the multiple first frames 312 functions as a beam that fixes the respective first frames 312. In addition, a signal cable 314 is connected to a terminal of each contact 311. Electrical signals are transmitted and received between each contact 311 and a brainwave analyzer (not illustrated in the drawings) connected to the distal end of the signal cable 314. The direction of the electrical signals may be only one-way, or it may be bidirectional-way.

There are no particular limitations on the form of the contacts 311, provided that it is a form enabling contact with the scalp S, and any form such as a cord-like, thread-like, band-like, cloth-like, net-like, or other form is acceptable. The size and length of the contacts 311 may also be suitably adjusted.

There are no particular limitations on the form, number, or size of the first frames 312 and the second frame(s) 313. For example, one may adopt a form which enables appropriate tension to be imparted to the contacts 311, or a form which enables fixing of the contacts 311 so that they do not loosen. There are no particular limitations on the material composing the first frames 312 and the second frame(s) 313, provided that it is not a material that disturbs electrical signals in the contacts 311, and conventional resin material may be used. As examples of the number of the first frames 312, one may cite a number included in a range from 1 to 20, a range from 2 to 8, a range from 2 to 4, or the like. As examples of the number of the second frame(s) 313, one may cite a number included in a range from 1 to 6, a range from 1 to 3, a range from 1 to 2, or the like. With respect to the form of the first frames 312 and the second frame(s) 313, for example, a partially looped shaped is acceptable, and a tabular shape is also acceptable. Thickness is preferably constant, but may vary in parts. In the drawings, a single second frame 313 is disposed at right angles to four first frames 312, but the second frame(s) 313 may be positioned in a plurality, and/or may be diagonally arranged as necessary.

Provided that brainwave measurement (signal measurement) is not impaired, at least either of the first frames 312 and the second frame(s) 313 may be made of metal. For example, by composing the first frames 312 and the second frame(s) 313 of metal material, one may adopt a configuration wherein the signal cable 314 is connected to either the first frame 312 or the second frame 313 without connection to the contact 311, and transmission and receipt of electrical signals vis-à-vis the contact 311 is conducted via the first frame 312 or the second frame 313.

There are no particular limitations on the connection method of the signal cable 314 and the conductive composite fiber composing the contacts 311, provided that it is a method enabling electrical connection. For example, one may apply caulking that uses metal, winding/ligation of the conductive composite fiber around/to the signal cable 314, or adhesion by a conductive adhesive agent.

Figure 22A:
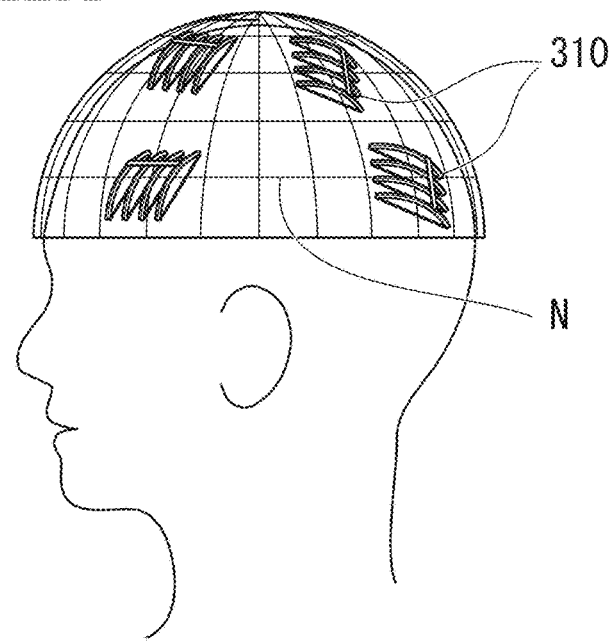
FIG. 22A is a schematic view which shows a condition where comb teeth-like biological electrodes 310 are inserted into scalp hair, and a stretchable net-shaped holder N is applied from above to hold the biological electrodes 310.
Figure 22B:
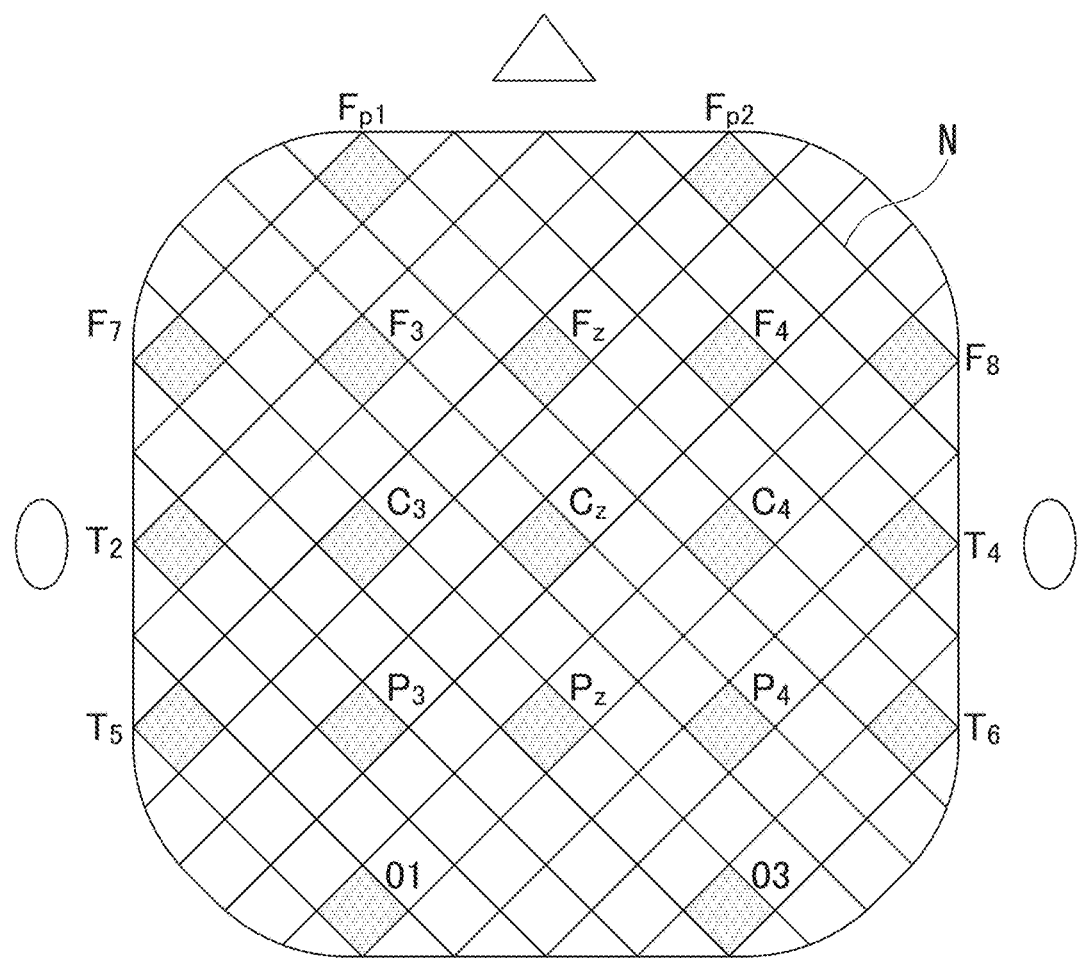
FIG. 22B is a top view which shows an example where the biological electrodes 310 are installed in the retractable net N in conformity with International Technique 10-20.

In the present invention, one or more of the cord-like contacts 311 may be used per electrode. As illustrated in FIG. 19A-19D using the first frames 312 and the second frame 313, stable contact is obtained between the contacts 311 and the skin by configuring the comb-shaped electrode 310. In the comb-shaped biological electrode 310 shown in FIG. 19A-19D, multiple cord-like contacts 311 are arranged in parallel. The comb-shaped electrode 310 in which the multiple contacts 311 are arranged in parallel is inserted between hair or in the manner of a comb when there is scalp hair growth, and a net-like holder can also be put on over the comb to fix it in place (FIG. 22A-22B).

Variation of First Embodiment of Third Aspect

As a configuration of a more compact biological electrode, a hairpin-like biological electrode 320 in which two contacts 321 are fixed to a hairpin-like hair clip (metal plate spring) is shown in FIG. 20A-20D. This hairpin-like biological electrode 320 can be used by inserting it to the vicinity of scalp hair roots. The hairpin-like hair clip is able to hold the hair in place. In the illustrated example, two contacts 321 are fixed to a scalp S.

The hairpin-like biological electrode 320 shown in FIG. 20A-20D is at least provided with the cord-like contacts 321 composed of conductive composite fiber, third frames 322, and a fourth frame 323. The two ends of the contact 321 are attached to two cylindrical third frames 322, and it is possible to adjust the tension imparted to the contact 321 by adjusting the distance of the two third frames 322. The two third frames 322 are respectively fixed by a distal end part and a curved part of the fourth frame 324 for that uses a hairpin. In the example shown in FIG. 20A-20D, two cord-like contacts 321 are provided in the hairpin. A terminus of each contact 321 is connected to a signal cable 324, and transmission and receipt of electrical signals is conducted between each contact 321 and a brainwave analyzer (not illustrated in the drawings) connected to the distal end of the signal cable 324. The direction of the electrical signals may be only one-way, or it may be bidirectional way.

There are no particular limitations on the form of the contacts 321, provided that it is a form enabling contact with the scalp S, and a cord-like, thread-like, band-like, cloth-like, net-like, or other form is acceptable. The size and length of the contacts 321 are also adjustable.

There are no particular limitations on the form of the third frames 322, and one may adopt a polygonal column shape such as a cylindrical, triangular prism, or quadrangular prism shape, or a spherical shape or the like. In this configuration, the fourth frame 323 can be fixed to hair H, because it has a hairpin structure, and functions as a hairpin. As a result, the contacts 321 can be easily brought into contact with the skin (scalp) S, and can be fixed at a desired position.

There are no particular limitations on the material composing the third frames 322 and the fourth frame 323, provided that it is material that does not disturb electrical signals in the contacts 321. For example, conventional resin materials can be used. Provided that there is no impairment to brainwave measurement (signal measurement), at least either of the third frames 322 and the fourth frame 323 may be made of metal. In the present variation, for example, the third frames 322 may be composed of insulating resin, and the hairpin that is the fourth frame 323 may be made of metal. Provided that there is no impairment to brainwave measurement, the contacts 321 may be electrically connected to the metallic fourth frame 323.

One or more of the cord-like contacts 321 may be used per electrode. As illustrated in FIG. 20A-20D, stable contact of the contacts 321 and the skin can be obtained by configuring the hairpin-like electrode 320 using the third frames 322 and the fourth frame 323. In the hairpin electrode 320 shown in FIG. 20A-20D, multiple cord-like contacts 321 are arranged in parallel. The hairpin electrode 320 that arranges the multiple contacts 321 in parallel is fixed in place by fastening the hair with the hairpin.

The conductive composite fiber composing the cord-like contacts 321 may be identical to that of the above-described contacts 311.

(Conductive Composite Fiber)

As the conductive composite fiber composing the cord-like contacts 311 and 321, a composite fiber of conductive polymer and conventional fiber material may be applied. There are no particular limitations on the compounding mode (method). For example, it is acceptable to have a form where the conductive polymer coats the surface of the aforementioned fiber material that is cord-like (thread-like), a form where the conductive polymer impregnates the aforementioned fiber material that is cord-like, or a form where cord-like conductive polymer and the aforementioned fiber material that is cordlike are twisted together or spun. The materials and the conductive polymer fiber described in the first aspect may be preferentially used, and the device and method described in the second aspect may be used.

There are no particular limitations on the type of the aforementioned conductive polymer, and conventional conductive polymer may be applied. For example, in addition to the aforementioned PEDOT-PSS, one may cite hydrophilic conductive polymer such as PEDOT-S(poly(4-(2,3-dihydrothieno[3,4-b][1,4]dioxin-2yl-methoxy-1-butanesulfonic acid, potassium salt). By using composite fiber containing hydrophilic conductive polymer as the material of the contacts 311 and 321, adsorbency (adhesion) relative to skin can be easily imparted to the contacts 311 and 321 themselves.

As the aforementioned fiber material, one may apply conventional fiber material such as silk, cotton, hemp, rayon, and chemical fiber. Of these, silk is optimal. When silk is used, the strength and hydrophilicity of the aforementioned composite fiber can be further enhanced. Moreover, when silk is used, the wear feeling is better when skin is contacted.

There no particular limitations on the types of the aforementioned conductive polymer that are combined with silk, but hydrophilic conductive polymer such as the aforementioned PEDOT-PSS or PEDOT-S is preferable.

As the aforementioned conductive composite fiber composing the contacts of the respective embodiments of the present invention, the conductive polymer fiber that is described in further detail below may be applied.

(Structure of Contacts)

As the structure of the cord-like contacts configuring the respective embodiments of the present invention, two types of structure may be exemplified.

A first structure for a cord-like contact is a structure that uses the aforementioned conductive composite fiber bundles alone. As an example of the first structure, one may cite the contact 311 shown in FIG. 19A-19D. As the contact 311 is fabricated by weaving bundled thread (cord) of multiple conductive composite fibers, it has appropriate thickness and strength. As the first structure that is configured only with composite conductive fibers is flexible, it is well-suited for applications requiring flexibility and a comfortable wear feeling with respect to the biological electrode. The aforementioned conductive composite fibers are preferably thread-like or cord-like.

A second structure for cord-like contacts is a structure which combines the aforementioned conductive composite fiber bundle and metallic cable or metallic wire. As an example of the second structure, one may cite the structure schematically shown in FIGS. 21A and 21B. The contact 321 of FIG. 20 has the structure shown in FIG. 21B. As the second structure raises conductivity by means of the metallic cable or metallic wire, it is well-suited to applications requiring a reduction in electrode resistance per contact area of biological electrode.

In the second structure shown in FIG. 21A, a metal wire 321$f$ is wound so as to bring together a bundle of multiple cores 321$g$, on top of which conductive composite fibers 321$e$ are wound. The material composing the cores 321$g$ may be conductive, or it may be insulating. In the illustrated example, the cores 311 are cores composed of insulating fibers. The number and the thickness of the cores 311 may be suitably adjusted.

In the drawing, it is depicted that the number of windings of the metal wire and the number of windings of the conductive composite fibers 321$e$ are identical, but the relative relationship of these winding numbers is not limited thereto. For example, the number of windings of the metal wire 321$f$ may be less than the number of windings of the conductive composite fibers. Moreover, the cord-like contact may be partially coated by an insulating cover 321$z$ as necessary. As an insulating cover, for example, one may cite a cover composed of silicone resin.

Figure 21C:
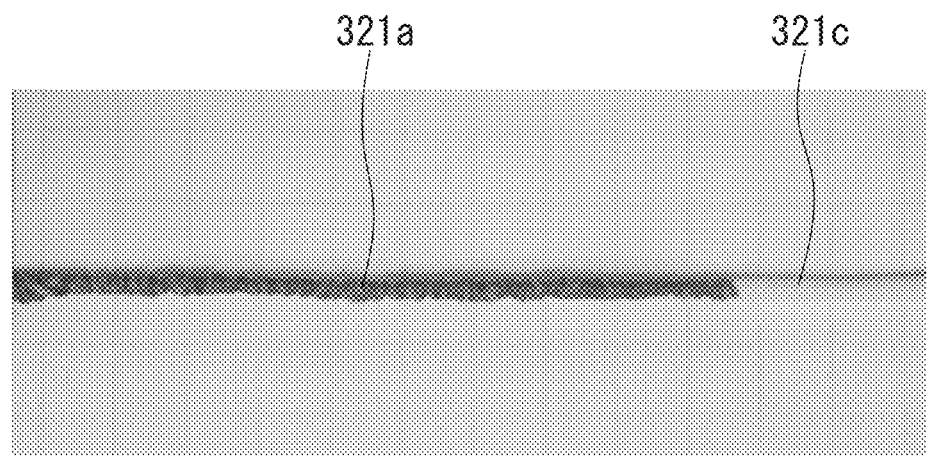
FIG. 21C is a photograph of a cord-like contact 321 having the structure of FIG. 19B.

With respect to the second structure shown in FIG. 21B, conductive composite fibers 321$a$ are wound so as to bring together a bundle of multiple metallic cables 321$b$. There are no particular limitations on the type of metal composing the metallic cables, but highly conductive copper cable is optimal. In the illustrated example, the metallic cables 321$b$ are copper cables. There are no particular limitations on the number or the thickness of the metallic cables 321$b$, and these may be suitably adjusted. However, instead of using a small number of thick metallic cables, use of a large number of thin metallic cables or metallic wires may increase flexibility even at the same diameter of bundle. The cord-like contact may be partially covered by an insulating cover 321$c$ as necessary. As an insulating cover, one may cite, for example, a cover composed of silicone resin. FIG. 21C is a photograph of the cord-like contact 321 having the structure of FIG. 21B.

When the first structure and the second structure are compared, in the first structure, electrical connection of the contact 311 and the metallic (conductive) signal cable 314 occurs at the single point of the terminal of the contact 311, whereas in the second structure, the electrical connection of the contact 321 and the signal cable 324 occurs over the entirety of the contact 321. Therefore, electrode resistance is reduced in the second structure, because the distance between the skin and the metallic cable is shorter than in the first structure.

There are no particular limitations on the thickness of the contact, but it is preferable to have a thickness that obtains a structural strength inhibiting breakage during contact with skin. For example, when thickness of 0.1 mm to 5 mm, a structural strength inhibiting breakage can be easily obtained. Normally, the second structure which has metal wire tends to have greater structural strength than the first structure. As examples of other thickness ranges, one may also cite a thickness of 0.1 mm to 3 mm, a thickness of 0.5 mm to 1 mm, and so on.

As a contact provided with conductive composite fibers has adhesion (adsorbency) relative to skin, the biological electrode of the first embodiment can be independently attached without use of paste or adhesive for electrode attachment. However, it is possible that the biological electrode could come off (peel off) from the skin surface upon application of external force due to an action of the subject or pulling of the signal cable or the like. In order to prevent this, a means can be adopted which presses the biological electrode against the skin surface. The aforementioned means can be exemplified by a net-like holder (cap) N like the one shown in FIG. 22A.

(Holder for Brainwave Electrode; Cap with Stretchable Netting)

Biological electrodes of the first embodiment of the third aspect, for example, the comb-like electrodes 310 shown in FIG. 22A, can be fixed by placing thereon a cap with a stretchable net N shown in FIG. 22A. The net N can be used as a holder for lightly pressing on the comb-like electrodes 310 from above to stably hold them in place. As the comb-like electrodes 310 are inserted between gaps in the hair, they do not easily come off. Consequently, with respect to the comb-like electrodes 310, there is no need to conduct strong pressure fixation with a head cap or the like as with conventional electrodes, and stable fixation can be obtained by using a cover with a low-tension stretchable net or the like. As the aforementioned low-tension stretchable net, for example, commercial net bandages (manufactured by Nippon Eizai Co., Ltd.) and the like may be applied. According to the biological electrode of the first embodiment, a design that fits under hair can be easily achieved. Furthermore, with use of a stretchable net, hair can be pulled out from under the net. Consequently, wear feeling and external appearance during attachment are both improved by use of the biological electrode of the first embodiment. FIG. 22A shows a fitting view of the comb-like electrodes 310 and the cap with the stretchable net N. FIG. 22B shows an example (top view) where the comb-like electrodes 310 are disposed in the stretchable grid-like net N. In FIG. 22B, Δ represents the nose, and the two ellipses respectively represent the left and right ears. Within the region demarcated by the grid, the positions shown by shading represent the places where the comb-like electrodes 310 are disposed. In this configuration, the attachment sites of the biological electrodes 310 can be conformed to the international 10-20 method by adjusting the cord intervals of the stretchable net N.

<<Example where the Biological Electrode is Used as an Electrode for Electrocardiogram Measurement>>

Biological electrodes for Holter electrocardiogram testing and biological electrodes for myogenic potential monitoring or hear rate monitoring have heretofore been widely available. Frequently, electrodes for Holter electrocardiogram testing use highly adhesive tape or adhesive pads, and are used when fixed to skin. Noise generation is prevented by fixing the biological electrodes to skin. As monitoring electrodes which are often continuously used over long periods are fixed to skin, they frequently use adhesive pads of conductive gel. With respect to measurement data from these electrodes, there is little immixture of artifacts such as noise, and the stability of measured waveforms is excellent.

However, there is a problem that high-frequency components of biological signals are attenuated. As electrolytic paste or gel is used between the metallic electrode and the skin with respect to conventional biological electrodes, it is thought that this problem occurs due to the influence of the volumetric components (capacitance) of the electrolyte solution. Consequently, electrolytic paste and electrolytic gel are one factor inhibiting analysis of biological signals containing high-frequency components, and high-speed communication between a living body or the like and an external device in BCI.

With conventional biological electrodes, steaming tends to occur due to the close adhesion of a highly adhesive electrode to skin, causing discomfort to the subject (wearer). Moreover, as a preliminary treatment for obtaining the effect of the adhesive agent, delipidation of the skin surface subject to which adhesion is performed must be conducted with an alcohol swab or the like. However, as delipidation treatment with alcohol is strongly irritating to skin, it is a cause of itchiness and contact dermatitis, and requires improvement.

Problems of steaming and influence to frequency characteristics due to the use of metallic electrodes in this manner are not limited only to electrocardiogram measurement, but also are related to the aforementioned brainwave measurement. Such problems are problems to be solved in terms of transmission of electrical signals or electrical stimulation between the electrode and the living body. Attempts to improve these problems have also been made in the past, but sufficient improvement has not been achieved.

For example, with respect to conventional biological electrodes for brainwave measurement, in order to alleviate the effects on frequency characteristics which are caused by electrolytic paste, attempts have been made to conduct measurement with direct placement on skin of compact electrodes, which is made of sintered metal or the like, without use of electrolytic paste. However, a problem arises with respect to the stability of measured waveforms as a result of the attempts. That is, with a method which conducts direct placement of a metallic electrode on skin, resistance between the skin and the electrode tends to fluctuate due to mechanical compliance and electrochemical mismatch. Furthermore, measured signals tend to destabilize due to vibration from body movement or breathing of the living body, and it often happens that noise becomes intermixed with measured signals. Moreover, hard metallic electrodes tend to cause discomfort or unpleasantness when brought into direct contact with skin, and this point also requires a solution.

In order to alleviate the problems of hard metallic electrodes, development of textile electrodes using conductive fiber have advanced in recent years, and have been made available centering on the sports and health fields. Textile electrodes are cloth-like biological electrodes incorporating conductive fiber, and are used with pressure fixation to skin using stretchable bands and the like. With respect to textile electrodes, pasteless types predominate which bring the electrode into direct contact with skin without use of electrolytic paste, or which are used in a state where moisture is contained in the cloth which composes the electrode.

With respect to measurement by means of such textile electrodes, in cases where the state of contact with skin is stably maintained, relatively satisfactory biological signals are obtained. However, in cases where the state of contact with skin is even slightly unstable, the resistance between skin and electrode fluctuates greatly, resulting in the problem that the reliability of measured waveforms declines due to artifacts such as distortion of recorded waveforms and immixture of hum noise.

With respect to a biological electrode of a second embodiment of the third aspect of the present invention described below, similar to the biological electrode of the first embodiment, downsizing of the electrode and contraction of the skin contact area are made possible by utilizing the conductivity of conductive polymer. Furthermore, this electrode which is composed of flexible fiber material imparts little irritation to skin when attached, and inhibits the occurrence of discomfort during attachment. Moreover, there is no need for close adhesion to skin by means of highly adhesive gel or tape or the like, unlike conventional biological electrodes. As the biological electrode of the second embodiment of the present invention has an excellent wear feeling, enables continuous use, and has an external appearance that causes no strangeness when attached, it can be preferentially used in applications involving textiles for medical or sports use.

Second Embodiment of the Third Aspect

Figure 24A:
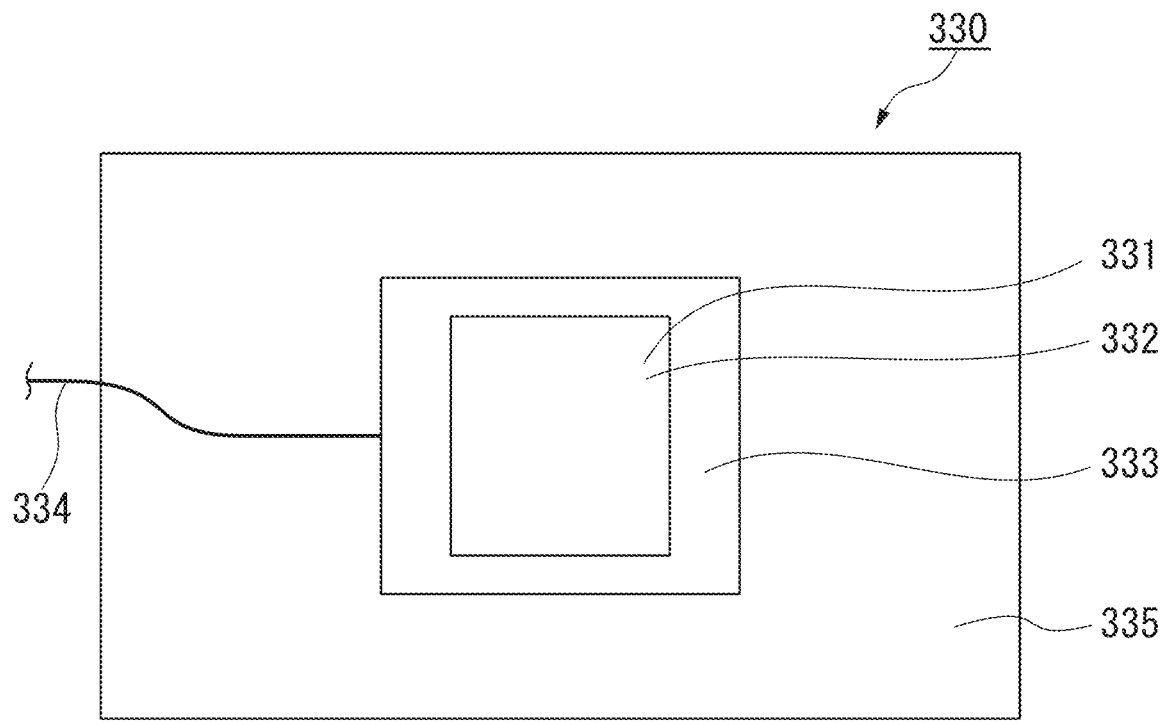
FIG. 24A is a plan view which shows a contact surface of an electrocardiogram electrode 330 with skin.
Figure 24B:
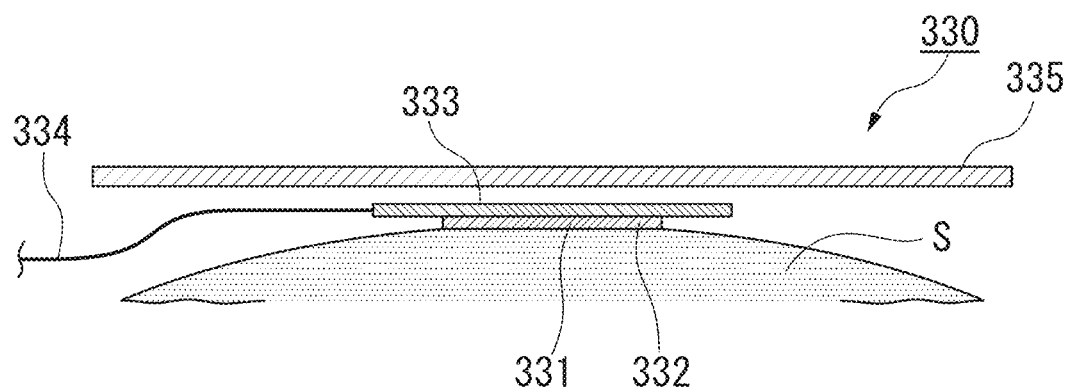
FIG. 24B is a side view which shows a condition where the aforementioned electrocardiogram electrode 330 is placed on a skin surface S.

A biological electrode 330 of the second embodiment is shown in FIG. 24A-24B. The biological electrode 330 is provided with a contact part (electrode surface) 332 in which multiple cord-like contacts 331 composed of conductive composite fiber are planarly arranged, and a sheet-like substrate 333 which supports the contact part 332. A configuration combining the contact part 332 and the substrate 333 is called an electrode pad. A signal cable 334 is provided which is electrically connected to each contact 331. Furthermore, a holder 335 composed of stretchable material is provided as a means for pressing the contact part 332 of the aforementioned electrode pad against skin S.

There no particular limitations on the form of the planar contact part 332 in which multiple contacts 331 composed of conductive composite fiber bundles are arranged, and the substrate 333, in so far as they enable to obtain surface contact between the contact part 332 and skin, and it is not necessarily tabular. In short, the contact part 332 or the substrate 333 may be formed in a curved, concave, or convex manner along a curved surface of skin. There is no need for the form of the electrode pad to be rigidly fixed, and it may flexibly change shape in conjunction with skin contact.

By using the sheet-like substrate 333, it is possible to ensure the planarity of the skin contact surface of the biological electrode, and also promote stable adhesion to skin. The material, size, and form of the aforementioned substrate may be selected at one's discretion. For example, as the substrate, one may cite a PVC (polyvinyl chloride) sheet of 0.2 mm thickness, or a silicone flat sheet (1 mm thickness). The material of the aforementioned substrate is not limited thereto, and a material is well suited for use that is a flexible film-like (sheet-like) material, that easily maintains the planarity of the substrate, and that has satisfactory adhesion with skin.

The contact part 332 (electrode pad) that contacts the skin is formed such that the contacts 331 composed of conductive composite fibers are arranged on the aforementioned substrate. It is also acceptable to provide a substrate surface with adhesion to skin by lightly imparting adhesive properties to one surface of the sheet-like substrate (the surface provided with the contact part 332). There are no particular limitations on the size of the sheet composing the substrate 333. For example, in the case of a square-shaped electrode for electrocardiogram use, one side may be set at about 30 mm (e.g., in a range from 5 mm to 75 mm).

Figure 25A:
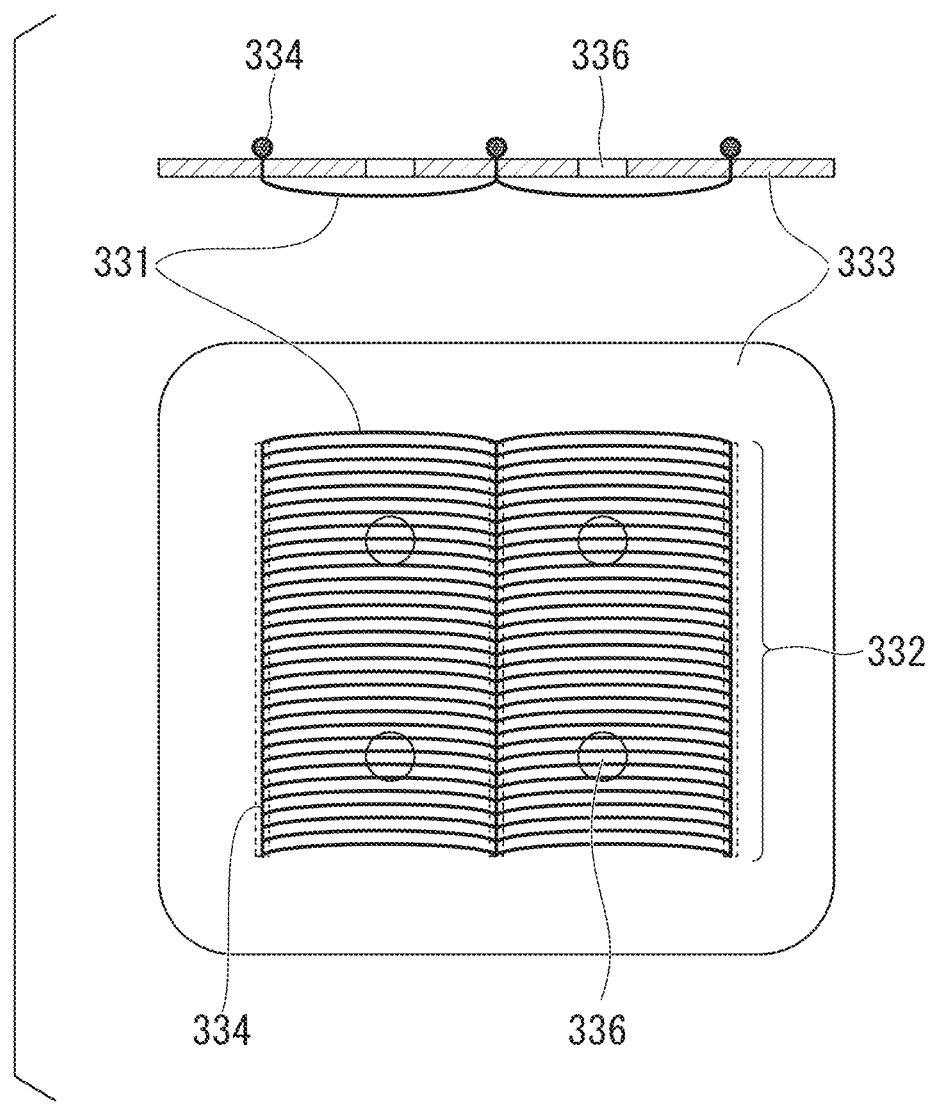
FIG. 25A shows examples of a side view and a front elevation (skin contact plane, i.e., surface) of an electrode pad.
Figure 25B:
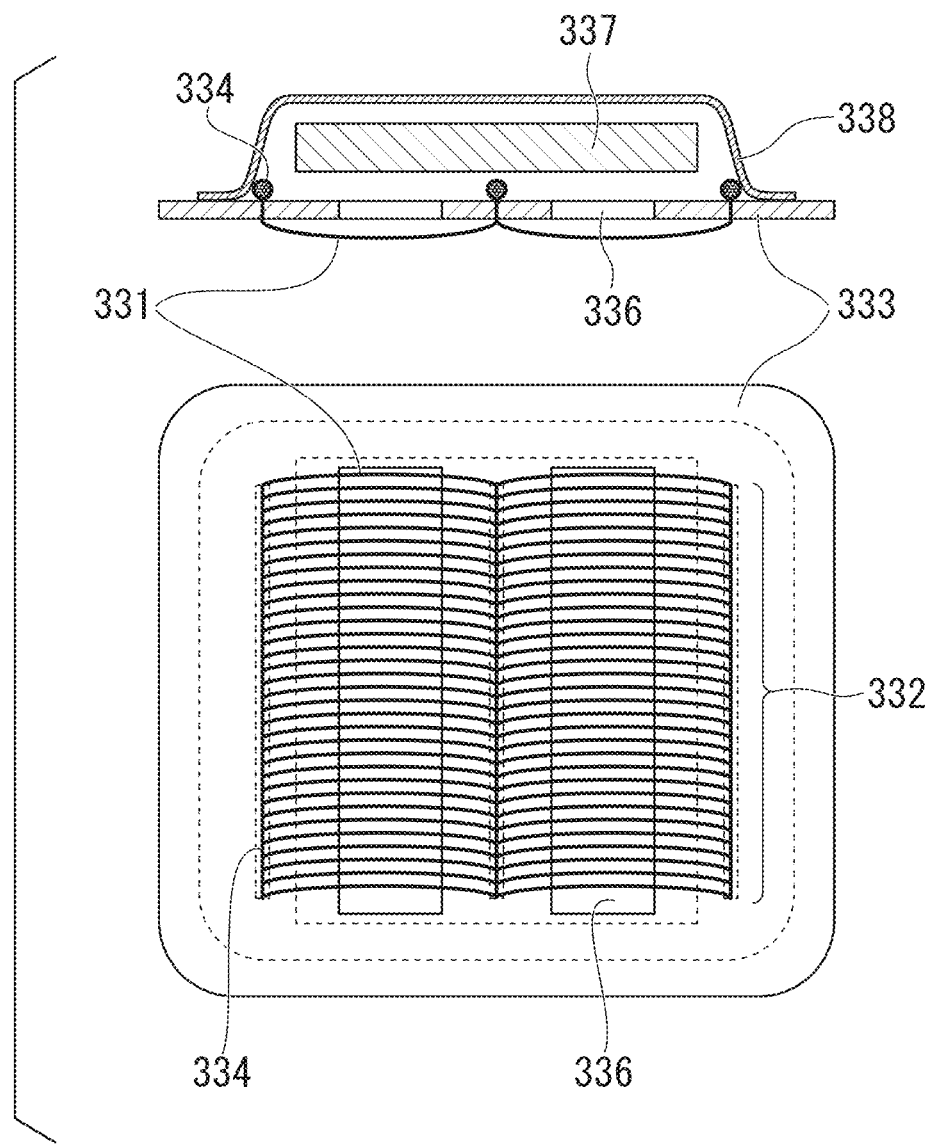
FIG. 25B shows other examples of a side view and a front elevation (skin contact plane, i.e., surface) of the aforementioned electrode pad.

A specific example of a biological electrode 330 is shown in FIG. 25A-25B. The upper level shows a side view, and the lower level shows a frontal view. The holder 335 is omitted from the drawings.

In the example of FIG. 25A-25B, multiple contacts 331 are arranged in parallel in the lateral direction on the page surface, and the two ends of each contact 331 are connected to the signal cables 334 disposed in the vertical direction on the page surface. The two ends of the contact 331 penetrate the substrate 333 to connect to the signal cables 334. In the illustrated example, with respect to the surfaces of the substrate 333 that is the base material, the signal cables 334 are disposed on the opposite surface (the rear surface) from the surface (front surface) on which the contacts 331 are arranged and fixed. With this configuration, the contacts 331 can be drawn to the substrate surface by the signal cables 334. The surface on which the signal cables 334 are disposed may be the front surface rather than the rear surface of the substrate 333

At overlapping positions of the contact 332 and the substrate 333, apertures 336 are provided in the substrate 333. The apertures 336 function as ventilation holes (aeration holes). That is, when the electrode pad including the contact part 332 and the substrate 333 presses against skin, vapor or perspiration from the skin can discharge to the exterior of the electrode pad from the apertures 336. There are no particular limitations on the form of the apertures 336, provided that it is a form that pierces the substrate 333, and allows passage of air, and any shape such as circular or rectangular is acceptable. The contacts 331 disposed on the front surface of the substrate 333 may be exposed to the rear surface of the substrate 333 through the apertures 336.

There are no particular limitations on the positions where the apertures 336 are disposed in the substrate 333, but are preferably disposed so that the multiple apertures 336 are mutually symmetrical relative to the center of the substrate 333. The multiple apertures 336 are also preferably provided at positions that overlap with the contact part 332. There are no particular limitations on the total aperture area of the apertures 336 provided in the substrate 333. Setting of a large aperture area that would impair the structural strength of the substrate 333 is preferably to be avoided, and ordinarily an aperture area is about 1-40% of the area of the substrate 333 is preferable. Selection of the aperture area is preferably made within the above range according to purpose, and, for example, 1-20%, 20-40%, or 10-30% is acceptable. Within the aforementioned range, the structural strength of the substrate 333 can be adequately maintained, aeration properties between the substrate 333 and the skin can be improved, and steaming of the skin can be mitigated. The total aperture area of the apertures 336 provided at positions overlapping the contact part 332 is preferably about 2-60% of the area of the contact part 332. Selection is preferably made within this range according to purpose, and for example, 2-40%, 40-60%, 10-30%, or 5-45% is acceptable. Within the aforementioned range, the structural strength of the contact part 332 can be adequately maintained, aeration properties between the contact part 332 and the skin can be improved, and steaming of the skin can be mitigated.

As shown in FIG. 25B, a humidity control pad 337 may be provided on the surface (rear surface) of the substrate 333 that is opposite the contact part 332. Vapor or perspiration that passes through the apertures 336 can be absorbed by the humidity control pad 337. There are no particular limitations on the material of the humidity control pad 337, provided that it is material having water absorbency.

A humidity control cover 338 may also be provided for purposes of covering or fixing the humidity control pad 337.

The humidity control pad 337 does not only absorb skin perspiration and the like, but can also be used for the purpose of supplying a humectant such as water or glycerol to the skin and the contacts, by impregnating the humidity control pad 337 in advance with a humectant such as water or glycerol. In FIG. 25A-25B, the contacts 331 disposed on the front surface of the substrate 333 may be exposed to the rear surface of the substrate 333 by the apertures 336, and the contacts 331 may contact the humidity control pad 337. By means of this contact, water and the like can be supplied to the contacts 331.

By providing the apertures 336 in the substrate 333, it is possible to respond to a variety of skin conditions from situations of copious perspiration and susceptibility to steaming such as in summertime, among young people, and during exercise, to situations of dryness such as in wintertime, among the elderly, and during repose. The apertures 336 free skin that is closed (covered) by the electrode pad, and are not only provided for the purpose of diffusing humidity, but may also be provided for the purpose of actively supplying moisture to skin. That is, removal of perspiration and adjustment of humidity can be achieved by providing a water absorbent pad (sponge or the like) 337 on the apertures 336. By including water, glycerol, or moisturizers in the aforementioned humidity control pad 337 in environments susceptible to dryness, the aforementioned ingredients can be supplied to the contacts 331 and the skin from the pad 337. For purposes of humidity control during dryness, the exterior of the aforementioned humidity control pad 337 is preferably covered with a cover of PVC or the like. As the conductive composite fibers composing the contacts 331 have moderate hygroscopic properties, and as moisture is transported and dispersed by capillary action in the minute fibers composing the contacts 331, smooth humidity regulation is possible in the periphery of the contacts 332 by establishment of the apertures 336 and the pad 337.

The size (area) of the apertures 336 can be suitably adjusted according to usage conditions such as room temperature, humidity, exercise, and presence or absence of fever. There are no particular limitations on the total area of an individual or multiple aperture(s) 336 provided in the substrate 333, provided that the structural strength of the substrate 333 can be suitably maintained. For example, adjustment of the total area can be conducted in a range from 0.1 to 50% relative to the area of the sheet-like substrate 333 composing the electrode pad. Selection of the total area is preferably conducted within the above range according to purpose, and, for example, 0.1-30%, 30-50%, 5-40%, 15-50%, 0.1-5%, and so on are acceptable.

A description of the conductive composite fibers composing the contacts 331 is identical to the description of the conductive composite fibers of the above-described first embodiment. Moreover, a description of the structure of the contacts 331 is identical to the description of the contacts of the above-described first embodiment.

There are no particular limitations on the density of the contacts 331 in the contact part 332, on the number of contacts 331 per unit area of the contact part 332, and on the area of the contact part 332, and these may be suitably adjusted according to application.

With respect to the density of the contacts 331 in the contact part 332 when, for example, contacts 331 (fiber bundles) with a diameter of 280 microns are arranged in parallel, 30 contacts would normally be used at an electrode width of 10 mm, but one is not limited thereto. For example, it is possible to conduct adjustment of the number within a range from 1 to 200.

More specifically, for example, with respect to a biological electrode for electrocardiogram measurement, when conductive composite fiber bundles (contacts in which composite fiber of PEDOT-PSS and silk is impregnated with glycerol) which are identical to those in Example 3-1 described below are arranged in parallel without gaps and fixed to a substrate for use, the contact area with skin (the area of the contact part 332) may be set at 1 cm×1 cm (100 mm$^2$), and can normally be set to 10-50,000 mm$^2$. In the case where the aforementioned biological electrode for electrocardiogram measurement is used as a skin surface electrode for electrical stimulation, the range of the contact area of the electrode can be set, for example, to 10-50,000 mm$^2$.

There are no particular limitations on the method of arrangement of the contacts 331 in the contact part 332, and it may be suitably adjusted according to application. For example, not only may multiple contacts 331 (conductive composite fiber bundles) be arranged in parallel without gaps, but it is also possible to adopt a configuration wherein multiple contacts 331 are laid in multiple layers, a configuration wherein multiple contacts 331 are formed into cloth-like form by weaving or knitting, and a towel-like configuration wherein multiple contacts 331 are napped on a fabric. A configuration in which multiple contacts 331 mutually overlap poses no problems for use, because the respective contacts 331 are in mutual contact, and are electrically connected (conductivity is obtained). It is also acceptable to adopt a configuration wherein the gaps between the multiple contacts 331 in the contact part 332 are widened, and the multiple contacts 331 are sparsely arranged. In such a configuration, the surface of the substrate 333 is exposed through the gaps in the contacts 331, thereby enabling the aforementioned exposed surface to directly contact skin from between the contacts 331. Consequently, by imparting adhesive properties to the aforementioned exposed surface of the substrate 333, it is possible to adjust the adhesive force of the electrode pad relative to skin, the current density, and the contact range between the contact part 332 of the electrode and the skin.

The aforementioned conductive composite fibers are maintained in a moderately moist (wet) state by impregnating the conductive composite fibers composing the contacts 331 with moisturizing ingredients such as glycerol, and by having moisture (perspiration) from the skin on which the biological electrode is set absorbed by the aforementioned conductive composite fibers. When the aforementioned conductive composite fibers are moderately moist, a light tackiness is produced in the aforementioned conductive composite fibers.

There are no particular limitations on the method for attaching the electrode pad of the biological electrode 330 to a skin surface, provided that it is a method enabling stable fixation of the biological electrode. For example, utilizing the aforementioned tackiness possessed by the conductive composite fibers, or the tackiness of the sheet-like substrate 333, it is possible to independently affix the electrode pad alone to the skin. When the contact part 332 in which the contacts 331 are arranged are brought into contact with a body surface (skin surface), the contacts 331 are quickly affixed to the skin surface, and conduction is obtained between the contacts 331 and the skin surface, enabling obtainment of biological signals. The biological signals are transmitted to an external device such as a biological amp through the signal cable 334 (metallic conductor wire) connected to the contacts 331.

Utilizing the tackiness possessed by the electrode pad in this manner, it is possible to fix (attach) the electrode pad alone to a skin surface. With this fixation method, the fixing force relative to skin is not high, because the electrode pad is affixed to the skin utilizing the weak adhesion of the substrate 333, and the adhesion produced by the wetness of the conductive composite fibers of the contacts 331. Therefore, there is a possibility that the electrode pad could be displaced or come off due to pulling of the signal cable 334 or significant body movement. Thus, with a view to stable retention of the electrode pad and prevention of displacement or separation, the holder 335 may be applied in order to press the electrode pad against the skin surface S.

There are no particular limitations on the configuration such as the form or size of the holder 335. For example, one may cite a method wherein, using a band-like stretchable fabric (drape) like that shown in FIG. 25A-25B, electrode pads 338 are attached to the skin surface S of a body B, and the stretchable holder 335 is wound so that it enwraps the torso circumference of the body B from above the electrode pads 338. With this configuration, the electrode pads 338 do not easily come off even when there is significant movement of the body B, and the electrode pads 338 can be more stably fixed.

Figure 26A:
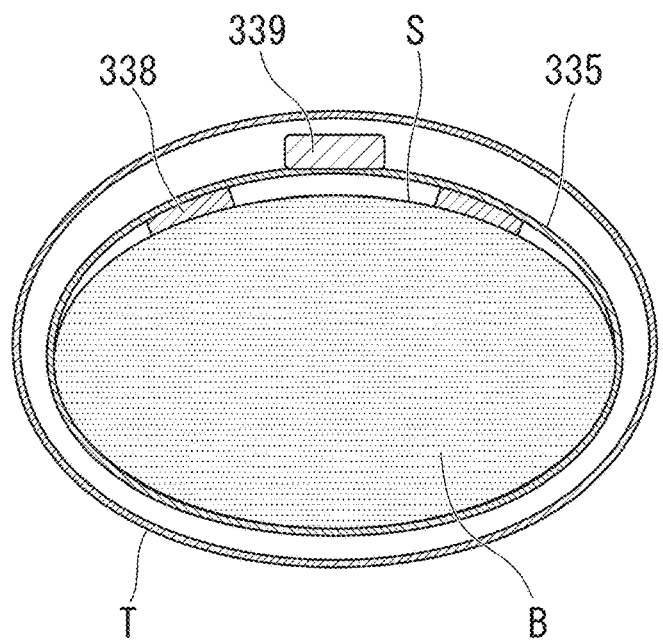
FIG. 26A is a cross-sectional view which shows disposition of a holder 335 and an electrode pad 338 relative to a torso B.
Figure 26B:
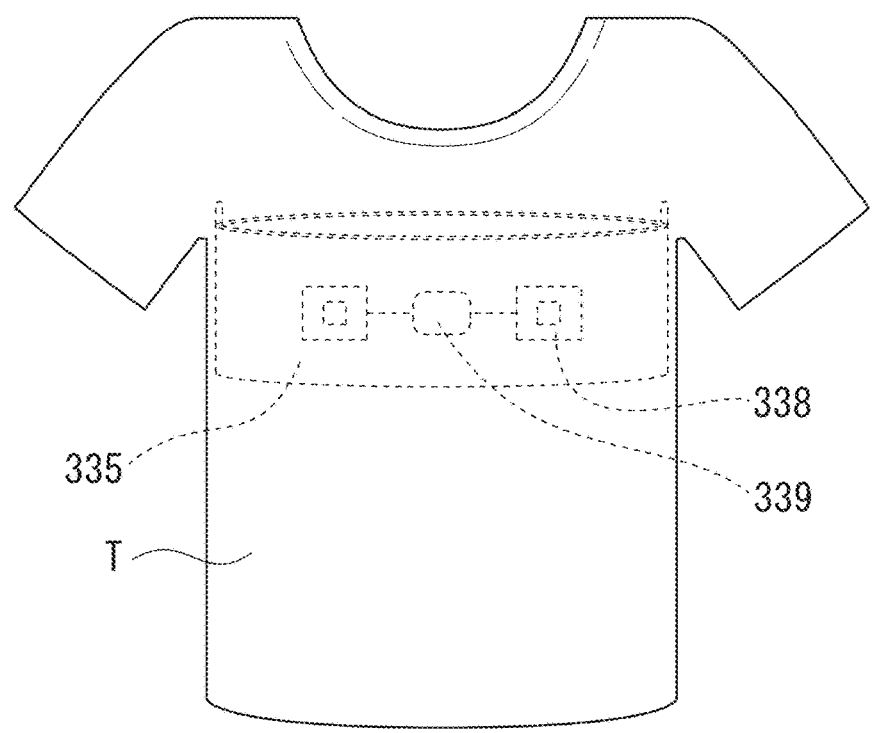
FIG. 26B is a front elevation of the aforementioned torso B.

For example, as shown in FIG. 26A-26B, the holder 335 can be set on the inside of an undershirt (shirt) T. The electrode pads 338 and a portion of the holder 335 are fastened to the inside of the undershirt T. The holder 335 and the electrode pads 338 are structurally independent, and the holder 335 is made so that it is capable of moving in the transverse direction over the electrode pads 338, i.e., capable of moving (capable of shifting) in a direction along the surface of the body B. Therefore, the holder 335 and the electrode pads 338 are preferably disposed so that they can be distanced from each other, and the holder 335 and the electrode pads 338 are preferably not completely fixed. Thus, the holder 335 and the electrode pads 338 are structurally independent, the contact sites of the holder 335 and the electrode pads 338 are not fixed, and the holder 335 is capable of sliding over the electrode pads 338 at the aforementioned contacts sites, whereby it is possible to inhibit the electrode pads 338 from coming off due to displacement of the body B and the undershirt T, the attenuation of biological signals, and the occurrence of noise associated with electrode displacement. Moreover, when necessary, the holder 335 can be proactively withdrawn from the body B, and the electrode pads 338 can be removed and/or replaced. The holder 335 can play the role of stably holding the electrode pads 338, and can also be utilized to hold accessories of the biological electrode (a cable, a connector, an amp 339, and so on).

There are no particular limitations on the base fabric (material) composing the holder 335. For example, among cloth, sheet, mesh, rubber band, and the like, use of a stretchable base fabric is preferable. Specifically, band-like two-way stretchable cloth or lycra (registered trademark) (general name: Spandex) (manufactured by Toray, Ltd.) can be used by stitching it to the inside of an undershirt at a width (longitudinal length) of 15 cm to conform to the height of the heart (see FIG. 25A-25B). This holder is well suited for use as, for example, the holder of an electrocardiogram electrode (for CC5 induction). In the case of CC5, a configuration can be adopted wherein the electrode pads 338 are set up on the left and right of the anterior chest, and these are covered by the electrode holder 335.

The holder 335 is not limited for the case where it is attached to the inside of an undershirt of the upper body as described above, and, for example, it may also be attached by being wound in a band-like manner around a limb, head, neck, or finger according to the application of the biological electrode 330. The material of the holder 335 is not limited to the aforementioned Spandex, and various types of cloth, sheet, mesh, band, and the like can be used provided that they are stretchable flat material (base fabric).

<<Effects Obtained by the Biological Electrodes of the First Embodiment and Second Embodiment of the Third Aspect of the Present Invention>>

Examples of the effects obtained by the materials and structures with which the biological electrodes of the respective embodiments are provided are cited as follows.

When the biological electrode pertaining to the present invention is attached to a measurement site, there is no need to use conductive gel (electrolytic gel) or conductive paste (electrolytic paste). By not using conductive gel or paste, the following effects (A)-(E) are obtained.

(A) Wear Feeling is Improved.

Occurrence of discomfort associated with attachment of the electrode to skin is inhibited. As the aforementioned gel or paste is not used, there is no need to seal the skin with liquid or gel, and the electrode can be attached in a state where the skin is exposed to the external air. That is, measurement can be conducted in a state where the cord-like electrode lightly contacts the skin, or in a state where a soft cloth-like electrode touches the skin.

(B) Trouble Caused by Electrolytic Paste is Avoided.

There is no risk of occurrence of contact defects or noise in the case where the electrolytic fluid leaks out or the moisture of the aforementioned gel or paste dries up.

(C) Electrical Properties of the Electrode are Improved.

Electrode resistance per unit area can be lowered to less than that of a conventional biological electrode. This is advantageous for measurement of weak signals such as brain waves or evoked potential. Moreover, as the electrode of the present invention has little capacitance, high-frequency transmission properties are excellent, and this is advantageous for recording biological signals containing high-frequency components such as brain waves and electrocardiograms.

(D) The Convenience of Use of the Electrode is High.

As the aforementioned paste or gel is not used, there is no need for an operation to remove the aforementioned paste or gel after measurement (after testing). For example, one can omit hair washing after brainwave measurement, which is necessary with use of conventional electrodes.

(E) Downsizing of the Electrode is Possible.

As electrode resistance per unit area is less than that of a conventional electrode, the electrode can have a smaller size, a lighter weight, and a higher density than a conventional biological electrode.

As a result of being provided with conductive composite fibers, the biological electrode of the present invention can obtain the following effects (F)-(K).

(F) Stability of Attachment is Improved.

Stable attachment of the electrode is possible by light pressure or weakly adhesive material. There is no need for a powerful adhesive agent, or for strong pressure fixation by band, headgear and the like, as with conventional biological electrodes.

(G) Low-Noise Signals are Obtained.

Due to the properties of the conductive composite fibers including adhesion, flexibility, thinness, and light weight, there is little unnecessary vibration of the electrode during body movement when the electrode wearer (subject) moves, mitigating noise.

(H) A Natural External Appearance is Obtained.

Particularly in brainwave electrode applications, the electrodes do not stand out even when attached, due to downsizing and flattening of the electrodes, and a design that conceals the electrodes under head hair. That is, brainwave measurement is possible at all times during daily life.

(I) Skin Steaming Due to Attachment of Biological Electrodes Over Long Periods can be Mitigated.

Generally, when electrodes are continuously attached over long periods, skin steaming tends to occur due to perspiration of the skin. However, in the case where the biological electrode of the present invention uses hydrophilic conductive composite fiber in the electrode material, and provides apertures for aeration in the substrate as described above, skin steaming when use of the electrode is conducted over long periods can be further mitigated.

(J) The Range of Application of the Biological Electrode can be Expanded.

The overall form (basic form) of the biological electrode can be fashioned into a thin planar shape (cloth shape) or linear shape (cord shape). As the electrode is lighter in weight, flatter, and more flexible than conventional electrodes, it is possible to fabricate electrodes with a linear shape that is thinner than a cord shape. In addition, the wear feeling is also comfortable. Due to these properties, the biological electrode of the present invention can be applied as a wearable electrode, and its range of application can be expanded.

(K) Measurement can be Conducted with a Stability that is Equal or Superior to that of Conventional Biological Electrodes.

Even when used without electrolytic paste (pasteless), the biological electrode of the present invention is able to overcome the immixture of noise and the instability of measured signals that are drawbacks of conventional pasteless electrodes. That is, it is possible to obtain a stability of measured signals that is equal or superior to that of conventional biological electrodes for medical treatment that use electrolytic paste.

A detailed description of conductive polymer fibers is given below that can be used as conductive composite fibers composing the biological electrode of the present invention. However, the aforementioned conductive composite fibers are not limited to these conductive polymer fibers.

Regarding the Fourth Aspect

The fourth aspect of the present invention relates to an implantable electrode and a device for measuring biological signals. More specifically, the present invention relates to an implantable biological electrode which uses composite material of conductive polymer and fibers (hereinafter "conductive composite fibers"), and a biological signal measurement device provided with the biological electrode.

Embodiments of the fourth aspect of the present invention are described below with reference to drawings, but the present invention is not limited by the pertinent embodiments.

As stated above, PEDOT-PSS which is a known conductive polymer gelatinizes in biological tissue due to its high water absorbency, greatly reducing its mechanical strength. Consequently, it is difficult to set PEDOT-PSS that is worked into a needle shape or rod shape within a living body alone. Even supposing that it were possible to implant PEDOT-PSS in biological tissue, there is the problem that the wire connection part of the electrode that is composed with PEDOT-PSS alone and the metallic conductor wire (cable) that connects to an external device is susceptible to embrittlement and breakage (disconnection).

With the fourth aspect of the present invention, conductive composite fibers compounded from conductive polymer and fibers are used as the implantable electrode. Accordingly the problems of dissolution of the electrode itself, and embrittlement of the wire connection of the conductive polymer and the metallic conductor wire, which is caused by moisture absorption by the conductive polymer, can be solved.

First Embodiment of the Fourth Aspect

Figure 29A:
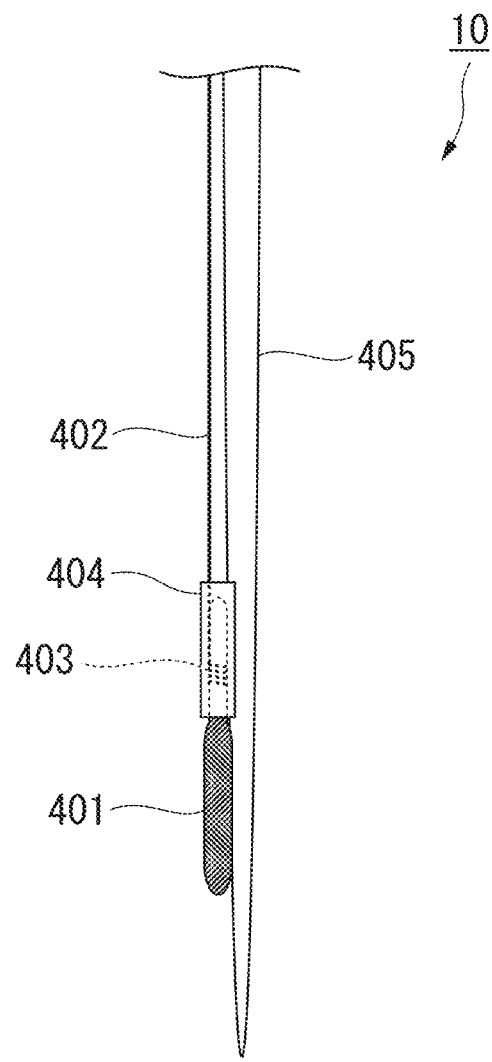
FIG. 29A is a side view of a first embodiment of the implantable electrode of the fourth aspect of the present invention.
Figure 29B:
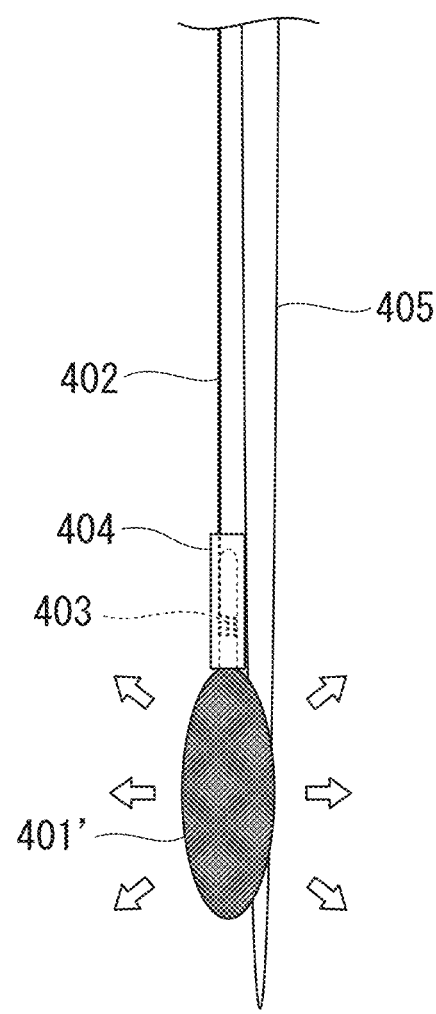
FIG. 29B is a side view which shows a condition where the conductive composite fiber bundle shown in FIG. 29A has swelled due to absorb water.
Figure 29C:
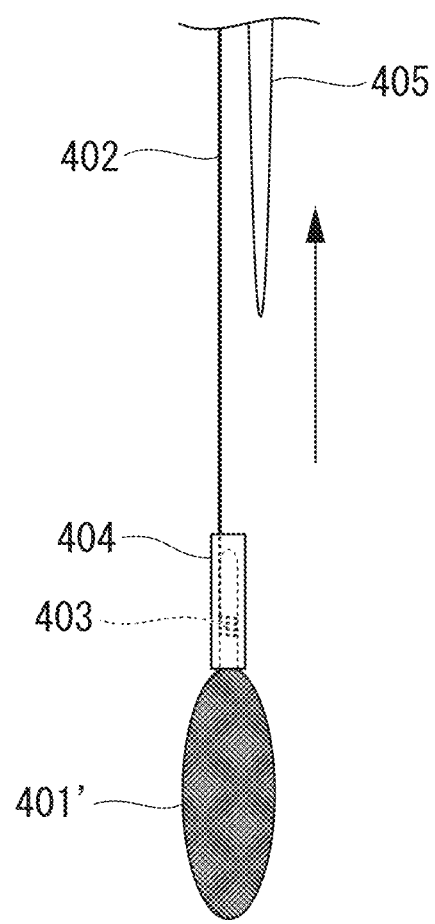
FIG. 29C is a side view which shows a condition where a needle is withdrawn from the aforementioned swollen conductive composite fiber bundle.

An implantable electrode 410 of a first embodiment of the fourth aspect of the present invention shown in FIG. 29A-29C is provided with a conductive composite fiber bundle 401 which is formed into a rod shape (needle shape) in which conductive composite fibers containing conductive polymer are multiply bundled. A metallic conductor wire 402 is wound around a portion of the conductive composite fiber bundle 401, forming a wire connection part 403. The wire connection part 403 is coated by a polymer 404 (resin) that is insulating and water resistant. Either before or after moisture absorption, the conductive composite fiber bundle 401 has better mechanical strength than a conductor of conductive polymer alone that is molded into a rod shape of the same diameter. Consequently, it is possible to prevent breakage of the conductive composite fiber bundle 401 when it is implanted into biological tissue, and dissolution of the conductive composite fiber bundle 401 in biological tissue after implantation.

The conductive composite fiber bundle 401 is preferably in a dry state prior to use. As the conductive composite fiber bundle 401 in a dry state has high mechanical strength, and is contracted compared to when wet, it has a relatively small volume. Therefore, by using the conductive composite fiber bundle 401 in a dry contracted state, its invasiveness can be mitigated during insertion into biological tissue.

(Conductive Composite Fibers)

As the conductive composite fibers composing the conductive composite fiber bundle 401, composite fibers of conductive polymer and known fiber material may be applied. There are no particular limitations on the compounding configuration (method). For example, a configuration is acceptable wherein the conductive polymer is coated onto a surface of the aforementioned fiber material that is thread-shaped (cord-shaped), a configuration is acceptable wherein the aforementioned fiber material that is thread-shaped is impregnated with the conductive polymer, and a configuration is acceptable wherein thread-shaped conductive polymer and the aforementioned fiber material that is thread-shaped are intertwined or spun together. The fiber described in the first embodiment of the present invention may be preferentially used.

There are no particular limitations on the type of the aforementioned conductive polymer, and known conductive polymer may be applied. For example, in addition to the aforementioned PEDOT-PSS, hydrophilic conductive polymer such as PEDOT-S(poly(4-(2,3-dihydrothieno[3,4-b][1,4]dioxin-2yl-methoxy-1-butanesulfonic acid, potassium salt) may be cited. By using composite fiber containing hydrophilic conductive polymer as a material of the conductive composite fiber bundle 1, adhesive properties (tackiness), which can adhere to a needle 405, can be easily imparted by the conductive composite fiber bundle 401 itself.

As the fiber material, for example, known fiber material may be applied such as silk, cotton, hemp, rayon, and chemical fiber. Of these, silk is optimal. When silk is used, the strength and hydrophilicity of the aforementioned composite fiber can be enhanced. Moreover, silk is preferable, because it has almost no toxicity relative to biological tissue, inhibits arousal of inflammation due to immune reaction, and has excellent compatibility with biological tissue.

There are no particular limitations on the type of the aforementioned conductive polymer that is combined with silk, but hydrophilic conductive polymer such as the aforementioned PEDOT-PSS or PEDOT-S is preferable.

There are no particular limitations on the length and diameter of the conductive composite fiber composing the implantable electrode of the present invention, and these may be suitably adjusted according to the length and diameter of the fiber material that is compounded. There are no particular limitations on the length and size of the conductive composite fiber bundle composed by intertwining and/or bonding of multiple conductive composite fibers, and these may be suitably adjusted according to purpose or application. For example, diameter within a range of 0.01 μm-5 mm is acceptable, and length within a range of 0.1 μm-1 m is acceptable. As another example, diameter within a range of 0.1 μm-1 mm is also acceptable, and length within a range of 0.1 μm-50 cm is also acceptable.

To cite a specific case, for example, the diameter of the rod-shaped conductive composite fiber bundle 401 shown in FIG. 29A-29C may be set at 0.1 μm-500 μm, and its length may be set at 1 μm-10 mm. The thickness of the coil-shaped conductive composite fiber bundle 401 shown in FIG. 31A-31C may, for example, be set at 10 μm-500 μm, and its length may be set at 100 μm-50 cm. Now, the aforementioned diameter and length are diameter and total extendable length in a state where the conductive composite fiber bundle 401 wound in a coil shape is stretched out. The external diameter of the coil in a state where it is wound in the coil shape shown in FIG. 31A-31C may be set, for example, at 10 μm-5 mm, and length of the coil in the direction of the central axis of the aforementioned coil may be set, for example, at 100 μm-50 mm. In addition, the diameter of the conductive composite fiber bundle 401 connected to the surgical thread shown in FIG. 32A-32D may be set, for example, at 0.1 μm-500 μm, and its length may be set at 1 μm-10 cm.

Figure 33A:
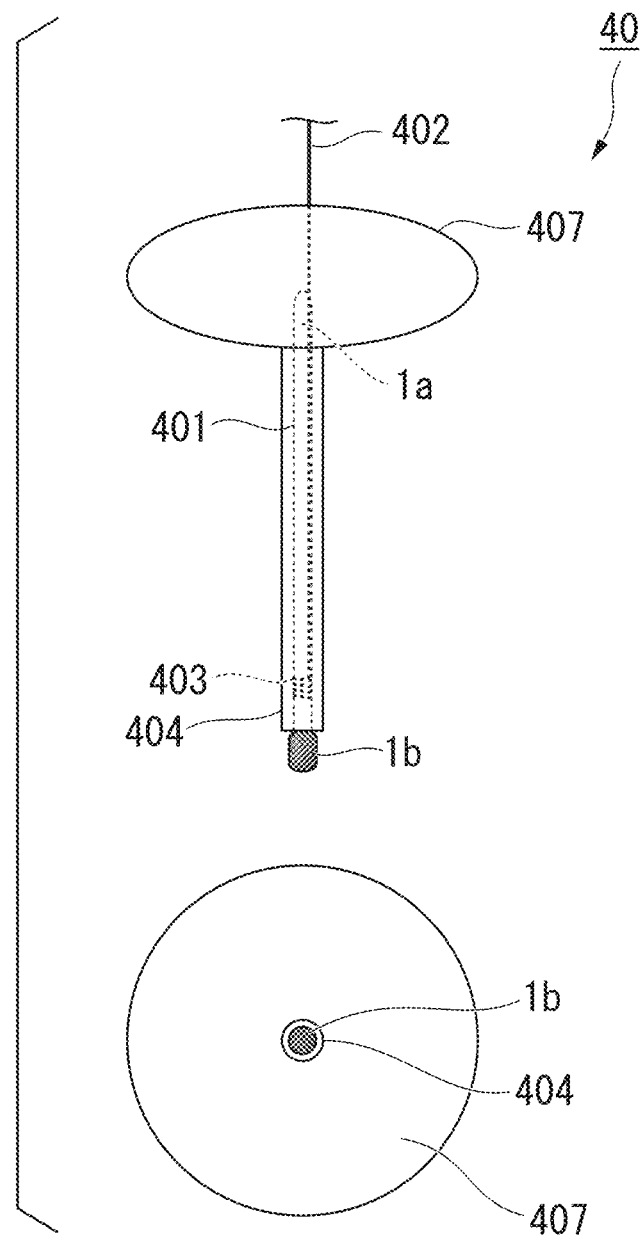
FIG. 33A is a side view and a bottom view of an implantable electrode provided with a flow path, and is a fourth embodiment provided with a reservoir.
Figure 33B:
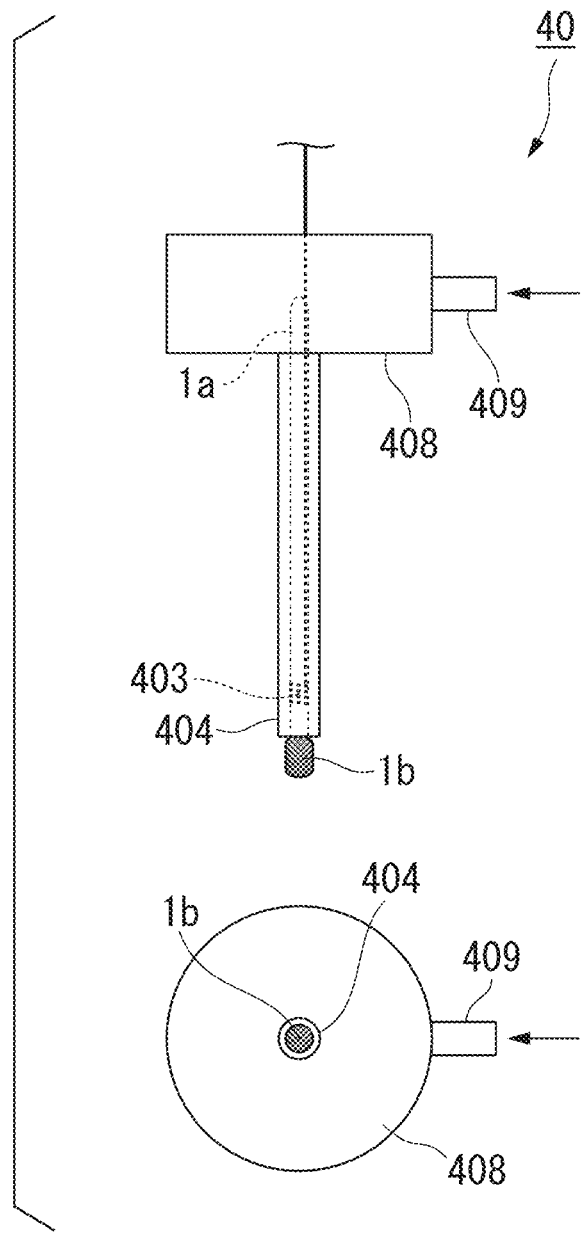
FIG. 33B is a fourth embodiment provided with a chamber and a tube connector.

The diameter of the conductive composite fiber bundle 401 composing the core part shown in FIG. 33B may be set, for example, at 10 μm-10 mm, and its length may be set, for example, at 10 μm-50 cm.

With respect to the conductive composite fiber composing the implantable electrodes of the respective embodiments of the present invention, the conductive polymer fiber described in further detail below may be applied.

(Bonding of Needle and Conductive Composite Fiber Bundle)

The conductive composite fiber bundle 401 of the first embodiment of the fourth aspect is bonded to the distal end of the needle 405 (guide needle).

When the conductive composite fiber bundle 401 is wetted with water or alcohol or the like, the conductive polymer in its surface has adhesiveness (tacky), and is fixed by contracting when it is dried again. Utilizing these properties, it is possible to bond (fix) the conductive composite fiber bundle 401 to the distal end of the needle 405 (FIG. 29A). When the implantable electrode 410 having this configuration is inserted into biological tissue, the conductive composite fiber bundle 401 absorbs body fluid (extracellular fluid or cerebrospinal fluid or the like), and swells (FIG. 29B). Furthermore, as the bonding force (fixing force) of the swollen conductive composite fiber bundle 401 and the needle 405 decreases, it is possible to withdraw the needle 405 while the conductive composite fiber bundle 401 remains inside the biological tissue (FIG. 29C). The conductive composite fiber bundle 401 that is set inside biological tissue is connected to an external device via the conductor wire 402 (metallic conductor wire 402), and receiving and transmission of signals (electrical signals or electrical stimulation) are preferable.

There are no particular limitations on the constituent material of the needle 405, and one may cite, for example, metal such as gold, platinum, and copper, carbon or resin (plastic), and the like.

The conductor wire 402 is preferably wire material capable of electrical conduction with respect to the conductive composite fiber bundle and the external device. There are no particular limitations on the constituent material of the conductor wire 402, and one may apply, for example, metal, silicon, carbon, and so on. There are no particular limitations on the type of the aforementioned metal, and metal used in conventional electric wire is acceptable. As the electric wire 402 that is implanted in biological tissue prevents pickup of electrical noise, and functions stably over long periods, the electric wire 402 is preferably coated with a polymer having insulating and water resistant properties. There are no particular limitations on the type of the aforementioned polymer, and the below-described water resistant polymer that coats the conductive composite fiber bundle of the fourth embodiment of the present invention may be applied. There are no particular limitations on the diameter and length of the electric wire 402, and these may be suitably adjusted according to application.

As the method of bonding the conductive composite fiber bundle 401 to the needle 405, in addition to the method of utilizing the above-described adhesiveness of conductive polymer, wherein the adhesiveness causes when it is wet, it is also acceptable to conduct bonding via hydrophilic adhesive material (an adhesive agent). There are no particular limitations on the aforementioned adhesive material, but material is preferable which can bond (demonstrate adhesion with respect to) the conductive composite fiber bundle 1 and the needle 5 in a dry state, and which decreases in bonding force (adhesive force) due to moisture absorption. For example, one may cite material containing PEG (polyethylene glycol), PEDOT-PSS, polylactic acid, sorbitol, fibrin glue, starch glue, and so on.

There are no particular limitations on the type of the aforementioned PEG, and one may use, for example, a relatively high polymer PEG which is solid at a temperature between room temperature (e.g., 20° C.) and at body temperature (e.g., 40° C.), and which becomes liquid when heated. After applying the PEG, that has been heated and dissolved, to the needle, and subsequently bringing the conductive composite fiber bundle into contact with the needle, the PEG is solidified by returning to room temperature, thereby enabling bonding of the needle and the fiber bundle. When this structure is placed in an environment where body fluid such as within tissue exists, the PEG gradually dissolves, enabling the conductive composite fiber bundle to naturally separate from the needle.

As a method for bonding the conductive composite fiber bundle 401 to the needle 405, it is also acceptable to indirectly bond the conductive composite fiber bundle 401 and the needle 405 via the aforementioned adhesive material that is applied to the polymer 404 that coats the wire connection part 403.

(Protection of the Wire Connection Part)

The wire connection part 403 is coated by the polymer 404. As the conductive composite fiber bundle 401 composing the wire connection part 403 is coated by the polymer 404 in the biological tissue, there occurs hardly any swelling or mechanical strength reduction due to moisture absorption. Moreover, as the mechanical strength of the conductive composite fiber bundle 401 is increased by its compounding with the fiber material, there is no breakage (disconnection) of the wire connection between the conductive composite fiber bundle 401 and the metallic wire connection 403 even after moisture absorption, and electrical connection can be fully maintained.

There no particular limitations on the method for connecting the metallic conductor wire 402 to the conductive composite fiber bundle 401 in the wire connection part 403, and, for example, one may cite a method involving bonding by winding, ligature, caulking, or an adhesive agent (silver paste, silver epoxy, and the like). There are no particular limitations on the type of the polymer 404 that coats the wire connection part 403, and one may cite, for example, silicone, PTFE (polytetrafluoroethylene), PVC (polyvinyl chloride), and so on. By coating the wire connection part 403 with the polymer 404, electrical short circuits can be prevented, and the wire connection part 403 can be protected.

(Implantation of the Electrode into the Body)

As a method for implanting the implantable electrode 410 of the first embodiment of the fourth aspect within biological tissue, one may cite, for example, a method wherein a manipulator capable of high-speed operation is used to insert the needle 405 at high speed (in a short time) into a living body. The needle 405 leads the way in penetrating to a prescribed position within the body, introducing both the conductive composite fiber bundle 401 bonded to the needle 405 and the connected metallic conductor wire 402 to the prescribed position within the body. This insertion is completed at high speed, and is preferably completed before the start of swelling of the conductive composite fiber bundle 401 in the body. There are no particular limitations on the insertion speed, and it may be conducted, for example, at 100-1000 mm/sec. As a specific example, using an electrically conducting actuator capable of high-speed operation, insertion can be conducted at a speed of 10-20 msec so that the conductive composite fiber bundle 401 of the implantable electrode 410 is implanted to a depth of 2 mm below the cerebral cortex of an animal. Subsequently, the conductive composite fiber bundle 401 swells due to body fluid, and the aforementioned adhesive material bonding the conductive composite fiber bundle 401 and the needle 405 dissolves, enabling the needle 405 alone to be withdrawn at the stage where the bonding force has weakened. The conductive composite fiber bundle 401 implanted in the biological tissue swells, closely adhering to the surrounding biological tissue.

(Implantation of Multiple Electrodes)

Figure 30A:
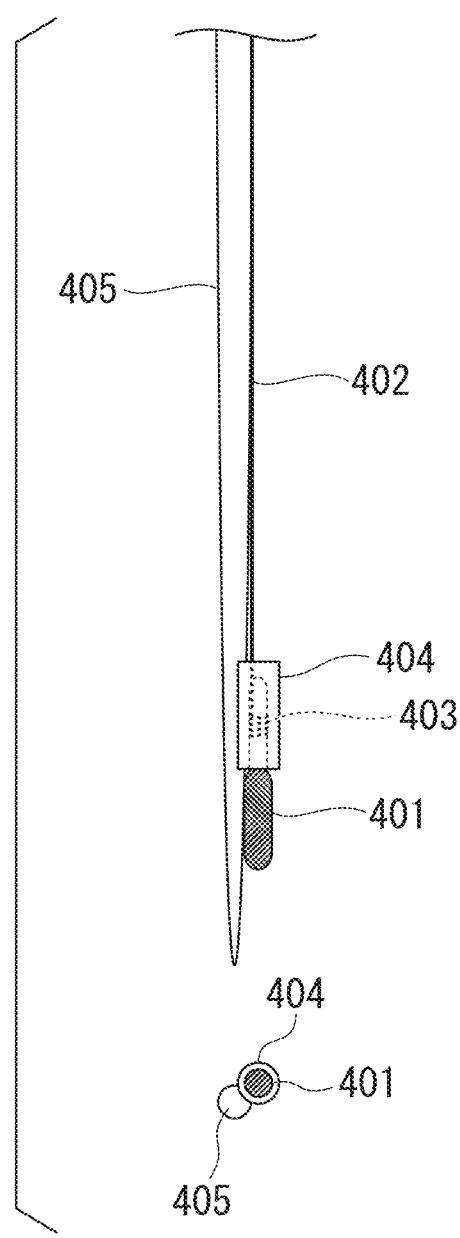
FIG. 30A consists of a side view and a bottom view which show an example of the electrode of the fourth aspect of the present invention, wherein a guide needle is provided with one conductive composite fiber bundle.
Figure 30B:
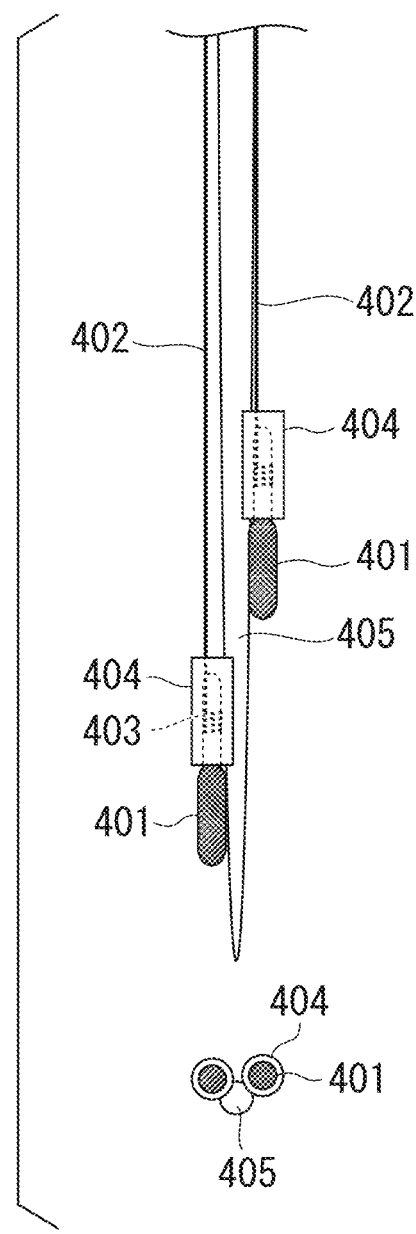
FIG. 30B consists of a side view and a bottom view which show an example of the electrode of the fourth aspect of the present invention, wherein a guide needle is provided with two conductive composite fiber bundles.
Figure 30C:
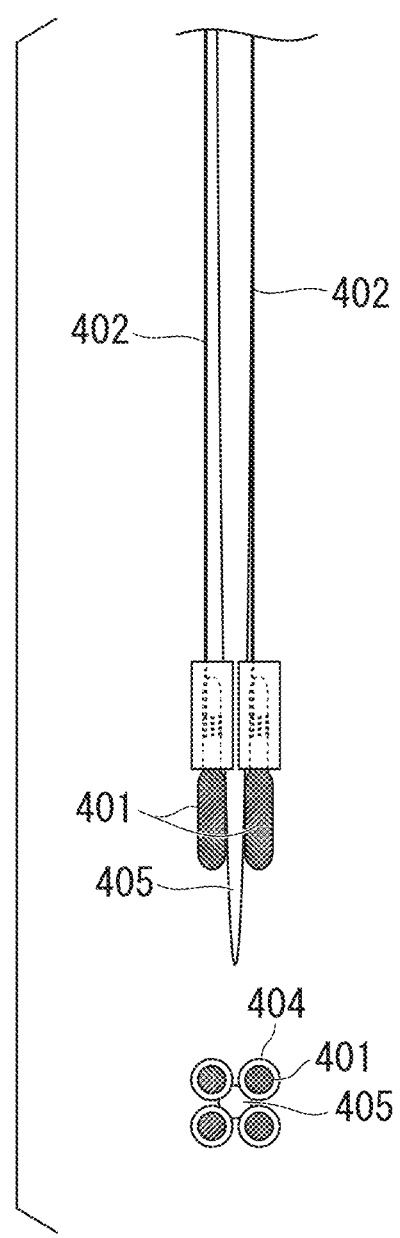
FIG. 30C consists of a side view and a bottom view which show an example of the electrode of the fourth aspect of the present invention, wherein a guide needle is provided with four conductive composite fiber bundles.

The implantable electrode 410 of the first embodiment may be provided with a single conductive composite fiber bundle 401 at the distal end of the needle 405 as shown in FIG. 30A, or it may be provided with multiple conductive composite fiber bundles 401 at the needle 405 as shown in FIG. 30B-30C.

In the configuration of FIG. 30B, the heights of the bonding sites of the two conductive composite fiber bundles 401 on the needle 405 are staggered (their positions in the lengthwise direction of the needle 405 are changed). With this configuration, the respective conductive composite fiber bundles 401 can be implanted at respectively different heights (depths) when inserted into the body, and can function as respectively independent electrodes (2ch electrode). In the configuration example of FIG. 30B, the conductive composite fiber bundles 401 are fixed to the two sides sandwiching the needle 405 when viewed from the side and from the bottom, but the two electrodes may also be fixed to one side of the needle 405. In such a case, when viewed from the bottom surface, the two conductive composite fiber bundles 401 would be observed overlapping in the depthward direction (in the height direction). That is, the cross-sectional area would be reduced. When fixed in this manner, the invasiveness inflicted on biological tissue when inserted into the body can be further mitigated.

In the configuration of FIG. 30C, the heights of the bonding sites of the four conductive composite fiber bundles 401 on the needle 405 are identical, and the four conductive composite fiber bundles 401 are disposed so as to surround the perimeter of the needle 405. In this case, the four conductive composite fiber bundles 401 (4ch electrode) can be implanted in the biological tissue centering on the position where the needle 405 is inserted.

Second Embodiment of the Fourth Aspect

Figure 31A:
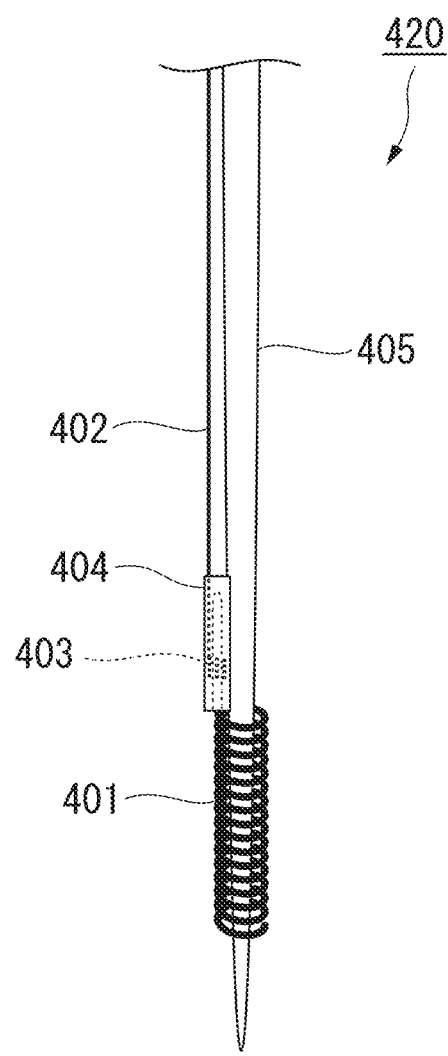
FIG. 31A is a side view of a second embodiment of the implantable electrode of the fourth aspect of the present invention.
Figure 31B:
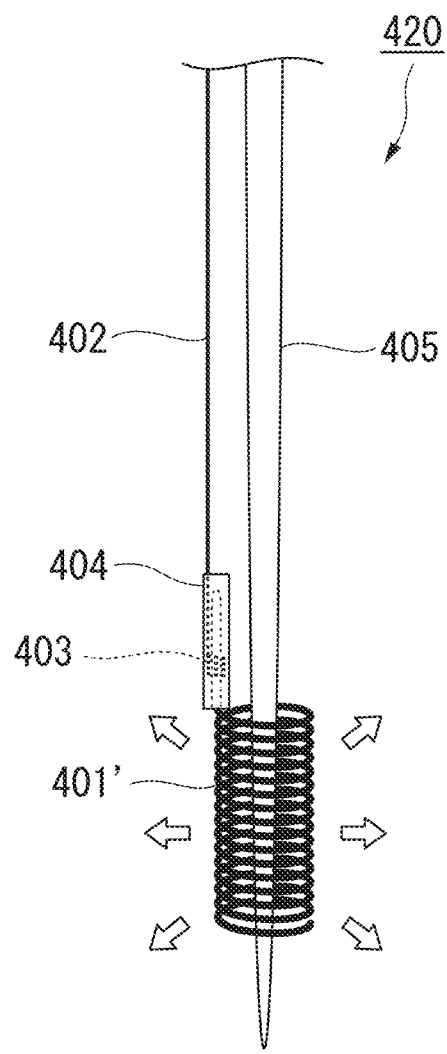
FIG. 31B is a side view which shows a condition where a conductive composite fiber bundle of the aforementioned electrode has swollen due to moisture absorption.
Figure 31C:
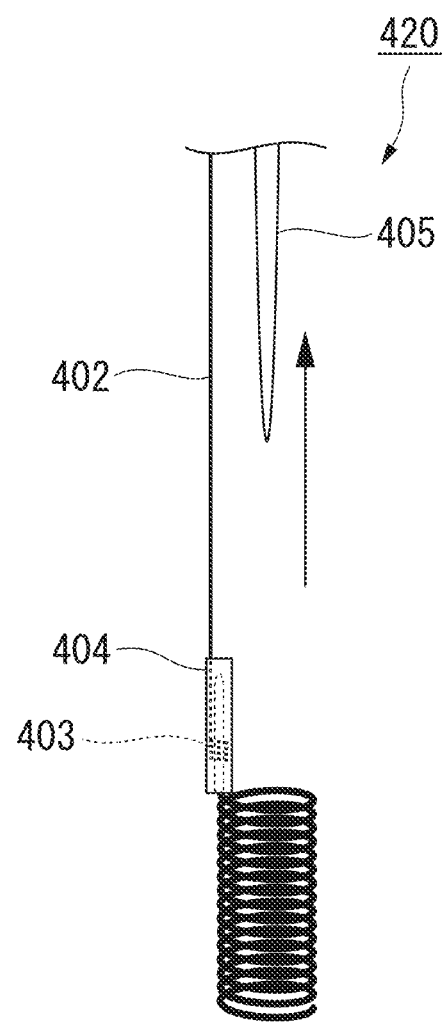
FIG. 31C is a side view which shows a condition where a needle is withdrawn from the swollen conductive composite fiber bundle of the aforementioned electrode.

An implantable electrode 420 of the second embodiment of the fourth aspect of the present invention shown in FIG. 31A-31C is identical to the first embodiment, except that the conductive composite fiber bundle 401 is wound around the distal end of the needle 405 in a coil shape. In FIG. 31A-31C, the same code numbers are assigned to components identical to the first embodiment of the fourth aspect.

The coil-shaped conductive composite fiber bundle 401 may be bonded to the distal end of the needle 405, or it may simply be wound around it. As the coil-shaped conductive composite fiber bundle 401 is firmly wound around the distal end of the needle 405, when insertion into biological tissue is conducted in the distal direction of the needle 405, the conductive composite fiber bundle 401 is prevented from falling off the needle 405 (FIG. 31A). Moreover, as the outer diameter of the coil (the diameter of a circle drawn by rotation of the coil) is small when it is dry and contracted, invasiveness relative to the biological tissue is mitigated. The implantable electrode 420 inserted into the biological tissue swells due to absorption of body fluid by the conductive composite fiber bundle 1, becoming a swollen fiber bundle 401' (FIG. 31B), i.e., the coil spontaneously expands with enlargement of its external diameter, resulting in close adhesion of the conductive composite fiber bundle 401 and the biological tissue. As the bonding force of the conductive composite fiber bundle 401 and the needle 405 weakens due to moisture absorption, the needle 405 can be withdrawn while the conductive composite fiber bundle 401 remains in the biological tissue (FIG. 31C).

The implantable electrode 420 of the second embodiment having the coil-shaped conductive composite fiber bundle 401 is suited to cases where atrophia or dead space could form in biological tissue due to implantation of the electrode (the conductive composite fiber bundle 401), or cases where the cells or nerve fibers subject to measurement are scattered within the biological tissue.

Third Embodiment of the Fourth Aspect

An implantable electrode 430 of a third embodiment of the fourth aspect of the present invention is shown in FIG. 32A-32D. The metallic conductor wire 402 is connected to one end of the conductive composite fiber bundle 401, and a surgical nylon monofilament thread 406 is bonded to the other end by the above-described method. A curved needle 405 for surgical stitching is attached to the nylon thread 406.

Figure 32A:
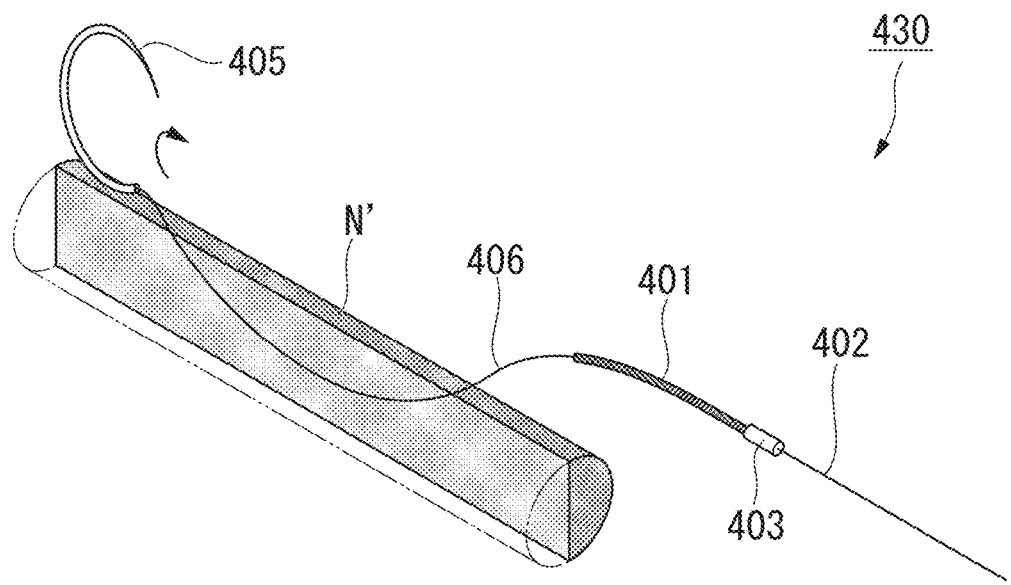
FIG. 32A is a schematic view which shows a condition where a third embodiment of the implantable electrode of the fourth aspect of the present invention is introduced into a nerve cord N'.
Figure 32B:
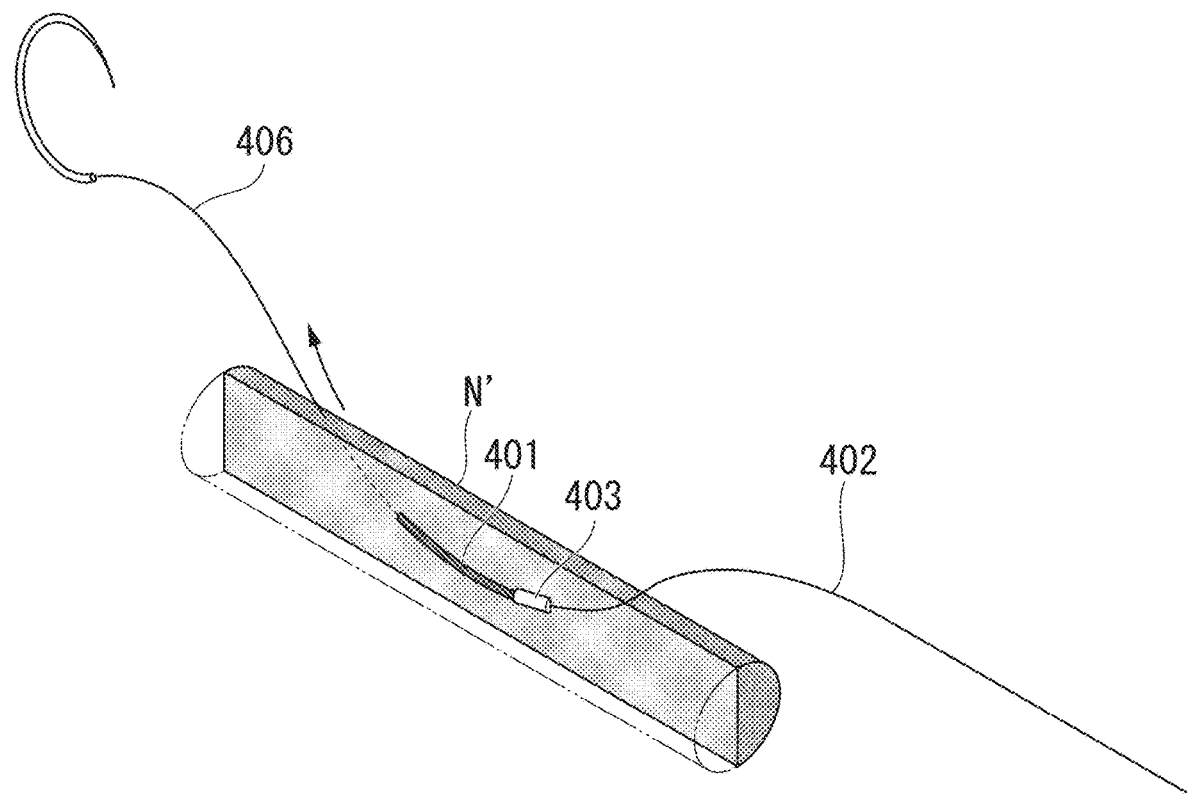
FIG. 32B is a schematic view which shows a condition where a third embodiment of the implantable electrode is introduced into a nerve cord N'.
Figure 32C:
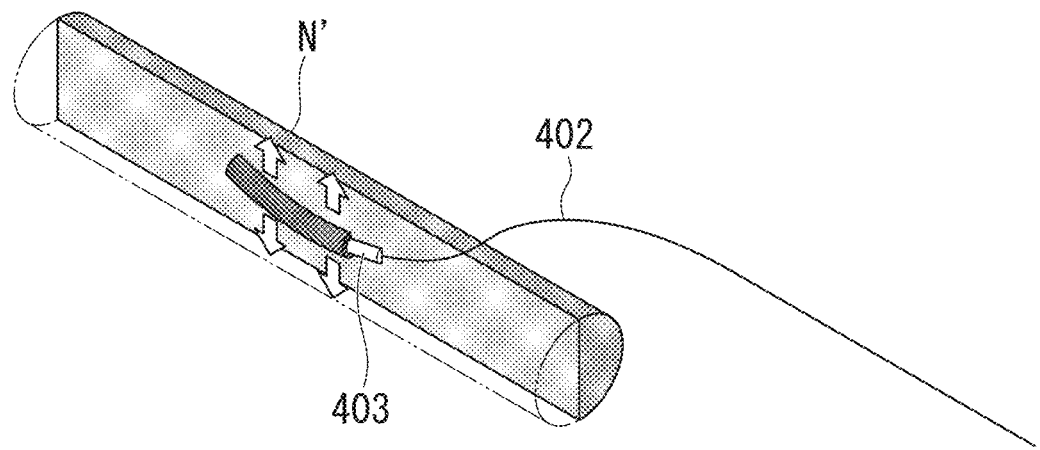
FIG. 32C is a schematic view which shows a condition where a third embodiment of the implantable electrode is introduced into a nerve cord N'.
Figure 32D:
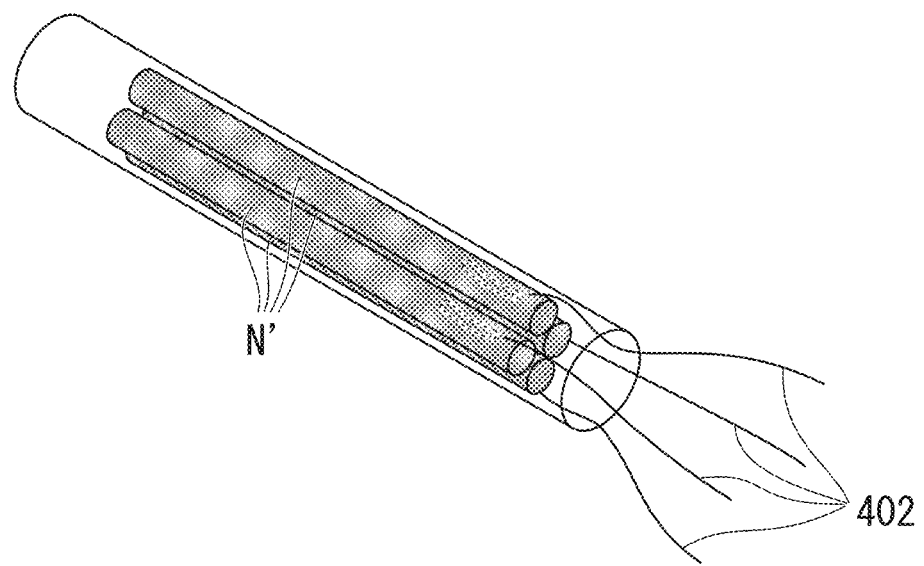
FIG. 32D is a schematic view which shows a condition where a third embodiment of the implantable electrode is introduced into a nerve cord N'.

A method is exemplified in which the implantable electrode 430 is placed within a nerve cord (bundle). According to a microsurgical operation technique using neurovascular suturing, the needle 405 is made to pass through (pierce) a nerve cord N' (FIG. 32A), and the nylon thread 406 is pulled upward in a procedure that sutures the nerve cord N', whereby the conductive composite fiber bundle 401 that is pulled by the nylon thread 406 is introduced into the nerve cord N' (FIG. 32B). Subsequently, as a result of body fluid absorption by the conductive composite fiber bundle 401 at a prescribed position within the nerve cord N', the nylon thread 406 detaches from the conductive composite fiber bundle 401, and can be removed to the outside of the nerve cord N'. The conductive composite fiber bundle 401 implanted within the nerve cord N' swells due to moisture absorption, closely adhering to the interior of the nerve cord N' (FIG. 32C). FIG. 32D shows a situation where multiple implantable electrodes are placed in multiple nerve cords N' within a nerve bundle.

Peripheral nerves have many mixed nerves including motor, sensory, and autonomic nerves, and form nerve bundles. As a nerve cord runs three-dimensionally through the interior of a nerve bundle, and as there are large individual variations in the distribution of nerve bundle and cord, it is difficult to identify a nerve cord by brain coordinates as with the central nerves, but it is possible to clinically identify the principal nerve fibers by observation under a microscope and measurement of neural activity. The implantable electrode of the third embodiment uses these clinical techniques to enable selective signal recording and stimulation of motor, sensory, and autonomic nerves.

The implantable electrode of the third embodiment is not only implanted by surgical techniques, but can also be mechanically inserted by an automatic anastomosis apparatus or a micromanipulator or the like.

(Adjustment of Moisture Absorption Speed)

It is possible to slow the speed with which the conductive composite fibers and the conductive composite fiber bundle(s) composing the implantable electrode of the present invention absorb body fluid within the body. As a method for causing delay, there is a method in which one or more of glycerol, sorbitol, ethylene glycol, squalane, silicone, mineral oil, or MPC (2-methacryloyloxyethylphosphoryl choline) impregnate or are applied to the conductive composite fibers (bundles) in advance. For example, by impregnating the conductive composite fiber bundle 401 of the third embodiment in advance with glycerol, even if electrode implantation into the body proves difficult, and surgical operation time is prolonged, it is possible to prevent occurrence of moisture absorption-induced swelling of the conductive composite fiber bundle 401 and detachment of the nylon thread 406 during the aforementioned surgical operation. By maintaining a narrow diameter of the conductive composite fiber bundle 401, invasiveness relative to biological tissue during electrode implantation can be mitigated.

Fourth Embodiment of the Fourth Aspect

With respect to an implantable electrode 440 of a fourth embodiment of the present invention, as shown in FIGS.

33A and 33B, the conductive composite fiber (bundle) 401 formed in the form of a rod (needle) or cord (cable) is used as a core part, and the perimeter of at least a portion of the core part is coated with a water resistant polymer 404, forming a flow path so that a liquid can infiltrate (permeate) from one end 1*a* (401*a*) to the other end 1*b* of the core part. The one end 1*a* and the other end 1*b* are not coated with the polymer 404, and are exposed.

"Flow path" does not merely signify a hollow tube, but signifies a configuration wherein the water resistant polymer 404 configures a tube, and the conductive composite fiber bundle 401 is disposed inside the tube. As the conductive composite fiber bundle 401 is water absorbent and substance-permeable, a liquid can spontaneously move by infiltrating from the one end 1*a* to the other end 1*b*. The method for transporting a liquid or substance through the flow path is not limited to infiltration, capillary action, diffusion, and the like, and it is also possible to adopt a method wherein a substance is subjected to electrophoresis by establishing either the one end 1*a* or the other end 1*b* as a positive electrode, and the other as a negative electrode, or a method which conducts liquid feeding by connecting a pump (e.g., an osmotic pump) to the one end 1*a*, and applying pressure to the liquid. Whichever method is used, drug transport and liquid feeding can be stably conducted at constant speed.

A reservoir 407 (FIG. 33A) or a chamber 408 (FIG. 33B) into which a medicinal solution can enter is connected to the one end 1*a* of the core part configured by the conductive composite fiber bundle 401. A liquid feeding pump may be connected to a tube connector 409 provided in the chamber 408.

By storing a solution containing a drug in the reservoir 407 or the chamber 408, the aforementioned solution can infiltrate the aforementioned flow path, and pass from the one end 1*a* to the other end 1*b* of the core part. Therefore, the drug can be administered locally to the environs of the other end 1*b* by placing the other end 1*b* at a desired position in biological tissue.

There are no particular limitations on the type of the aforementioned drug, but it is preferable to use a drug which has pharmacological action inhibiting or promoting a biological reaction. As the aforementioned drug, one may cite, for example, a drug that reduces impairment of biological tissue, a drug that promotes repair of biological tissue, a drug that causes growth of biological tissue, and so on. Specifically, for example, one may cite soluble drugs of glycerol, sorbitol, mannitol, fructose, BDNF (brain-derived neurotrophic factor), NGF (nerve growth factor), NT3 (neurotrophin-3), GSNO (S-nitrosoglutathione), SKF96365, cilostazol, TRIM (1-(2-trifluoromethylphenyl) imidazole), gadolinium, magnesium, EGTA (ethylene glycol tetraacetic acid), ruthenium red, and the like. One may cite a configuration wherein a solution in which one or more of these drugs is dissolved is stored in the reservoir 407 of the chamber 408.

There are no particular limitations on the type of water resistant polymer 404 coating the core part, provided that it is a polymer enabling formation of a coating layer on the circumference of the core part (formation of a water seal on the outer surface of the core part), and, for example, polymer (resin) that is used in the field of conventional medical instruments such as catheters may be applied. The water resistant polymer 404 is also preferably endowed with insulating properties in order to avoid an electrical short-circuit between the conductive composite fibers 401 composing the core part and the ambient environment. There are no particular limitations on the thickness of the coating layer composed by the water-resistant polymer 404. For example, one may cite 0.1 µm-5 mm.

As specific examples of the water-resistant polymer 404, one may cite silicone, PTFE (polytetrafluoroethylene), PVC (polyvinyl chloride), ABS (acrylonitrile butadiene styrene), ANS (acrylonitrile styrene), PEN (polyethylene naphthalate), PBT (polybutylene terephthalate), polycarbonate, PEI (polyether imide), PES (polyether sulfone), PET (polyethylene terephthalate), polyamide, aromatic polyamide, polyester, polyether block amide copolymer, polymethyl methacrylate, polyurethane, EVA (ethylene vinyl acetate), ethylene vinyl alcohol, polyethylene, latex rubber, PTFE, FEP, PFA, polypropylene, polysiloxane, ionomer, SAN (styrene acrylonitrile), nylon, thermoplastic elastomer, and so on.

The aforementioned drug may be impregnated in or applied to the conductive composite fibers composing the implantable electrode of the present invention in advance. In this case, as well, the aforementioned drug is gradually released from the aforementioned conductive composite fibers that are implanted in biological tissue, and the aforementioned drug can be locally administered to the environs of the aforementioned conductive composite fibers.

In a state where the other end 1*b* of the core part is implanted in biological tissue, the other end 1*a* and the reservoir 407 or chamber 408 may also be implanted in the biological tissue, or they may be disposed outside of the biological tissue. In the case where the one end 1*a* is implanted in the biological tissue, the volume of the reservoir 407 or the chamber 408 connected to the one end 1*a* is preferably as small as possible. For example, one may cite a capsule-like reservoir 407. In the case where the chamber 408 is placed within the biological tissue, it may also be connected to the exterior of the biological tissue via the tube connector 409 provided in the chamber 408. From the standpoint of reducing invasiveness relative to the biological tissue, the one end 1*a* of the core part and the reservoir 407 or the chamber 408 are preferably set up outside the biological tissue.

The core part which is coated by the water-resistant polymer 404 may be fabricated with a desired length (e.g., 100 µm-10 cm) and thickness (e.g., 10 µm-5 mm) according to application.

There are no particular limitations on the size and constituent material of the reservoir 407 and the chamber 408, and these may be suitably modified according to the purpose and mode of use. For example, a plastic bag or case of silicone resin or the like may be applied as the reservoir 407 or the chamber 408.

In the fourth embodiment, there is no need to coat the entire interval from the one end 1*a* to the other end 1*b* of the conductive composite fiber bundle 401 with the water-resistant polymer 404, and it is acceptable for a portion of the interval to have no coating. The interval where the conductive composite fiber bundle 401 functions as a liquid feed path is preferably coated with the water-resistant polymer 404. In the fourth embodiment shown in FIGS. 33A and 33B, the interval from the vicinity of the other end 1*b* to a part where the reservoir 407 or the chamber 408 is provided, which includes the one end 1*a*, is coated with the water-resistant polymer 404.

There are no particular limitations on the method of connection of the one end 1*a* and the reservoir 407 or the chamber 408. A connection method may be cited wherein the one end 1*a* is installed in an exposed state in the liquid storage part of the reservoir 407 or the chamber 408, and the water-resistant polymer 404 that is coated toward the central side from the one end 1a may be bonded to the outer wall of the reservoir 407 or the chamber 408 with a known adhesive agent or the like.

(Application of Drug Delivery Function)

Heretofore, upon implantation of an electrode into the cerebral nervous system (tissue of the central nervous system), there has been the problem that a limited impairment produced by the invasion during implantation expands, producing a permanent impairment over a wider region than the size of the electrode, and this needs to be remedied.

The drug transport function (drug delivery function) possessed by the implantable electrode 440 of the fourth embodiment of the present invention may be applied to administer drugs for purposes of alleviating impairment due to electrode implantation, and demonstrates particularly remarkable effects in alleviating impairment produced by implantation in nerve tissue. By administering a drug—e.g., GSNO (S-nitrosogluthathione)—that has the effect of alleviating impairment of central nervous tissue from the other end 1b of the aforementioned core part, the damage inflicted on central nervous tissue by the implantable electrode 440 can be greatly mitigated. As a result, transmission and receipt of signals between the electrode and the nervous tissue can be stably conducted with a high degree of accuracy over a longer period than before. A detailed explanation is given with reference to data in the below-described Example 4-4 (FIGS. 34A-34D).

In the case where a drug such as GSNO is used in combination with a conventional biological electrode made of metal or carbon, it is necessary to separately implant a tube (e.g. a microscopic hollow needle such as a microcapillary) to deliver the drug to the implantation site of the biological electrode. Or it is necessary to have a bundle structure wherein the microscopic hollow tube is stored (bundled) as an adjunct to the biological electrode in a single sheath (tube). In this type of bundle structure, the drug release holes (release ports) of the drug transport path are disposed at a distance from the electrode (incorporated into the sheath), with the result that not only is the configuration of the structure that is implanted into the biological tissue rendered more complicated, but it is also difficult to uniformly distribute the drug at the interface of the electrode and the biological tissue.

On the other hand, with respect to the fourth embodiment of the present invention, as the conductive composite fiber bundle 401 that is the electrode itself doubles as a drug transport path, the structure is simple. Furthermore, as the drug seeps out from the surface of the electrode, it is possible to uniformly administered the drug to the interface where the electrode and the cellular tissue come into contact, i.e., to the region where the impairment occurs most. Moreover, the release speed of the drug can be adjusted by adding the aforementioned additives such as glycerol to the conductive composite fiber bundle 401.

The drug transport function (drug delivery function) of the implantable electrode 440 of the fourth embodiment of the fourth aspect of the present invention is not limited to drug administration applications for purposes of alleviating impairments to biological tissue. For example, it can also be used in a variety of applications to stimulate or utilize the physiological functions of living cells and biological tissue, such as selective bonding of nerve fibers (selective formation of neural wiring) by neurotrophic factors, and recording of electrical signals associated with selective stimulation of nerve fibers. Moreover, the liquid that is distributed through the flow path of the implantable electrode 440 is not limited to drug solutions, and there are no particular limitations on its composition or function, provided that it is a liquid capable of infiltrating and moving through the conductive composite fiber bundle 401.

<<Examples of Effects Obtained by the Fourth Aspect of the Present Invention>>

According to the implantable electrode of the present invention, for example, the following effects are obtained.

1. A biological electrode configured using flexible conductive composite fibers can be set within biological tissue.

2. Connection of the conductive composite fibers with an electric wire (signal cable) can be stably maintained within a living body.

3. A drug can be transported at constant speed to a site where the electrode contacts biological tissue.

4. Impairment of biological tissue (particularly of cerebral nervous tissue) due to placement (implantation) of the electrode can be alleviated.

5. It is possible to stably record biological signals over long periods.

6. The electrode can be three-dimensionally placed in conformity with a three-dimensional structure of neural tissue.

EXAMPLES

Examples of the First Aspect

Next, the first aspect of the present invention is described in further detail with reference to Examples, but the first aspect of the present invention is not limited by the following Example.

<Evaluation of Tensile Strength>

Comparative Example 1-1

Figure 9A:
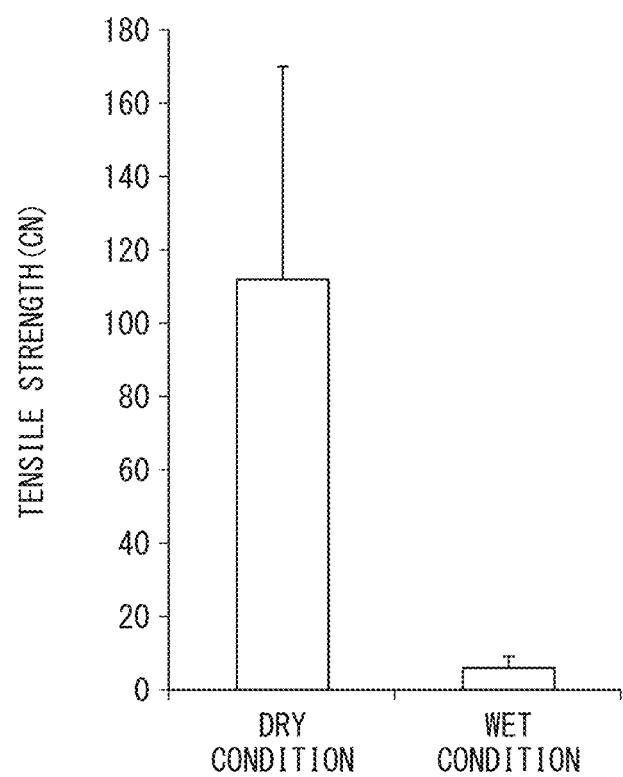
FIG. 9A is a graph which shows results of Comparative example 1-1.

A liquid obtained by drying condensation of Heraeus CLEVIOS P solution (produced by Heraeus, Ltd.) was uniformly applied onto a plate, and naturally dried, and ethanol was further fixed thereon to fabricate a PEDOT-PSS film (sectional area 0.03 mm$^2$, length 3 cm) which was used for test samples. FIG. 9A shows the results of studies respectively pertaining to tensile strength of the samples in a dry state and a wet state (a state in which pure water is absorbed until saturation).

From the graph, it is clear that the tensile strength of PEDOT-PSS linear material in a wet state (on the right) has undergone a steep decline to the point where it is approximately 10% of tensile strength in a dry state (on the left).

Example 1-1

Figure 9B:
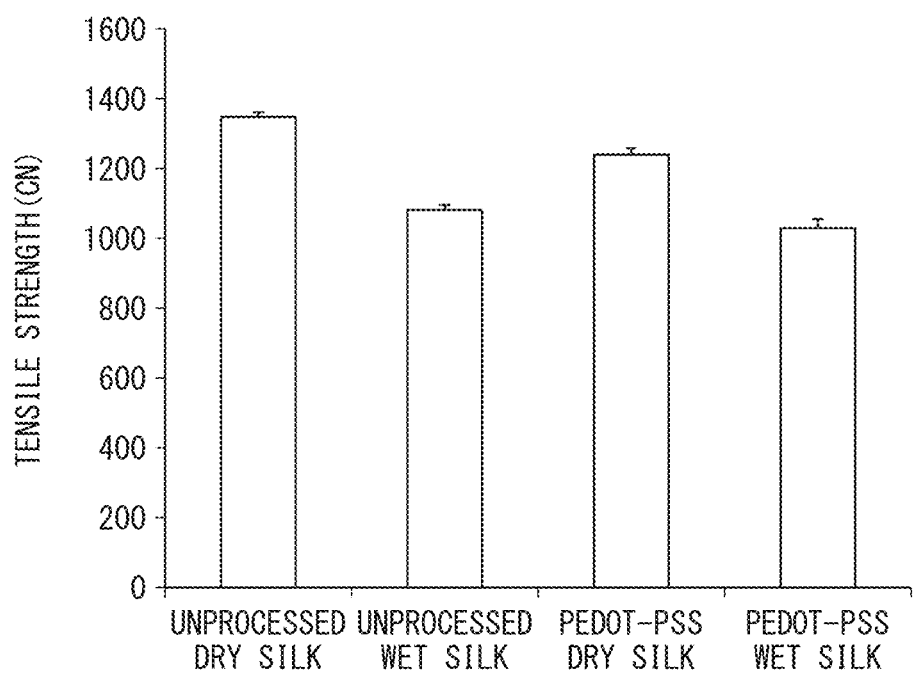
FIG. 9B is a graph which shows results of Example 1-1.

FIG. 9B shows the results of studies pertaining to the tensile strength of raw material silk thread (No. 9 silk thread, produced by Fujix, Ltd.; twisted thread of 18 fibers of 21 D denier silk fiber, with a thread diameter of approximately 280 μm, and a length of 20 cm) in a dry state and a wet state (a state in which pure water is absorbed until saturation).

FIG. 9B shows the results of studies of tensile strength in a dry state and a wet state (a state in which pure water is absorbed until saturation) of a conductive polymer fiber bundle of approximately 280 μm diameter consisting of PEDOT-PSS and the aforementioned silk thread (No. 9 silk thread) (hereinafter sometimes referred to as "PEDOT-PSS silk fiber bundle 1"). The bundle was obtained by the above-described production method 2b by conducting immersion for one hour in 20 cc of the aforementioned CLEVIOS P solution, by subsequently using a comb-like multi-point electrode to conduct electrochemical fixation by energization of 3 mC per 1 cm using ethanol as an organic solvent, and then by removing 60% of the water by the blowing of dry air during partial drying of the moisture contained in the solution. The vertical axis of the graph represents maximum strength (CN: centimeter Newton), and the error bar represents a standard deviation per 10 specimens. The tensile strength test conformed to the JIS L 1013 standard, a constant rate extension type tester (manufactured by Orientec Co., Ltd., model RTC-1210A) was used with a fiber length between grips of 20 cm, and a tension speed of 20 cm/min, and maximum strength was obtained from an average of measured values from 10 tests.

The specific measured values (CN) of the aforementioned graph are as follows.
  Dry unprocessed silk: average value=1350.4, standard deviation=8.11
  Wet unprocessed silk: average value=1082.9, standard deviation=12.28
  Dry PEDOT-PSS silk: average value=1238.8, standard deviation=16.93
  Wet PEDOT-PSS silk: average value=1031.4, standard deviation=24.45

From the graph, when a comparison is made of the raw material silk in a dry state and a wet state and the PEDOT-PSS silk fiber bundle 1 in a dry state and a wet state, no clear difference in strength can be observed between the two. That is, the tensile strength of the PEDOT-PSS silk fiber bundle 1 in a wet state preserves 83% of strength in a dry state, while the tensile strength of the raw material silk thread in a wet state preserves 80% of strength in a dry state. From this finding, it is clear that the conductive polymer fiber of the present invention has the same excellent strength as raw material silk thread whether in a dry state or a wet state, and inhibits breakage, cracking, and the like, with the result that its conductivity is not easily reduced. Furthermore, with respect to the strength difference when dry and when wet, it is clear that the PEDOT-PSS silk fiber bundle 1 has a smaller strength difference (a reduction of 17% (207 CN) if strength when dry is used as the standard) than the raw material silk thread (a reduction of 20% (268 CN) if strength when dry is used as the standard), with the result that the PEDOT-PSS silk fiber bundle 1 undergoes a smaller change in strength due to wetness, and has stable strength properties.

From the results of Example 1-1 and Comparative example 1-1, it is obvious that the tensile strength of the conductive polymer fiber (in a dry state) of the present invention is approximately 10 times better than that of conductive fiber (in a dry state) composed only of PEDOT-PSS.

<Evaluation of Water Resistance>

Example 1-2

With respect to conductive polymer fiber (PEDOT-PSS silk fiber bundle 1) produced by the same method as Example 1, a sample A impregnated with glycerol, and a sample B not be impregnated with glycerol were prepared.

Figure 10:
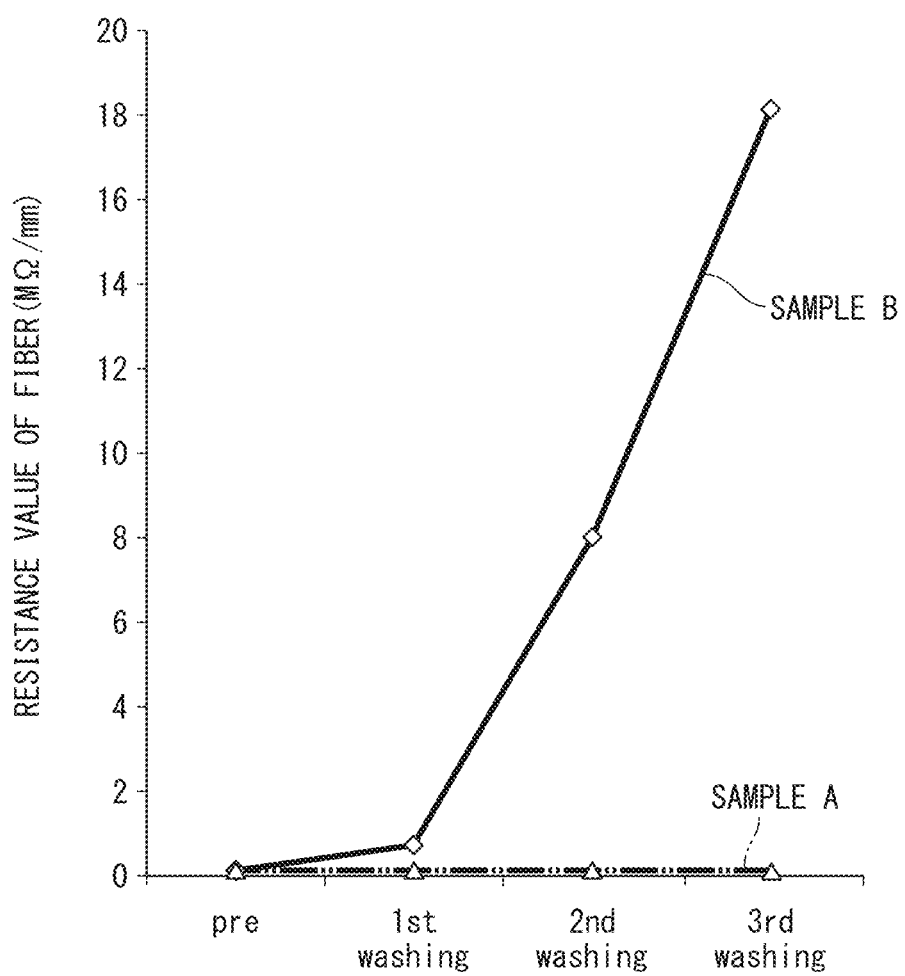
FIG. 10 is a graph which shows results of Example 1-2.

In a state where the respective samples A and B were immersed in pure water, shaking was conducted under conditions of 5 cm horizontal amplitude, 3 Hz, 10 times. Thereafter, 3 sets of washing treatment with natural drying were repeated, and changes in the resistance values of each sample A and B were recorded. The resistance values were calculated from current volume during DC5 load, using a direct-current stabilized power source (PAB18-5.5, manufactured by Kikusui Electronics Corp.) and a digital multimeter (VOAC7511, manufactured by Iwatsu Electric Co., Ltd). Measurement of resistance values was conducted on the samples in a dry state (in a state free of moisture). The results are shown in FIG. 10. The vertical axis of the graph shows resistance values (MΩ/mm) per 1 mm of length of the PEDOT-PSS silk fiber bundle 1 (in a dry state) that has a fiber diameter of approximately 280 microns.

According to the graph, in the case of the PEDOT-PSS silk fiber bundle 1 to which glycerol is not added (Sample B; plotted with "◊" linked by a solid line in the graph), the resistance values increase as a result of repetition of washing treatment, reducing conductivity. On the other hand, with respect to the PEDOT-PSS silk fiber bundle 1 to which glycerol is added (Sample A; plotted with "Δ" linked by a double-dotted line in the graph), it is clear that no increase is observed in the resistance values, and that conductivity is maintained. In short, water resistance can be enhanced by impregnating the conductive polymer fiber of the present invention with an additive such as glycerol.

<Evaluation of Biological Electrode (1)>

Example 1-3

Figure 11A:
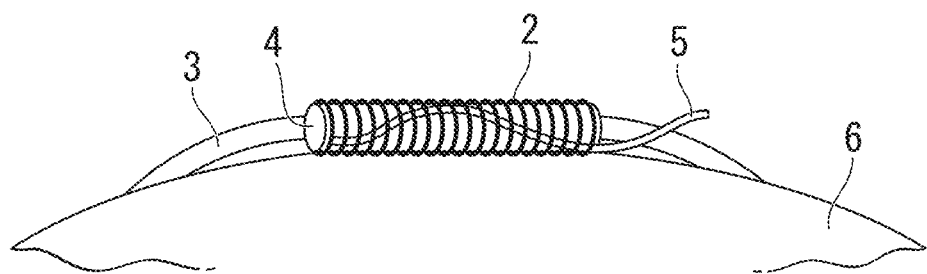
FIG. 11A is a schematic view which shows an example of the present invention, showing circumstances where a biological electrode is placed on a body surface.
Figure 11B:
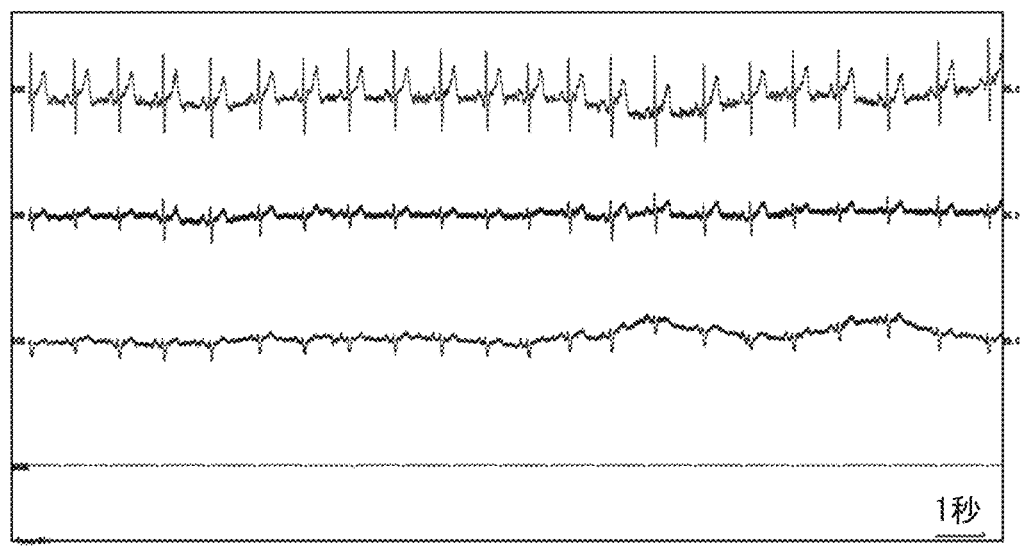
FIG. 11B is a measured human electrocardiogram (I, II, III-lead in order from above).

Using conductive polymer fiber with a diameter of approximately 280 μm and a length of 300 mm composed of the aforementioned silk thread (No. 9 silk thread) and PEDOT-PSS obtained by the above-described production method 2b (hereinafter sometimes referred to as "PEDOT-PSS silk fiber bundle 2"), as shown in FIG. 11A, a rubber band 4 and a metallic conductor wire 5 is provided on top of a fixed cord 3, and the PEDOT-PSS silk fiber bundle 2 is wound around them in a coil shape as an electrode to produce a cord-like body-surface type biological electrode. This biological electrode is set on a human body surface 6. FIG. 11B shows one example of a result of human electrocardiogram measurement using these biological electrodes.

When measuring a human electrocardiogram, measurement was able to be conducted by bringing the PEDOT-PSS silk fiber bundle 2, which is the electrode composing the biological electrode, into contact with skin without use of paste (jelly) containing an electrolyte. In short, as a biological electrode provided with the PEDOT-PSS silk fiber bundle 2 of the present invention has excellent strength, flexibility, conductivity, it is clearly capable of attachment by adhesion to a body surface.

The attachment sites of the biological electrodes were located on the skin (body surface) of the upper right limb, upper left limb, and lower left limb, each biological electrode was connected to an electrocardiograph (Polygraph, AP1124, manufactured by TEAC, Ltd.), and the human electrocardiogram was recorded during repose by the bipolar limb lead method (setting sensitivity 2000 μV/mm; timescale 1 second; lead I, II, III).

<Evaluation of Biological Electrode (2)>

Example 1-4

Figure 12A:
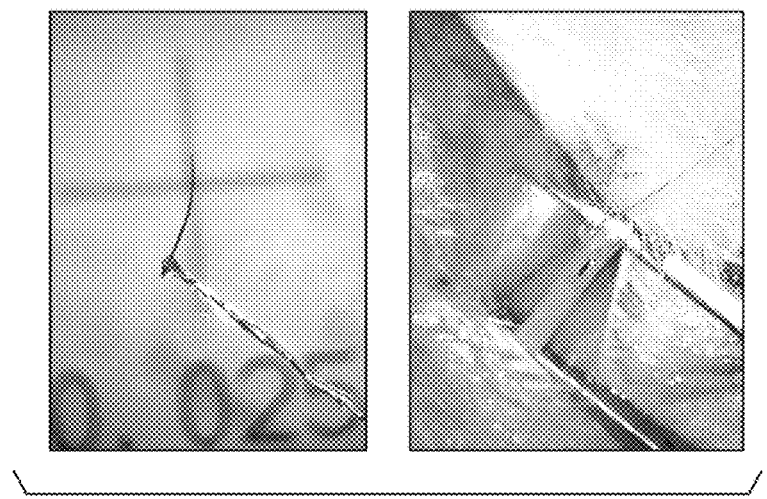
FIG. 12A is an observation photograph by stereomicroscope of a fabricated thread-like implantable biological electrode.

The circumference of conductive polymer fiber with a diameter of approximately 280 μm and a length of 1.5 mm composed of the aforementioned silk thread (No. 9 silk thread) and PEDOT-PSS obtained by the above-described production method 1a was coated with silicone resin to insulate a portion thereof. Specifically, the length of the exposed portion (non-insulated portion) was set at approximately 500 μm, and the length of the insulated coated portion was set at approximately 1000 μm. The electrode resistance of the obtained conductive polymer fiber (hereinafter sometimes referred to as the PEDOT-PSS silk fiber bundle 3) was approximately 500 kΩ, and this was connected to a metal wire (Xwire, produced by Tanaka Kikinzoku Kogyo Co., Ltd.) to produce a thread-like implantable biological electrode. FIG. 12A shows a photograph thereof taken by stereoscopic microscope.

Figure 12B:
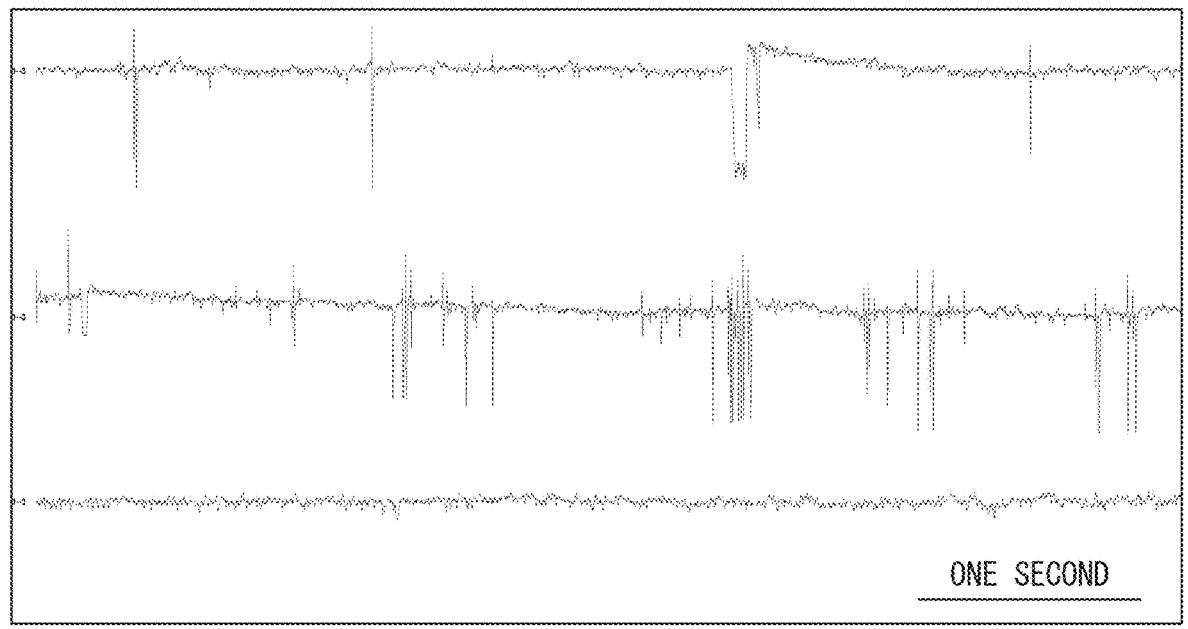
FIG. 12B is a measured action potential of a rat sciatic nerve (in order from above: when at rest; when contracted; when relaxed).

Next, the biological electrode that was produced was inserted directly under the epineurium of the sciatic nerve of a rat under a microscope, and was fixed by ligature using surgical thread for microsurgery (S&T 10-0) (right figure of FIG. 12A). After the operation, the metal conductor wire was connected to a pre-amplifier, and the action potential (aggregate action potential) of the sciatic nerve was recorded using a biological signal recorder (AP1024, manufactured by TEAC, Ltd.). An example of measurement results is shown in FIG. 12B. With respect to measurement conditions, setting sensitivity is 2000 μV/mm, timescale is 1 second, and in order from the top is during rest, during muscle contraction, and during muscle relaxation.

As the implantable biological electrode provided with the PEDOT-PSS silk fiber bundle 3 of the present invention is thread-like, it can be sewn into tissue by a surgical operation. Consequently, compared to conventional large-sized metal electrodes of inferior flexibility, the biological electrode of the present invention has a high degree of freedom with respect to implantation sites, the electrode can be fixed in a stable state, and only a minimum required part is exposed while the remainder is covered, thereby resulting in a high degree of durability, and allowing recording over long periods.

<Evaluation of Conductivity>

Example 1-5

Using the aforementioned silk thread (No. 9 silk thread), conductive polymer fiber was produced in which PEDOT-PSS is arranged within and on the outer circumference of the silk thread by the above-described production method 2b. Specifically, the following samples were prepared: a sample C on the outer circumference of which PEDOT-PSS is electrochemically coated once, and dried; a sample D obtained by impregnating the sample C with glycerol; a sample E obtained by electrochemically applying an additional coat of PEDOT-PSS (for a total of two coats); and a sample F obtained by impregnating the sample E with glycerol.

The conductivity of each sample C, D, E, and F in a dry state (a state free of moisture) was measured by the resistance value measurement method described in Example 1-2, and the results of measurement of the respective resistance values by the same method as Example 1-2 are shown in Table 1.

Based on the obtained results, in order to enhance conductivity and resistance values, it is clearly preferable to have a thicker conductor thickness (in terms of the number of coats, two are preferable to one), and to add glycerol.

TABLE 1

| Silk thread (No.) | Number of coats | Additive | Fiber resistance (MΩ/cm) | Conductivity (S/cm) |
|---|---|---|---|---|
| 9 | 1 | — | 9.04 | 0.000184 |
| 9 | 1 | Glycerol | 0.0575 | 0.0304 |
| 9 | 2 | — | 1.59 | 0.00135 |
| 9 | 2 | Glycerol | 0.0206 | 0.102 |

Examples of the Second Aspect

The second aspect of the present invention is described below with further specificity by Examples, but the second aspect of the present invention is not limited in any way by the Examples.

Example 2-1

In the present Example, silk fiber (No. 9 silk thread with a diameter of approximately 280 μm) was prepared as machine-made fiber. As shown in FIG. 13 and FIG. 15A-B, using a production apparatus provided with the rotor electrodes of the present invention, conductive polymer fiber was produced by polymerizing and fixing a conductor containing PEDOT-PSS to the outer circumference of silk fibers and to the interior of a fiber bundle composed of the aforementioned silk fibers. At this time, two types of conductor solution were prepared, one in which an additive was not used, and one to which glycerol was added, and each was subjected to electrochemical polymerization and fixation.

With respect to the rotor electrodes, as shown in FIG. 13A-B, the pulley-like rotor electrodes 222 and the roller-like rotor electrodes 232 were used, and these respective rotor electrodes 222 and 232 were alternately arranged so as to sandwich the silk fibers from both sides in the radial direction of the aforementioned silk fibers. At this time, as the pulley-like rotor electrodes 222, electrodes having pulleys 222a with a diameter of 8 mm and a width of 4 mm were used. As the roller-like rotor electrodes 232, electrodes having rollers 232a with a diameter of 6 mm and a width of 3 mm were used.

Specifically, as described in the aforementioned embodiments of the present invention, silk fibers were immersed in a conductor solution containing PEDOT-PSS stored in an immersion container, and these were vertically raised with a reel unit. In this instance, using comb teeth-like electrodes like those shown in FIG. 14, the silk fibers were alternately sandwiched from both sides by multiple comb teeth, and energization was conducted while the silk fibers were being raised. In this instance, using a direct-current stabilized power source (manufactured by Kikusui Electronics Corp.: PAB18-5.5), direct-current power of 20 μA and 18 V was supplied to the comb teeth-like electrodes, and adjustment was conducted by current-voltage monitoring using a "Digital Multi-Meter (manufactured by Iwatsu Electric Co., Ltd.: VOAC7511)" so as to assure a quantity of electricity of 3-6 mC in polymerization and fixation of 10 mm of silk fibers in the lengthwise direction (electric flux density: 5.85-9.95× $10^4$ C/m$^2$).

With respect to the obtained conductive polymer fiber, fiber resistance and conductivity were measured over a fiber length of 10 mm under direct current of 350 mA using a resistance measuring apparatus "DM 2561 (manufactured by NF Corporation)." As a fiber gripping tool, a nanogrip manufactured by Stack Electronics Co., Ltd. was used. Measurement at this time was conducted in a dry state (a state free of moisture), and the results are shown in the following Table 2. In Table 2, Example 1 indicates Example 2-1, and Comparative example 1 indicates Comparative example 1-1.

Figure 17A:
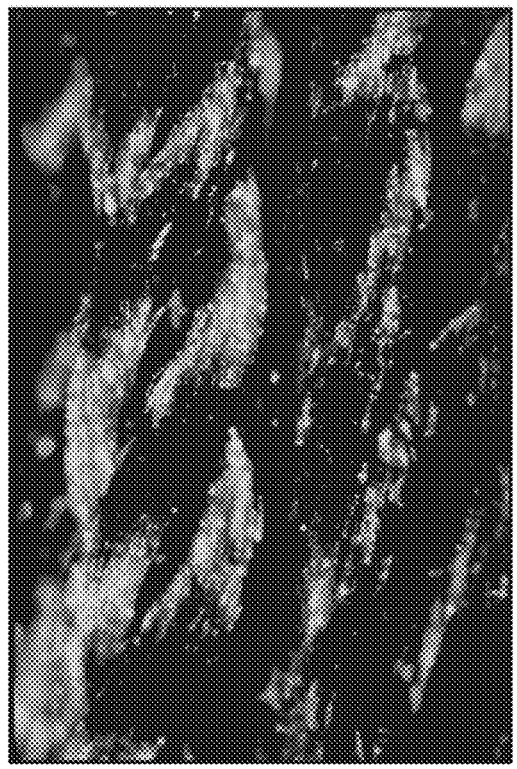
FIG. 17A is a figure which serves to describe an example of the method and the device for producing the conductive polymer fibers of the present invention, and is a photograph which shows conductive polymer fibers obtained in Example 2-1 by conducting energization using the rotor electrodes of the present invention.

With respect to the obtained conductive polymer fiber, the coating condition of the conductor containing PEDOT-PSS was visually confirmed by observation using a stereoscopic microscope, and a photo taken at that time is shown in FIG. 17A.

Figure 18A:
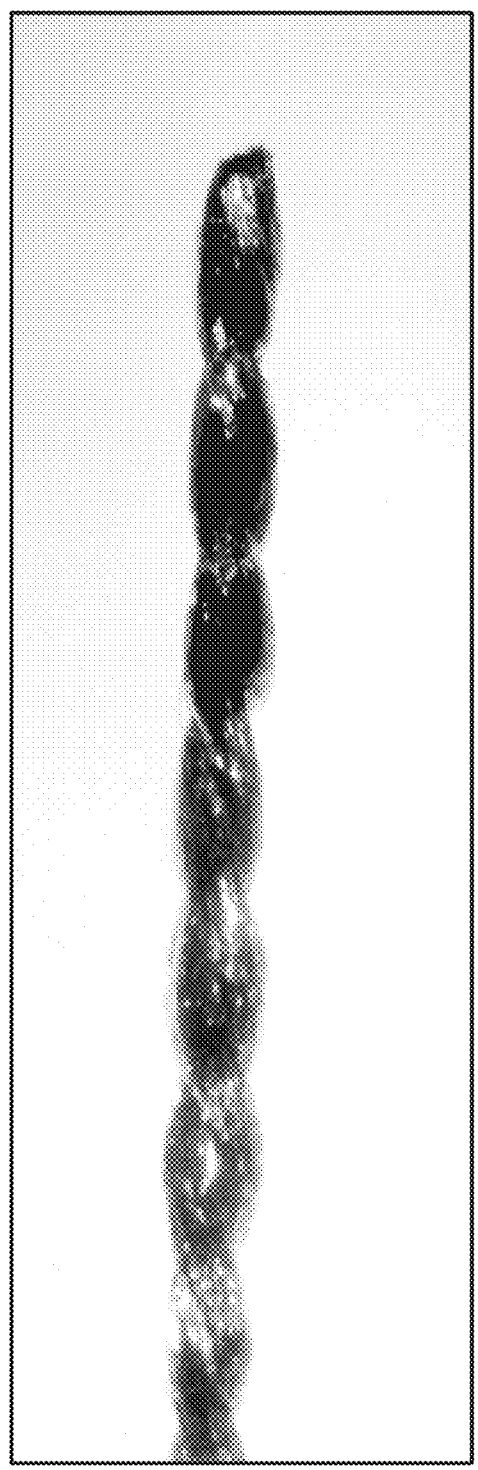
FIG. 18A is a figure which serves to describe an example of the method and the device for producing the conductive polymer fibers of the present invention, and is a photograph which shows a condition after water-resistance testing of conductive polymer fibers obtained in Example 2-1 by conducting electrochemical polymerization and fixation using the method and the device of the present invention.

In addition, the water resistance of the obtained conductive polymer fiber was evaluated by taking a stereoscopic microscope image (using a Leica SZ) after immersion for one month in physiological saline water (0.9% NaCl solution: 20° C.), and the photo is shown in FIG. 18A.

TABLE 2

| Type | No additive | | Glycerol added | |
|---|---|---|---|---|
| | Fiber resistance (MΩ/cm) | Conductivity (S/cm) | Fiber resistance (MΩ/cm) | Conductivity (S/cm) |
| Example 1 | 9.41 | $1.69 \times 10^{-5}$ | 0.0721 | $2.21 \times 10^{-3}$ |
| Comparative example 1 | 35.3 | $4.51 \times 10^{-6}$ | 13 | $1.22 \times 10^{-5}$ |

Example 2-2

With respect to the Example, conductive polymer fiber was produced in the production apparatus shown in FIG. 13 under the same conditions and by the same procedure as Example 2-1 described above, except for the point that energization was conducted using the comb teeth-like electrodes 221 and 231 shown in FIG. 14. In this instance, with respect to the comb teeth-like electrodes 221 and 231, a distance between comb teeth (distance between electrodes) of 10 mm was used for the multiple comb teeth 221a and 231a.

Figure 17B:
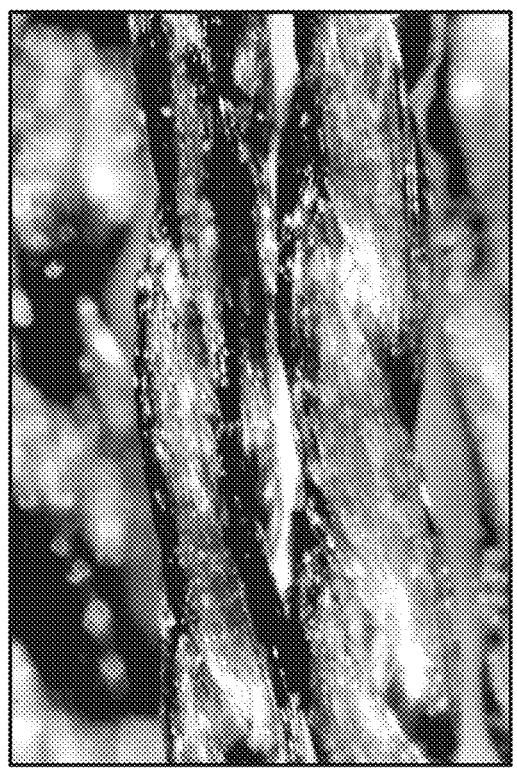
FIG. 17B is a photograph which shows conductive polymer fibers obtained in Example 2-2 by conducting energization using comb teeth-like electrodes.

With respect to the obtained conductive polymer fiber, the coating condition of the conductor containing PEDOT-PSS was visually confirmed by observation using a stereoscopic microscope, and the photograph taken at that time is shown in FIG. 17B.

Comparative Example 2-1

In Comparative example, conductive polymer fiber was produced by fixing a conductor containing PEDOT-PSS to the outer circumference of silk fibers and to the interior of a fiber bundle consisting of the aforementioned silk fibers under the same conditions and by the same procedure as Example 2-1 described above, except for the point that the conductor was fixed to the silk fibers (base fibers) by the conventional chemical fixation method. The fiber resistance and the conductivity of the obtained conductive polymer fibers were measured by the same method as above, and the results are shown in Table 2.

Figure 18B:
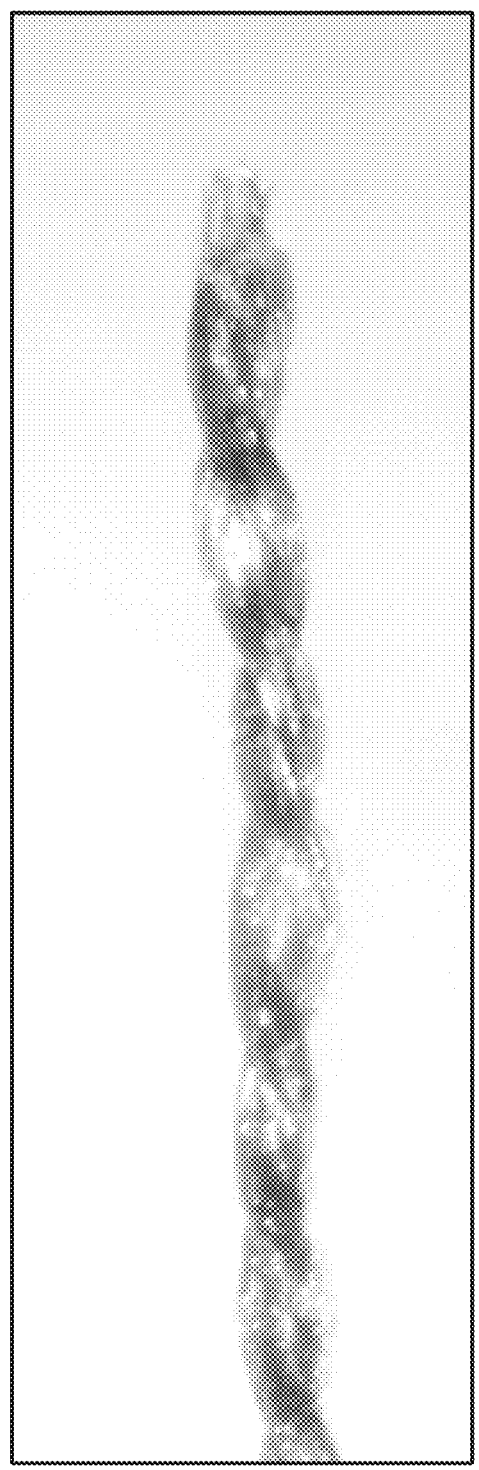
FIG. 18B is a photograph which shows a condition after water-resistance testing of conductive polymer fibers obtained in Comparative example 2-2 with conventional chemical fixation.
Figure 19A:
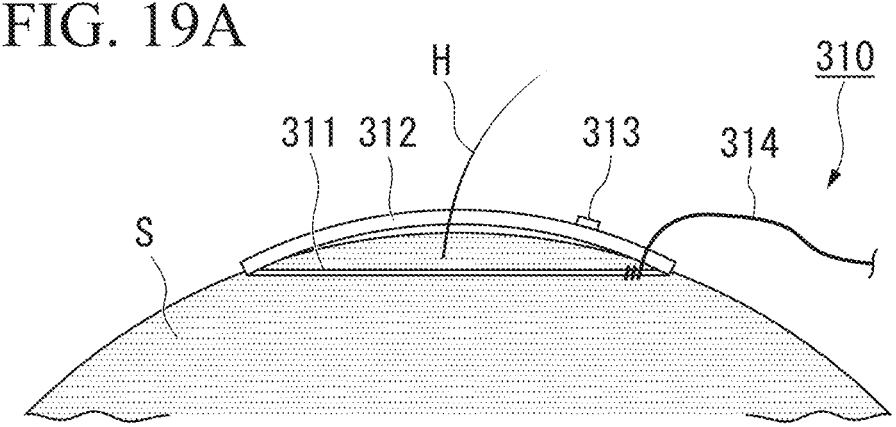
FIG. 19A is a schematic view of a comb tooth-like electrode pertaining to a first embodiment of the third aspect of the present invention, and is a side view of a comb tooth-like biological electrode 310 which shows a condition where a contact 311 is fixed like a bowstring to an arcuate first frame 312.
Figure 19B:
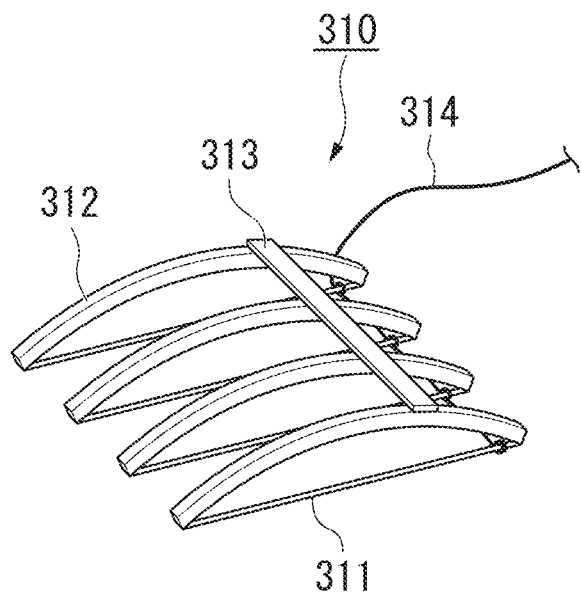
FIG. 19B is a perspective view of the aforementioned biological electrode 310.
Figure 19C:
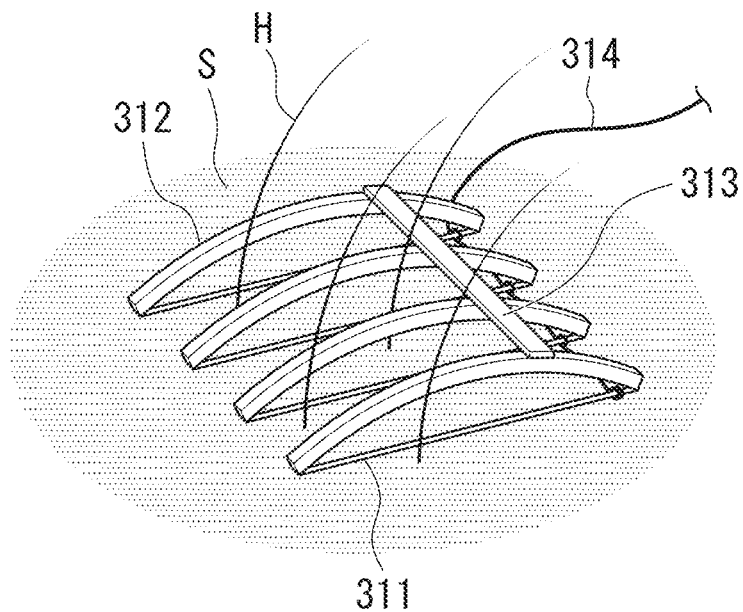
FIG. 19C is a perspective view which shows a condition where the aforementioned biological electrode 310 is inserted into gaps between scalp hairs H, and is fixed at a position of contact with a scalp S.
Figure 19D:
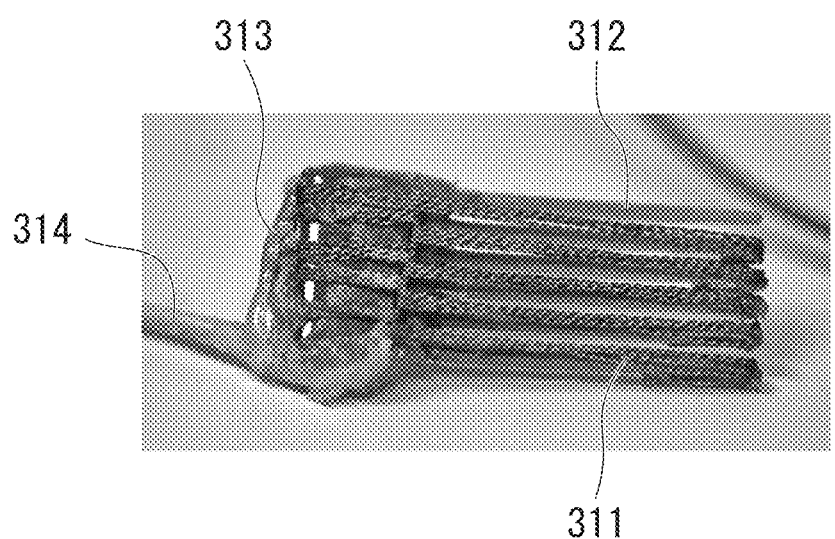
FIG. 19D is a photograph which shows a region where the aforementioned biological electrode 310 contacts skin.
Figure 20A:
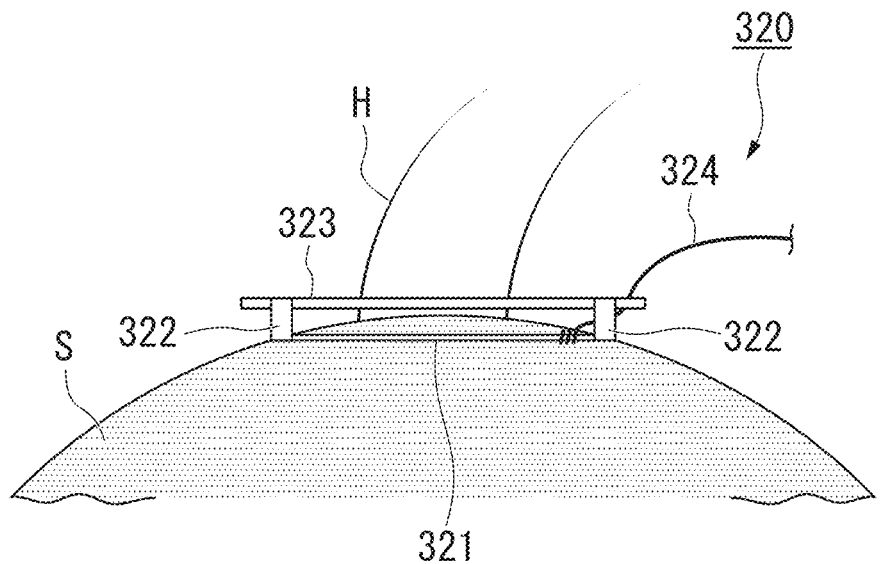
FIG. 20A is a schematic view of a hairpin-like electrode pertaining to the first embodiment of the third aspect of the present invention, and is a side view of a biological electrode 320 which shows a condition where a contact 321 is fixed in two parallel lines like a bowstring to a hairpin-like hair clip via fixing posts 322.
Figure 20B:
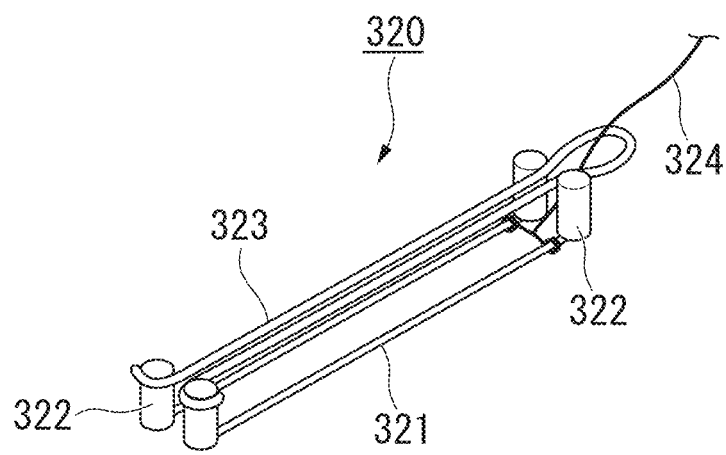
FIG. 20B is a perspective view of the aforementioned biological electrode 320.
Figure 20C:
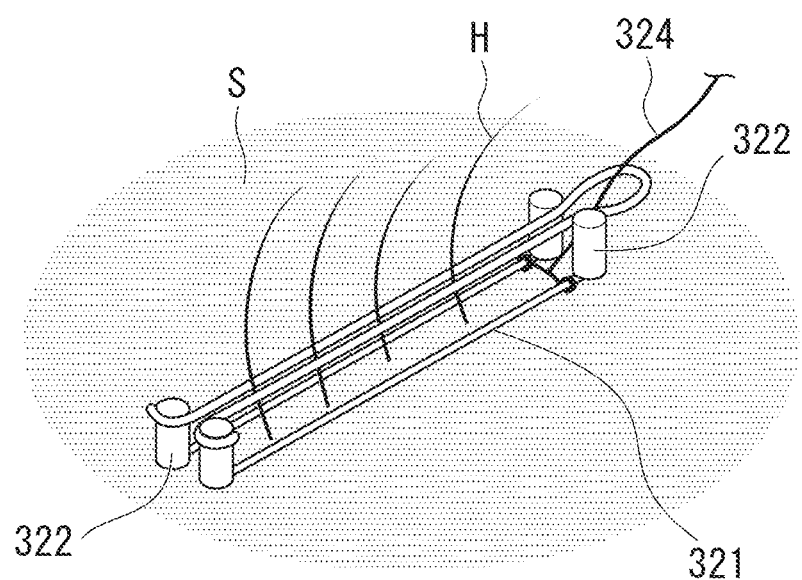
FIG. 20C is a perspective view which shows a condition where the aforementioned hairpin-like biological electrode 320 sandwiches scalp hairs H at a position close to the scalp S, and where the contact 21 contacts the scalp S.
Figure 20D:
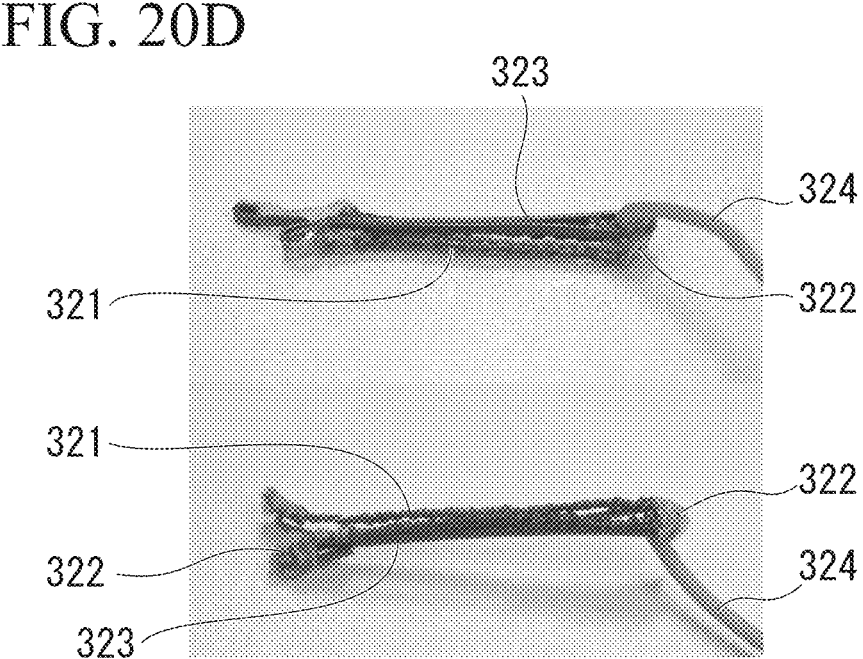
In FIG. 20D, the upper level is a photograph taken of the top surface of the hairpin-like biological electrode 320, and the lower level is a photograph taken of the bottom surface that contacts the skin.

Water resistance was also evaluated by the same method as Example 2-1 described above, and a photograph taken as a stereoscopic microscope image is shown in FIG. 18B.

(Evaluation Results)

Per the results shown in Table 2, compared to the conductive polymer fiber of Comparative examples produced by the chemical fixation method using a conventional production apparatus, it is clear that the conductive polymer fiber of Example 1 in which a conductor containing PEDOT-PSS is electrochemically polymerized and fixed to silk fibers (base fibers) by the production method prescribed by the present invention using the production apparatus of the present invention obtains lower fiber resistance and superior conductivity regardless of the presence or absence of additives.

As shown by the photograph figure of FIG. 17A, it is clear that the conductive polymer fiber obtained by Example 2-1 is uniformly coated by the conductor containing PEDOT-PSS on the surface of the silk fibers and to the interior of the fiber bundle, and that the conductor is fixed without exposure of silk fibers.

Furthermore, as shown in the photograph figure of FIG. 18A, it was confirmed with respect to the conductive polymer fiber obtained in Example 2-1 that the coating condition of the conductor on the surface of the silk fibers and to the interior of the fiber bundle (the black color on the surface of the silk fibers) was maintained even after 1 month of water resistance testing.

On the other hand, as shown in Table 2, the conductive polymer fiber produced using the conventional chemical fixation method clearly had higher fiber resistance and lower conductivity than the conductive polymer fiber of Example 2-1.

As shown in the photograph figure of FIG. 18B, with respect to the conductive polymer fiber obtained in Comparative example 2-1, it was observed after one month of water resistance testing that the silk fiber was in an exposed state (there was a white-gray color on the surface of the silk fibers), and it was confirmed that most of the conductor had peeled off and vanished.

As shown in the photograph figure of FIG. 17B, compared to the conductive polymer fiber of Example 1 produced using rotor electrodes, it was confirmed with respect to the conductive polymer fiber obtained using comb teeth-like electrodes in Example 2-2 that the surface of the silk fibers was partially exposed. The reason for this would seem to be that, when conducting energization using the comb teeth-like electrodes during vertical lifting, conductor is peeled off due to contact with some of the comb teeth (metal rod electrodes), but as the rate of coating of the silk fiber surface is higher than in the conductive polymer fiber produced by the Comparative examples, the product is superior both in terms of fiber resistance and conductivity compared to the conventional product.

Examples of the Third Aspect

Next, the third aspect of the present invention is described in further detail with reference to Examples, but the third aspect of the present invention is not limited by Examples shown below.

Example 3-1

Comb-Like Brainwave Electrode

A silk fiber bundle before composite fiber production (produced by Fujix, Ltd.: Taiya No. 9, fiber diameter approximately 280 μm) was immersed in a solution in which 0.1% EDOT (produced by the German company Heraeus, Ltd.) was added to PEDOT-PSS (CLEVIOS P produced by the German company Heraeus, Ltd.).

Subsequently, the aforementioned silk fiber bundle was energized to electrochemically fix the PEDOT-PSS to the surface and the interior of the silk fiber bundle, thereby producing conductive composite fiber including the silk fiber bundle and PEDOT-PSS. This conductive composite fiber bundle was bundled in 4 units, and was fixed by being spread on comb-like arcuate frames made of polystyrene (4 sites for a total of 16 units), obtaining the comb-like biological electrode 10 shown in FIG. 19A-19D.

As the signal cable 314 joined to the contacts 311 composed of the conductive composite fiber, a signal cable for a brainwave measurement apparatus (manufactured by Nihon Kohden Corporation) was used. The coating of this signal cable was stripped away to a length of 1 cm, and the conductive composite fiber was wound around the exposed copper wire, and fastened. The junction of the conductive composite fiber and the signal cable was coated and insulated with an ethylene vinyl alcohol adhesive. The aforementioned junction was then fixed to a frame end together with the signal cable.

Prior to using the biological electrode in brainwave measurement, the contacts 311 (conductive composite fibers) were impregnated with glycerol. As a result of impregnation with glycerol, the conductivity and water resistance of the conductive composite fibers were enhanced, and fiber flexibility was improved, thereby enabling satisfactory contact between the contacts 311 and the scalp, and stable measurement of brainwaves. With respect to the biological electrode 310 produced in the Example, its size was 12 mm in width, 35 mm in length, and 6 mm in thickness with a 2 mm thickness at the comb tip, its weight was 1.1 g (electrode only, not including cable weight), and it was also thinner, and lighter in weight. Furthermore, as its form was comb-shaped, the biological electrode 310 could be attached with concealment under head hair.

Example 3-2

Hairpin-Like Brainwave Electrode

Conductive composite fibers identical to those in Example 1 were used. A hairpin-like hair fastener with a length of 3.5 cm was used as the frame. The aforementioned hairpin was made of steel, and its surface was painted with urethane resin. The coating of a signal cable for brainwave measurement (manufactured by Nihon Kohden Corporation) was stripped away to a depth of 3 cm, and conductive composite fibers were doubly wound around the exposed copper wire to produce a contact with a thickness of approximately 1 mm (FIG. 21C). Two contacts were fixed to the two ends of a U-shaped frame of the hairpin via a support made of ethylene vinyl to obtain the hairpin-like biological electrode 320 shown in FIG. 20A-20D. With respect to the biological electrode 320 produced in the Example, its size was 35 mm in length, 2-5 mm in transverse width, and 3 mm in height, and its weight was 0.5 g (electrode only, not including cable weight). In the case where brainwave measurement is conducted using the biological electrode 320, as the electrode itself grips the head hair, it is capable of self-fixing, and a holder such as a stretchable net may be used or not used.

FIG. 23A shows a human brainwave measured using the hairpin-like brainwave electrodes of Example 3-2. As different electrodes, hairpin-like electrodes of Example 3-2 were respectively attached at C3 and C4. As indifferent electrodes, silver-silver chloride plate electrodes (NE134A manufactured by Nihon Kohden Corporation, for use with collodion electrodes) were attached with fixation to both sides of an auricle (earlobe) using tape, with interposition of absorbent cotton containing physiological saline water. Pretreatment such as delipidation and dead skin removal was not conducted with respect to the skin to which the electrodes were attached. FIG. 23A shows a waveform obtained by measuring a brainwave of an adult male in a conscious state in an ordinary laboratory under conditions of a 1 Hz low-pass cutoff filter, and a 20 Hz high-pass cutoff filter, using MEB5504 manufactured by Nihon Kohden Corporation. Now, the horizontal axis of the figure is 400 ms/div, and the vertical axis is 50 µV/div.

Figure 23B:
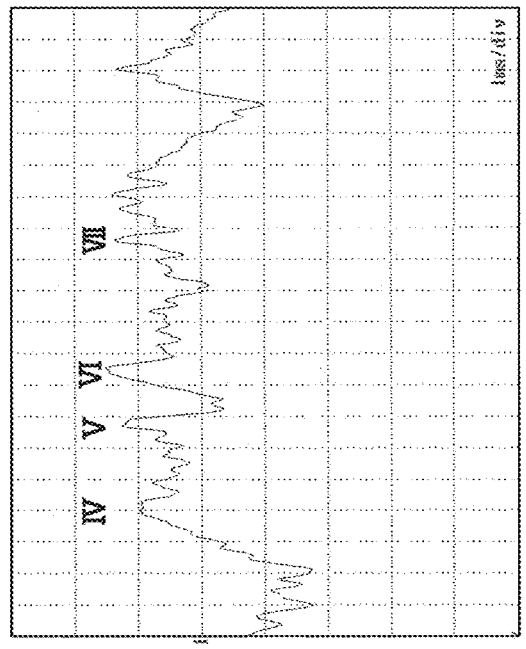
FIG. 23B is a graph which shows human auditory brainstem response (showing 0.2 $\mu$V, 1 ms/div 90 db, click sound, 1000-time adding mean, and peak of IV-VII evoked potential) measured by a hairpin-like electrode for brainwave use.

FIG. 23B shows the auditory brainstem response (evoked potential) of an adult male measured using the hairpin-like brainwave electrodes of Example 3-2. The employed measurement apparatus (MEB5504 manufactured by Nihon Kohden Corporation) and the electrode attachment were the same as in the brainwave measurement of FIG. 23A. Clicking sound of 90 db was input to both ears from headphones, and averaging of 1000 times was conducted according to the standard setting values of auditory evoked potential. Now, the horizontal axis of the figure is 1 ms/div, and the vertical axis is 0.2 µV/div. From the evoked potential waveform measured under conditions of 1 Hz low-pass cutoff filter, and 200 Hz high-pass cutoff filter, it is shown that the biological electrode of the embodiments of the present invention can be used to measure evoked potential.

Example 3-3

Electrocardiogram Electrode

For purposes of comparing the stability of measured biological signals and the occurrence of noise, the following three types of electrodes 1-3 were attached to the body surface of the same experimental animal (a rat), simultaneous measurement of electrocardiograms was conducted, and the measured waveforms were compared.

Electrode 1 (the electrode of the second embodiment of the present invention): contacts in which were arranged 30 fibers (of 12 mm length) obtained by impregnating conductive composite fibers produced in the same manner as Example 3-1 with glycerol were attached to the rat body surface, and fixed by the two methods described below.

Electrode 2 (conventional type): an electrode (F120S, manufactured by Nihon Kohden Corporation) generated by applying conductive gel to a silver-silver chloride electrode was attached to the rat body surface, and fixed by the two methods described below.

Electrode 3 (conventional textile electrode): a commercial sports heart rate monitor electrode (brand name: Smart Fabric Sensor, WearLink+ strap electrode, manufactured by Polar Corporation) provided with fiber fabric to which a silver coating was applied was attached to the rat body surface, and fixed by the two methods described below.

The rear thorax of the rat was shaved, and the skin was washed with ethanol disinfectant, after which the aforementioned three types of biological electrodes (electrodes 1-3) were respectively attached to the left rear thorax and right rear thorax. For all parts, the attachment sites of the electrodes 1-3 were set as close to one another as possible. As an indifferent electrode (body earth), a medical-use biological electrode (F-150S, manufactured by Nihon Kohden Corporation) was attached to the thoracolumbar area. The signals obtained from the respective biological electrodes were analyzed by a measurement apparatus (Polymate AP1124, manufactured by TEAC, Ltd.).

Figure 27:
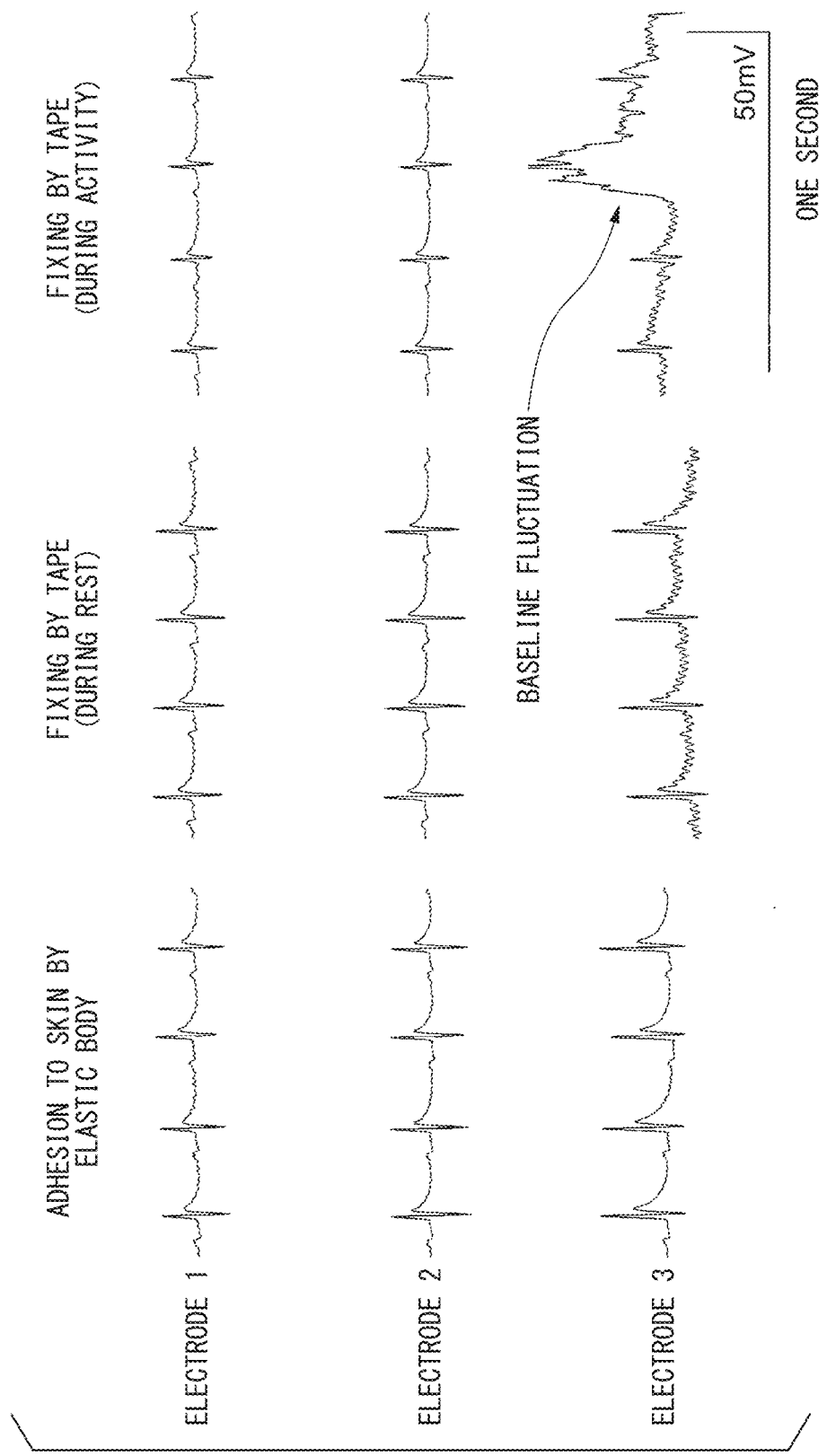
FIG. 27 is a graph which shows electrocardiographic waveforms recorded in Example 3-3, measured using the biological electrode 1 of the present invention, and conventional biological electrodes 2 and 3, wherein the scale bar represents 1 second, 50 mV.

With respect to the left rear thorax and right rear thorax electrodes of the rat, the respective electrodes were fixed by two fixing methods (stretchable band or tape), and measurement was conducted. The measurement results are shown in FIG. 27.

First, in the case where an electrode pad configured by placing a sheet substrate made of PVC on top of the respective electrode was subjected to pressure fixation with a stretchable band, the signals obtained from the three types the electrodes were almost identical, and stable signal recording could be conducted. Next, when the band was removed, and fixation was conducted with medical-use adhesive tape (Silky Pore) (registered trademark), stable signals were recorded from Electrode 1 and Electrode 2, whether the rat was in a state of repose or body movement. However, with respect to signals from Electrode 3, the baseline fluctuated due to body movement, and immixture of hum noise was observed. From the foregoing results, it is clear that the stability of signal measurement by Electrode 1 of the second embodiment of the present invention approximated that of the medical-use Electrode 2, and was superior to the textile Electrode 3.

Example 3-4

Adjustment of Skin Humidity

Changes in skin moisture associated with steaming of skin to which a biological electrode adheres were measured by a skin moisture measurement device (Corneometer), and a comparison was made of skin moisture after six hours of adhesion of a conventional biological electrode and the biological electrode of the second embodiment of the present invention. Forearm skin of human adult males was used as the measurement site.

The subjects conducted desk work involving personal computers and the like in an environment with a room temperature of 26 degrees and a humidity of 40%. Skin moisture at the site before adhesion of each electrode and 6 hours after adhesion of each electrode was measured by a skin moisture measurement instrument (TK59823, manufactured by the German company Courage+Khazaka Electronic). The measurement results are shown in FIG. 10.

Figure 28:
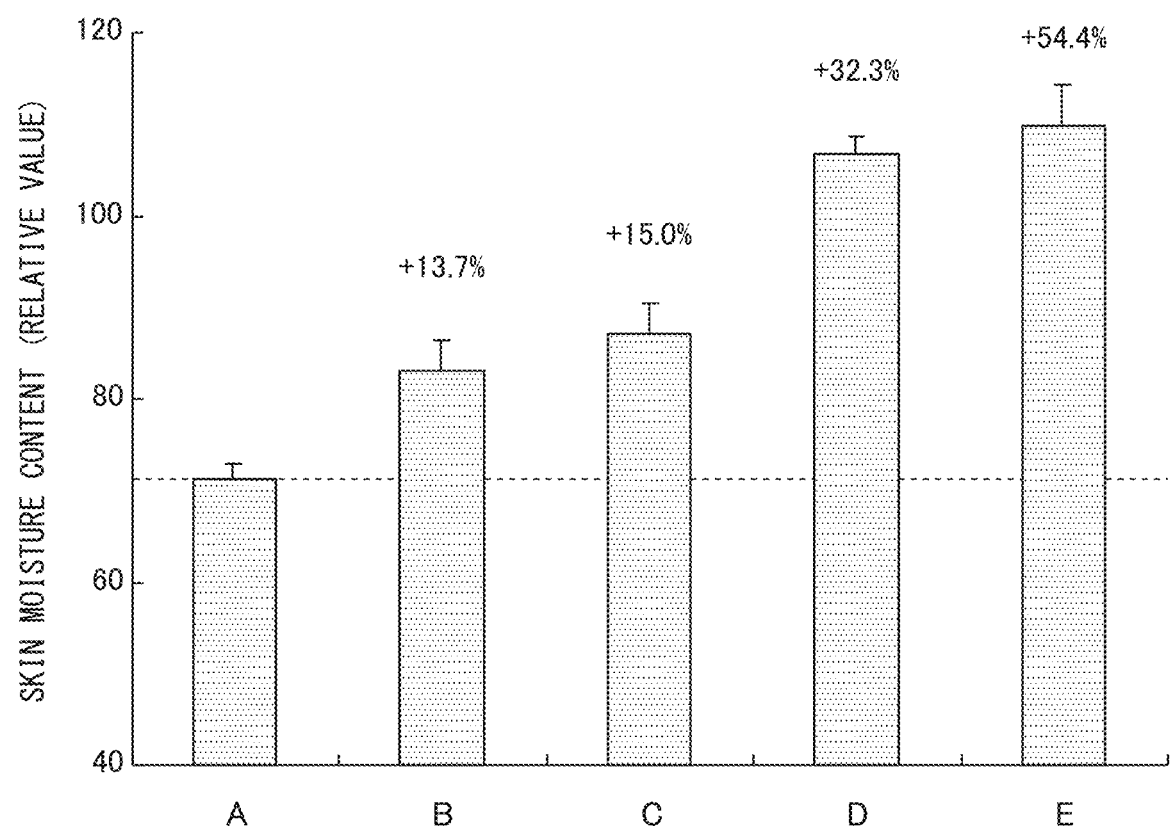
FIG. 28 is a graph which shows results of measurement of moisture content of skin on which is placed a biological electrode B or C of the present invention, or a conventional biological electrode D or E, and comparison of the degree of skin steaming due to each electrode.

The measurement results shown in FIG. 28 show forearm skin moisture prior to electrode attachment (result A) and after 6 hours of electrode adhesion (results B-E) (error bar 1 SD, standard deviation n=10). Result B (+13.7%) are results obtained using the biological electrode of the second embodiment of the present invention provided with apertures in the sheet substrate for aeration; result C (+15%) are results obtained using a biological electrode identical to that of result B except that it was not provided with apertures; result D (+32.3%) are results obtained using a conventional biological electrode to which adhesive gel was applied; and result E (+54.4%) are results obtained using a conventional biological electrode that used a highly adhesive pad as the sheet substrate. The aforementioned results appearing within parentheses indicate the rate of increase in moisture at the adhesion site of each electrode, assuming moisture prior to electrode attachment is 100%.

The specific configurations of the electrodes B-E corresponding to the respective results are as follows.

Electrode B is a biological electrode with the form shown in FIG. 25A, configured by impregnating conductive composite fibers produced in the same manner as Example 3-1 with glycerol, and by arranging in parallel fibers on a 20×30 mm PVC sheet-like substrate to form a 7×12 mm contact. Two apertures with an area of 20 mm$^2$ are provided on the sheet-like substrate, and fixed to the skin surface by an adhesive agent applied to the surface of the PVC sheet.

Electrode C has the same configuration as Electrode B, except that it uses a sheet-like substrate that is not provided with apertures.

Electrode D is a silver-silver chloride medical-use biological electrode (F120S, 18×35 mm, manufactured by Nihon Kohden Corporation) that uses conductive adhesive gel.

Electrode E is a silver-silver chloride medical-use biological electrode (M150, manufactured by Nihon Kohden Corporation, with a diameter of 40 mm) that uses a highly adhesive foam pad.

The biological electrodes B-D were used in a state where they were autonomously fixed to the forearm of the subject.

In the foregoing results, the skin moisture of the conventional electrode D using adhesive gel rose by +32.3%, and the skin moisture of the conventional electrode E using a highly adhesive foam pad rose by +54.4%. On the other hand, in contrast to the conventional types, the rise in skin moisture of electrode B (with apertures) using conductive composite fibers was limited to +13.7%, and that of electrode C (without apertures) was limited to +15.0%. These results indicate that, compared to conventional electrodes, steaming is inhibited with the electrodes of the second embodiment of the present invention. Furthermore, the rise (increase) in skin moisture is more limited with electrode B that provides apertures in the sheet-like substrate than with electrode C that has no apertures, exhibiting the humidity reduction effect due to apertures.

Example 3-5

Comparison of Electrical Properties of Biological Electrodes

Comparison of Combined Resistance of Biological Electrode and Skin

The following three types of biological electrodes 4-6 were respectively attached to human forearm skin at 5 cm electrode intervals, and the combined resistance of the respective biological electrodes and the skin was measured under sinusoidal conditions of 10 Hz using a biological electrode impedance meter (manufactured by Melon Technos Co., Ltd.). With respect to these measurement results, taking the following result of electrode 4 as "1," the resistance ratios normalized by electrode area are shown in the table under the figure. The contact area of each electrode and the impedance are additionally noted. From the aforementioned results, it is shown that the impedance per area of the biological electrode 4 of the second embodiment of the present invention is lowest. Otherwise, the impedance of the sports-use biological electrode 6 when the contact surface was in a dry state was extremely high, rendering measurement impossible with the employed measuring instrument.

Electrode 4 (electrode of the present invention) is a biological electrode wherein the fixation method of the second embodiment was conducted with respect to 12 mm×7 mm contacts which consisted of 15 conductive composite fibers that were produced in the same manner as Example 1 and that were impregnated with glycerol, and which were arranged in parallel on a sheet-like substrate made of PVC. Electrode 4 was set on the surface of human forearm skin, and fixed in place with a stretchable band. At this time, the contact area of the contact part constituted by the aforementioned contacts and the human forearm skin surface was 84 mm$^2$ (7×12 mm).

Electrode 5 (conventional type): an electrode (Vitrode F 150S, manufactured by Nihon Kohden Corporation) obtained by applying conductive gel to a silver-silver chloride electrode was set upon the skin surface, and the sheet-like substrate used in electrode 4 was placed thereon, and fixed in place with a stretchable band. At this time, the contact area of the electrode 5 and the human forearm skin surface was 630 mm$^2$.

Electrode 6 (conventional sports-use biological electrode): a commercial sports heart rate monitor electrode (Smart Fabric Sensor, WearLink+ strap electrode, manufactured by Polar Corporation) provided with fiber woven cloth made of nylon to which a silver coating was applied was set on the skin surface, and fixed in place with a stretchable band. At this time, the contact area of the electrode 6 and the human forearm skin surface was 600 mm$^2$.

The results of measurement of the combined resistance of each electrode and the skin are shown below.

TABLE 3

Combined resistance of electrode and skin

| No. | Electrode | Contact area (mm²) | Impedance (KΩ) | Normalized resistance ratio |
|---|---|---|---|---|
| 4 | Electrode of the present invention (PEDOT-PSS silk + glycerol) | 84 | 1.48 | 1 |
| 5 | Medical test-use electrode (silver-silver chloride electrode + electrolytic gel) Vitrode F 150S, manufactured by Nihon Kohden Corporation | 630 | 105 | 533 |
| 6 | Sports-use biological electrode (silver coated nylon fiber cloth) for sports heart rate monitor, manufactured by Polar Human forearm skin 5 cm electrode interval | 600 | 1.13 (wet) ∞ (dry) | 5.45 (wet) — (dry) |

Reference electrode: silver plate electrode + physiological saline water
Biological electrode impedance meter: Melon Technos (10 Hz, sinusoidal)

Frequency Properties

For purposes of comparing the frequency properties of the below-mentioned electrode 7 provided with conductive composite fibers and the below-mentioned conventional electrode 8 using an electrolyte solution, the frequency properties of the two electrodes were measured using Autolabo (PGSTAT, manufactured by Metrohm Autolab Co., Ltd.), and the results are shown in the below table. It is shown that the impedance of the below-mentioned electrode 7 of the second embodiment of the third aspect of the present invention in the 10 Hz to 10 KHz region is lower than the impedance of the below-mentioned electrode 8 consisting of silk fiber impregnated with a sodium chloride electrolyte solution.

Electrode 7 (electrode of the present invention) consists of contacts of conductive composite fiber of 2 cm length produced in the same manner as Example 3-1 and impregnated with glycerol.

Electrode 8 is an electrode (of 2 cm length) obtained by impregnating the silk fiber (with a fiber diameter of 280 microns) composing electrode 7 with a 0.9% sodium chloride electrolyte solution.

The results of measurement of the frequency properties of each electrode are shown below.

TABLE 4

Frequency properties

| | | Frequency (Hz) | | | |
|---|---|---|---|---|---|
| No. | Electrode | 10 | 100 | 1K | 10K |
| 7 | Electrode of the present invention (PEDOT-PSS silk + glycerol) | 16.0 | 103 | 21.2 | 10.7 |
| 8 | Conventional electrode (using NaCl electrolyte solution) | 103 | 144 | 44.0 | 83.0 |

Impedance (KΩ)

Examples of the Fourth Aspect

Next, the fourth aspect of the present invention is described in further detail with reference to Examples, but the fourth aspect of the present invention is not limited by Examples described below.

Example 4-1

Production of Implantable Electrode Using Conductive Composite Fibers

A silk fiber bundle (produced by Fujix, Ltd.; Taiya No. 9, with a fiber diameter of approximately 280 μm) before composite fiber production was immersed in a solution in which 0.1% EDOT (produced by the German company Heraeus) was added to PEDOT-PSS (CLEVIOS P, produced by the German company Heraeus). Subsequently, the aforementioned silk fiber bundle was energized using a comb-like electrode, and the PEDOT-PSS was electrochemically fixed to the surface and the interior of the silk fiber bundle to obtain a conductive composite fiber bundle comprising the silk fiber bundle and PEDOT-PSS.

The coating at the distal end of a polyimide-coated platiniridium wire (with a diameter of 30 microns) (manufactured by Wire Company, Inc. of California, USA) was removed, and ligated to the conductive composite fiber bundle (with a fiber diameter of approximately 280 microns) that had been fabricated. The ligated portion and the surface of the conductive composite fiber bundle were coated using PDMS (polydimethylsiloxane) (brand name: Sylgard 184, produced by Toray-Dow Corning Co., Ltd.). The coating at the distal end of the conductive composite fiber bundle was stripped away to a depth of 500-2000 microns, exposing the distal end of the conductive composite fiber bundle. The PEDOT-PSS contained in the aforementioned exposed distal end was brought into contact with a stainless steel guide needle (with a diameter of 100 microns, manufactured by Seirin Corporation), and ethanol was applied to conduct electrochemical fixation (adhesion) and produce an implantable electrode.

(Placement of Implantable Electrode)

An SD rat was anesthetized with isoflurane, and subjected to cranial fenestration, and the dura mater was removed to expose the cerebral cortex. Using a motorized actuator (RCD, manufactured by IAI Corporation) fixed on a micromanipulator of a brain stereotaxic instrument (SR-6R, manufactured by Narishige Co., Ltd.), the aforementioned implantable electrode was placed within the cerebral cortex. Specifically, the distal end of the aforementioned electrode was inserted into the left barrel cortex to a subcortical depth of 2 mm in 0.01-0.02 seconds. The platiniridium wire ligated to the aforementioned conductive composite fiber bundle was connected to the head amp of a cranial nerve signal measurement recording analyzer (model: RZ51, manufactured by the American company TDT, Inc.). As a reference electrode, a silver-silver chloride wire was placed on the cortex, and the silver-silver chloride wire was placed under the skull as a body earth. The measured signals were recorded and analyzed with dedicated software (Open EX, open explorer TDT).

The moisture absorption of the composite material composed by the PEDOT-PSS and the silk fiber is slow. For example, when the aforementioned conductive composite fiber bundle in a dry state is immersed in 0.9% NaCl physiological saline water, swelling of the fiber is clearly observed approximately 30 seconds or later after the start of immersion. If the aforementioned conductive composite fiber bundle is inserted into biological tissue at high speed (in a short time, e.g., within 1 second), the aforementioned implantable electrode provided with the aforementioned conductive composite fiber bundle can be set within the body, before the PEDOT-PSS swells due to water absorption, and then declines in strength.

After insertion of the aforementioned implantable electrode into the brain, the conductive composite fiber containing PEDOT-PSS that is stationary within the tissue gradually absorbs body fluid (extracellular fluid or cerebrospinal fluid), swells, and adheres to the surrounding tissue. The adhesion between the conductive composite fiber and the guide needle comes apart due to the moisture absorption, and the conductive composite fiber electrode separates from the guide needle. Thereafter, the guide needle is withdrawn by the micromanipulator, and the conductive composite fiber bundle which is the body of the aforementioned electrode remains within the tissue.

(Recording of Cerebral Action Potential)

Figure 35A:
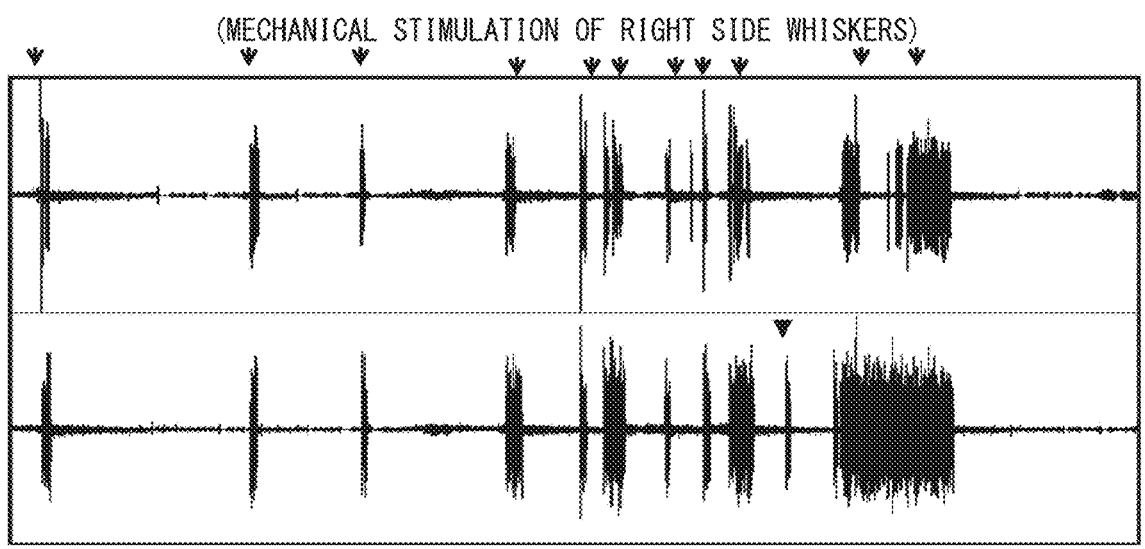
FIG. 35A consists of waveforms showing action potential of a rat cerebral cortex (barrel cortex), recorded by the implantable electrode of the first embodiment of the present invention.

According to the aforementioned insertion method, the aforementioned implantable electrodes with a fiber diameter of 200 microns and a fiber length of 1 mm were placed at two sites of the left barrel cortex in the rat brain at positions of 2 mm depth. The distance between electrodes at this time was 2 mm. FIG. 35A shows the action potential of the rat cerebral cortex (barrel cortex) recorded by the aforementioned electrodes. The upper graph and the lower graph consist of signals respectively detected by the two implanted electrodes. As a result of mechanical stimulation of the right whiskers of the rat, burst-like aggregate action potential was recorded from the two implanted electrodes. Synchronized aggregate potential ↓: arrow mark) and nonsynchronous aggregate potential (▼ mark) are observed in the waveforms of the two electrodes.

Example 4-2

Fabrication of Implantable Electrode

A conductive composite fiber bundle (with a length of 3 mm, and a fiber diameter of 50 microns) produced in the same manner as Example 4-1 was immersed in glycerol, and the fiber was impregnated with glycerol. An insertion guide thread was connected to one end of the obtained conductive composite fiber bundle. As the insertion guide thread, a nylon monofilament suture thread (thickness: 10-0, produced by S&T) with attached curved needle for microsurgery was used. A gold wire (X wire, manufactured by Tanaka Kikinzoku Kogyo Co., Ltd.) from which the insulating coating was stripped was wound around and fixed to the other end of the aforementioned conductive composite fiber bundle, and the fixed part was coated with PDMS (brand name: Sylgard 184, produced by Toray-Dow Corning Co., Ltd.).

(Recording of Aggregate Action Potential of Sciatic Nerve)

Figure 35B:
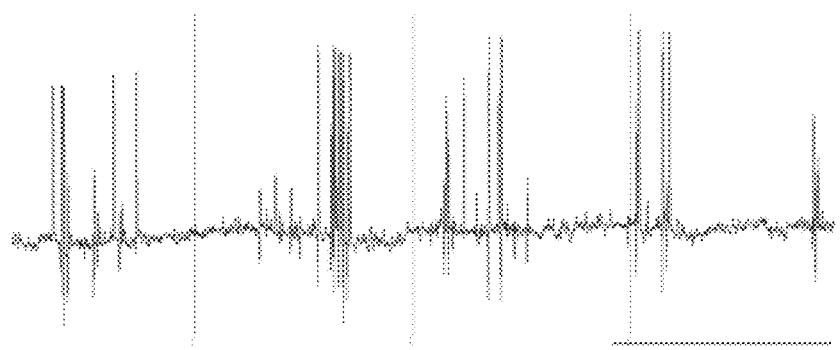
FIG. 35B consists of a waveform (scale bar: 1 second, 50 µV) showing aggregate action potential of a rat sciatic nerve, recorded by the implantable electrode of the third embodiment of the present invention.

A Wistar rat was anesthetized with isoflurane, and an incision was made in the skin of the lower left limb, exposing the left sciatic nerve. The 10-0 guide thread was inserted into the outer membrane of the sciatic nerve bundle under a microscope. Subsequently, the aforementioned conductive composite fiber bundle connected to the guide thread was introduced into the sciatic nerve bundle by pulling on the guide thread. As the aforementioned conductive composite fiber bundle had been treated to delay moisture absorption speed, i.e., as moisture absorption speed had been delayed by the impregnation with glycerol, there was no evidence swelling during the surgical operation, and it was inserted into the tissue (under the outer membrane of the nerve). Fifteen minutes after insertion, the aforementioned conductive composite fiber bundle swelled up, and was fixed to the interior of the tissue. FIG. 35B shows the aggregate action potential (at a scale bar of 1 second, 50 µV) of the rat sciatic nerve that was measured after electrode fixation.

Example 4-3

Recording of Rat Electrocardiogram

Figure 35C:
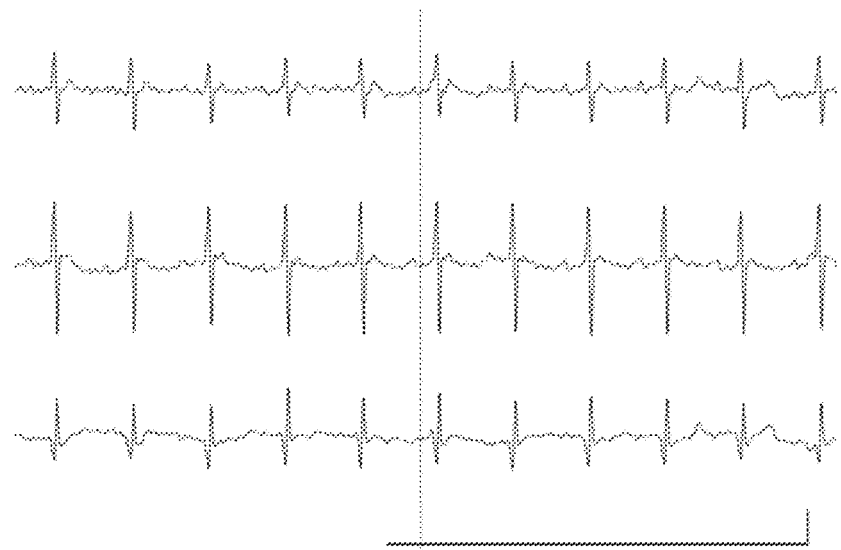
FIG. 35C consists of waveforms (scale bar: 1 second, 50 mV) showing a rat electrocardiogram, recorded by the implantable electrode of the third embodiment of the present invention.

Using conductive composite fiber bundles (with a length of 20 mm, and a wire diameter of 280µ) produced in the same manner as Example 4-1, a rat electrocardiogram was recorded. Under isoflurane anesthesia, the implantable electrodes were set within subcutaneous tissue by ligating the aforementioned conductive composite fiber bundles so that the electrodes were provided to subcutaneous tissue layers at the 3 sites of the right anterior thorax, left anterior thorax, and the hypochondrium of the rat. The conductive composite fiber bundles composing the aforementioned electrodes were connected to a signal cable of a pre-amplifier of a polygraph (AP1124, manufactured by TEAC, Ltd.) via a metallic conductor wire coated with an insulating and water-resistant polymer. FIG. 35C shows a rat electrocardiogram (bipolar lead) (at a scale bar of 1 second, 50 mV) recorded with a sampling frequency of 1 kHz.

Example 4-4

Drug Transport (Drug Delivery) Utilizing Implantable Electrode

A silicone bag storing a drug solution was connected as a reservoir to one end of a conductive composite fiber bundle that was produced by the same method as Example 1, but made relatively long. In this instance, the outer surface of the aforementioned conductive composite fiber bundle was coated (sealed) using PDMS (brand name: Sylgard 184, produced by Toray-Dow Corning Co., Ltd.) to configure the drug delivery path. By means of this coating, an implantable electrode was obtained which was provided with the aforementioned conductive composite fiber bundle at the core, and in which a tube made of PDMS configured the outer shell of the aforementioned delivery path.

For purposes of measuring drug delivery speed with respect to the aforementioned conductive composite fiber bundle configuring the core of the aforementioned electrode, a conductive composite fiber bundle was prepared for testing, and a drug delivery test was conducted.

Figure 36:
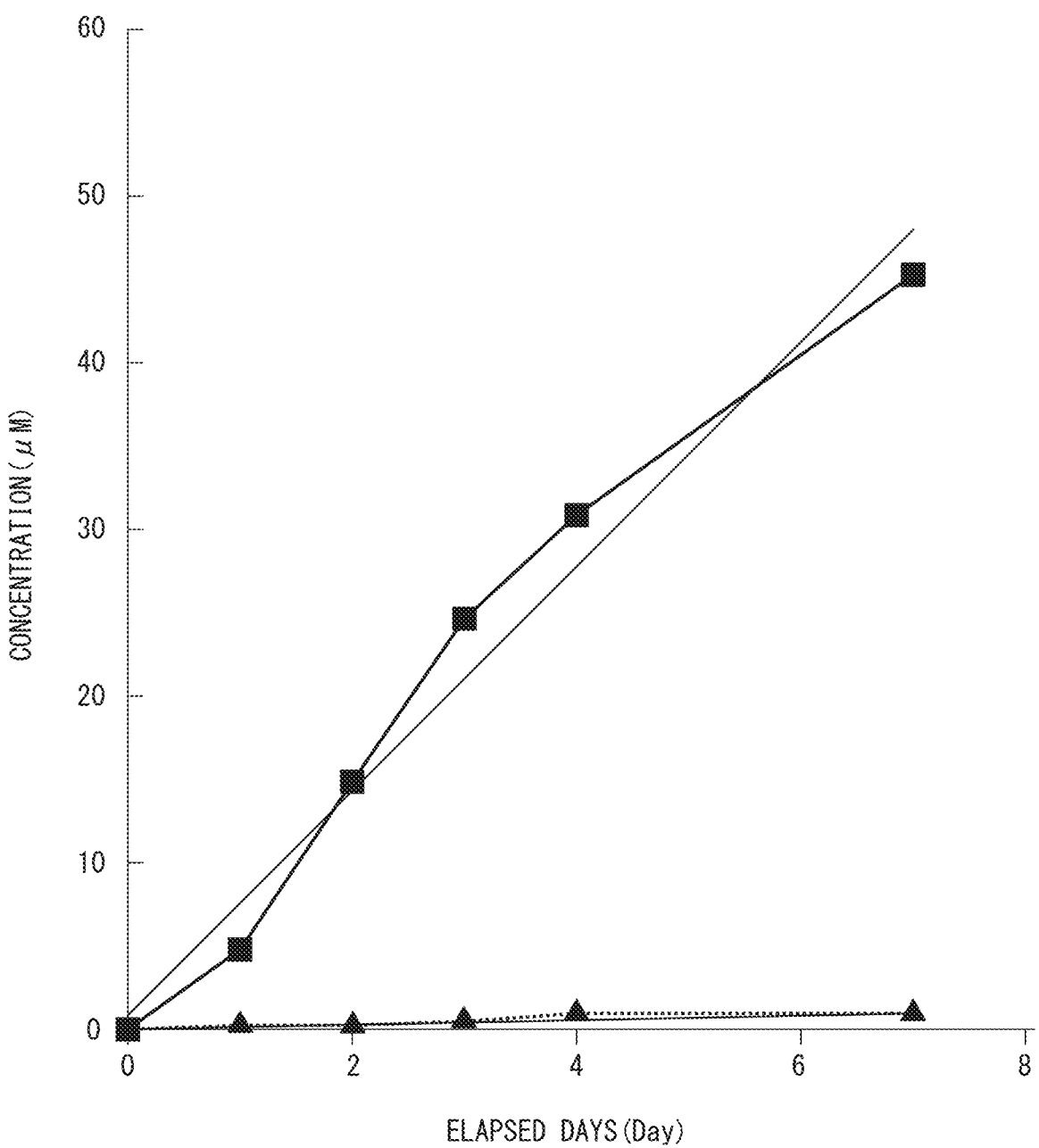
FIG. 36 is a graph which shows drug transport speed in conductive composite fiber bundles coated with PDMS.

First, the central portion of a conductive composite fiber bundle (with a length of 20 mm, and a fiber diameter of 280 microns) produced by the same method as Example 4-1 was coated over a length of 5 mm with PDMS, and one end of the aforementioned conductive composite fiber bundle was immersed in a chamber having 1 mL of physiological saline water containing 100 µM of Lucifer yellow fluorescent material, and the other end was put into it a dish having 0.5 mL of ordinary physiological saline water (without fluorescent material). The water level of the liquid in the chamber containing the Lucifer yellow was set to be 5 mm higher than the water level in the dish containing the ordinary physiological saline water. These were left in a room with a constant temperature of 37 degrees, and the concentration of the Lucifer yellow contained in the physiological saline water in the aforementioned dish was measured at 0, 1, 2, 3, 4, and 7 days after implantation. Using a fluorescence intensity measurement device (multilabel counter, ALVO SX1420, manufactured by PerkinElmer Co., Ltd.) for measurement, measurement was conducted by the fluorometric method. The measurement results are shown in FIG. 36.

By transport of the Lucifer yellow from the aforementioned chamber to the dish via the aforementioned conductive composite fiber bundle, the concentration of the Lucifer yellow in the aforementioned dish increased at a rate of 0.17 µM/day. This result shows that Lucifer yellow permeates (osmotically moves through) conductive composite fibers at a constant speed (in FIG. 36, the ▲ plot and the dotted line).

Example 4-5

A conductive composite fiber bundle was prepared whose central portion was coated with PDMS in the same manner as Example 4-4. However, the aforementioned conductive composite fiber bundle was impregnated with glycerol before being coated with the PDMS. Upon measuring drug delivery speed in the same manner as Example 4-4 using this conductive composite fiber bundle, the concentration of the Lucifer yellow in the dish increased at a rate of 6.7 µM/day (in FIG. 36, the ■ plot and the solid line). From this result, it is shown that drug delivery speed is increased by adding glycerol to the conductive composite fibers.

As one reason for the improvement in drug delivery speed due to impregnation of conductive composite fibers with glycerol, it would seem that when the conductive composite fibers are coated with PDMS, the glycerol prevents the PDMS from penetrating (infiltrating) to the interior of the conductive composite fiber bundle, and the condition of the flow path constituted by the conductive composite fiber bundle is maintained in a condition suited to drug transport.

Example 4-6

Evaluation of Electrode Invasiveness Relative to Central Nervous Tissue

Figure 34A:
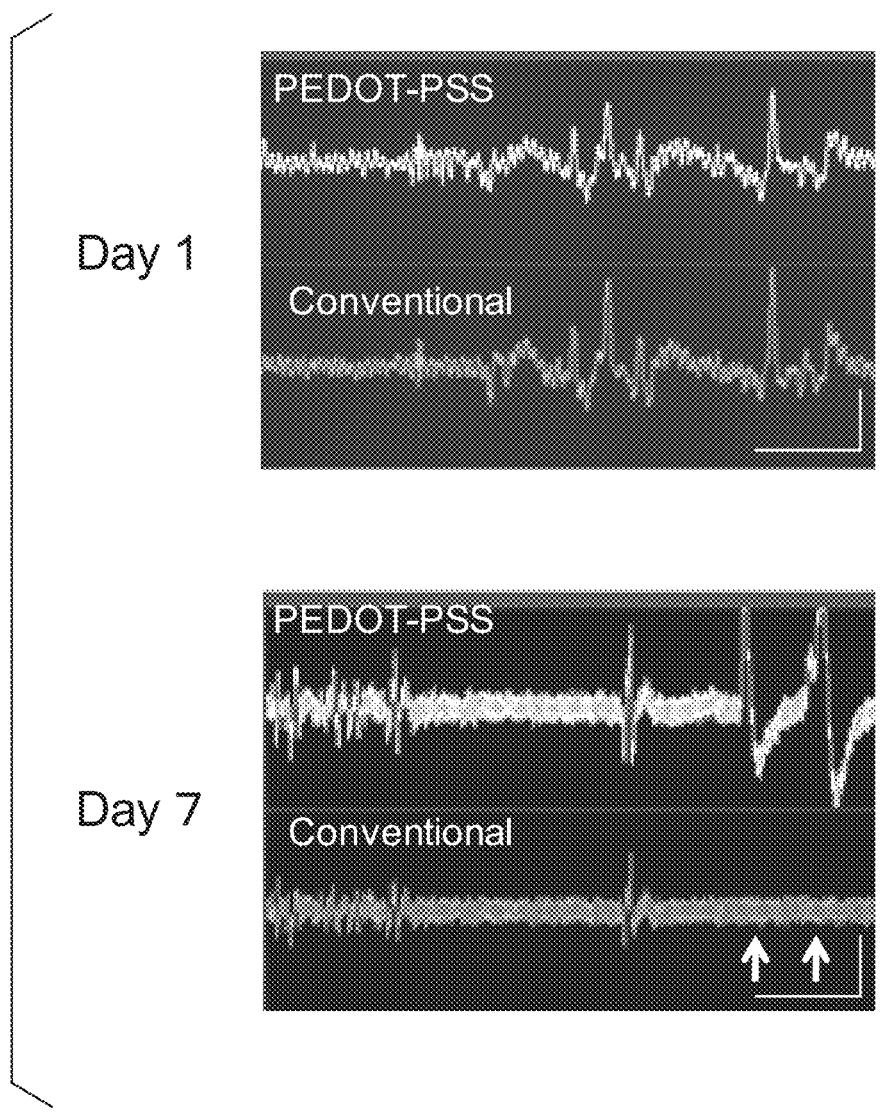
FIG. 34A consists of waveforms (scale bar: 250 ms, 40 mV) of rat-brain aggregate action potential, measured with respective use of a fourth embodiment (PEDOT-PSS) of the implantable electrode, and a conventional metallic electrode.
Figure 34B:
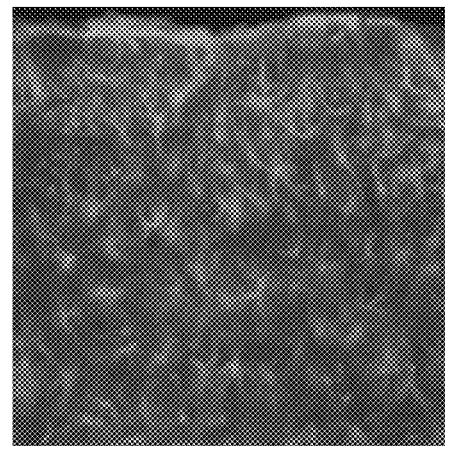
FIG. 34B shows (A) an immunostaining image of a glial cell (astrocyte) of an anti-GFAP antibody of a rat cerebral cortex, in a condition where the electrode is not implanted.
Figure 34C:
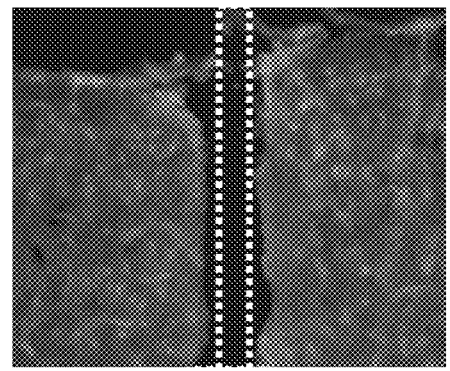
FIG. 34C shows an immunostaining image of a glial cell (astrocyte) of an anti-GFAP antibody of a rat cerebral cortex, and shows the condition of an implantation site (dotted line) of the electrode of the fourth embodiment of the present invention, and its environs.

An ongoing problem has been that implantation of a biological electrode into central nervous system tissue results in occurrence of permanent damage to the central nervous system tissue in a region wider than the size of the electrode, impairing measurement, and this problem requires a remedy. A study was conducted by animal experiments with respect to whether the damage (invasion) inflicted on central nervous tissue by implantation of the aforementioned electrode could be mitigated by administering—via the aforementioned flow path (drug delivery path) of the aforementioned electrode—a drug (GSNO: S-nitrosoglutathione) having the effect of mitigating damage to central nervous tissue, after insertion of the implantable electrode produced in Example 4-4 of the present invention into the brain (FIG. 34B-34D).

The extent of damage to nervous tissue by electrode implantation (insertion) into rat brains was evaluated by immunohistostaining of glial cells (astrocytes) of the rat cerebral cortex, and by loss of nervous tissue. The immunohistostaining was conducted as follows. Frozen slices of 25 microns were prepared from the cerebral cortex subjected to perfusion fixation with 4% paraformaldehyde, combined with anti-GFAP antibodies (MAB360 Chemicon) under conditions of 1:1000 dilution, 4° C., overnight, and also labeled with secondary antibodies (Alexa 568), after which observation was conducted under a fluorescent microscope (BX51, Olympus Corporation).

Figure 34D:
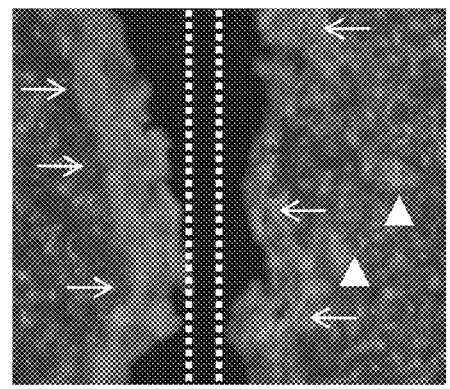
FIG. 34D shows an immunostaining image of a glial cell (astrocyte) of an anti-GFAP antibody of a rat cerebral cortex, and shows the condition of an implantation site (dotted line) of a conventional metallic electrode, and its environs.

When a conventional metallic needle electrode was implanted in the rat brain, and when the cerebral cortex was observed under fluorescent microscope after one week, as shown in FIG. 34D, a pronounced tissue loss (blackened region) had occurred extending beyond the implantation area (dotted line region) of the metallic needle electrode. GFAP-positive glial cells (astrocytes) had propagated in the nervous tissue (▲ in FIG. 34D). In particular, glial cells had propagated in the region of contact with the electrode, forming glial scarring (arrow marks of FIG. 34D). Thus, on the $7^{th}$ day after electrode implantation, pronounced tissue loss, formation of glial scarring (arrow marks), and glial cell clusters (▲ marks) were observed.

Using a conventional metallic needle electrode implanted in this manner, the aggregate action potential of the rat cerebral cortex was measured. After electrode implantation, measurement was conducted on the $1^{st}$ day and the $7^{th}$ day. The results are shown on the lower levels (conventional) (scale bar 250 ms, 40 mV) of FIG. 34A. Measured signals were satisfactory on the $1^{st}$ day, but a contraction of measured waveforms and a loss of spikes were observed on the $7^{th}$ day. In FIG. 34A, Day 1 is the record of measurement on the $1^{st}$ day after electrode implantation, and Day 7 is the record of measurement on the $7^{th}$ day after electrode implantation. The arrow marks indicate the loss of spikes.

On the other hand, after insertion of the implantable electrode produced in Example 4-4 into the rat brain, an anti-inflammatory agent (GSNO) was administered at 15 µg/day per 250 g of body weight via the aforementioned drug delivery path of the aforementioned electrode.

The speed of drug delivery was adjusted by a compact osmotic pump (manufactured by the American company Alzet, Inc.) connected to the aforementioned drug delivery path. In the case of the Example in which the anti-inflammatory agent was administered, tissue loss was less than with the conventional electrode, and tissue loss was limited to the electrode implantation area (dotted-line region) (FIG. 34C). Propagation of glial cells in the nervous tissue was minor, and no clear glial scarring was observed in the area of contact with the electrode (FIG. 34C). In FIG. 34C, GSNO was administered to the environs of the electrode, and even at the $7^{th}$ day after electrode implantation, tissue loss was localized to the electrode implantation region (dotted line), and there was also little propagation of glial cells in the tissue.

For purposes of comparison, FIG. 34B shows fluorescent immunostaining of glial cells in a normal cerebral cortex without electrode implantation.

Using the electrode of Example 4 of the present invention implanted in this manner, the aggregate action potential of a rat cerebral cortex was measured. Measurement was conducted on the 1st and the 7th day after electrode implantation. The results are shown on the upper level of FIG. 34A (PEDOT-PSS) (scale bar 250 ms, 40 mV). Satisfactory waveforms were observed with respect to measured signals of both the first and the seventh days.

The respective configurations and their combinations in the various embodiments described above are exemplary, and additions, omissions, substitutions, and other modifications of configuration are possible within a scope that does not deviate from the intent of the present invention. Moreover, the present invention is not limited by the respective embodiments, and is limited only by the scope of the claims.

INDUSTRIAL APPLICABILITY

The present invention is able to provide conductive polymer fibers with superior conductivity, strength in dry and wet states, and flexibility, and a biological electrode provided therewith.

It provides a method and a device for producing conductive polymer fibers which are capable of causing impregnation or adhesion of a conductor containing PEDOT-PSS in or to base fibers, and continuously conducting electrochemical polymerization and fixation thereof, and producing with satisfactory productivity conductive polymer fibers having superior conductivity and durability.

The biological electrode of the present invention can be widely used as an body surface mounting type implantable biological electrode capable of long-term continuous use in a wide range of fields including medical treatment, health promotion, information technology, wearable computers, and the like. It is possible to provide a biological electrode that has an improved wear feeling compared to conventional electrodes, and a biological signal measurement device provided with the biological electrode.

The implantable electrode of the present invention can be widely used as an implantable electrode in a wide range of fields including medical treatment, health promotion, information technology, wearable computers, and the like. More specifically, it can be used in electrical stimulation therapy involving deep brain stimulation and the like, implantable electrodes for nervous action recording, brain-machine interfaces, and so on.

It is possible to offer an implantable electrode which enables detection of weak electrical signals from within a living body, which has excellent biocompatibility, and which has a low degree of invasiveness relative to biological tissue.

BRIEF DESCRIPTION OF THE REFERENCE SYMBOLS

2: conductive polymer fiber
3: fixing cord
4: rubber band
5: metal conductor wire
6: human body surface
33: metal or carbon
34: conductor
54: conductor
63: insulating layer
L: diameter of base fiber
h: thickness of coated conductor
10, 20, 30, 40, 50, 60: conductive polymer fiber
11, 21, 31, 41, 51, 61: base fiber
12, 22, 32, 42, 52, 62: conductor
210, 250: device for producing conductive polymer fiber (production device)
202: multiple electrodes (positive terminals)
221: comb teeth-like electrodes (multiple electrodes; positive terminals)
221a: comb tooth (electrode)
221b: terminal
222: rotor electrode (pulley-like electrode)
222a: pulley
222b: groove
222c: metal shaft
203: multiple electrodes (negative terminals)
231: comb teeth-like electrodes (multiple electrodes; negative terminals)
231a: comb tooth (electrode)
231b: terminal
231c: rotor electrode (roller-like electrode)
232a: roller
232b: outer circumferential surface
232c: metal shaft
252: single (monopolar) electrode (positive terminal)
253: single (monopolar) electrode (cathode)
204: conductor solution
205, 255: immersion container
206, 256: bobbin
207, 257: chamber (humidity regulator)
208, 258: drier
209, 259: reel unit
310: biological electrode
311: contact
312: first frame
313: second frame
314: signal cable
H: hair (head hair)
S: skin (scalp)
320: biological electrode
321: contact
322: third frame
323: fourth frame
324: signal cable
321a: conductive composite fiber
321b: metal wire material
321c: insulating coating material
321e: conductive composite fiber
321f: metal wire
321g: core material
321z: insulating coating material
N: low-tension net
330: biological electrode
331: contact
332: contact part
333: substrate (base material)
334: signal cable
335: holder
336: aperture
337: humidity control pad
338: electrode pad
339: amp (external device)
B: body (torso)
T: undershirt (shirt)
401: conductive composite fiber
402: electric cable (metal conductor wire)
403: wire connection part
404: polymer
405: needle (guide needle)
406: thread
407: reservoir
408: chamber
409: tube connector
410, 420, 430, 440: implantable electrode
N': nerve cord

The invention claimed is:

1. A conductive polymer fiber, wherein a conductor containing a conductive polymer impregnates and adheres to base fibers, the base fibers are fibers which are at least one selected from the group consisting of nylon, polyester, acrylic, aramid, polyurethane, and carbon fiber, the conductor is arranged with close adhesion to said base fibers among a plurality of said base fibers so that the conductor bonds the base fibers to each other, the base fibers are straight fibers, the conductor contains sphingosine as an additive, and a concentration of the additive in the conductor is 0.1 to 50 wt %, and the interior of said base fibers is impregnated with said conductor, metal or carbon coats an exterior surface of said base fibers, and an exterior surface of said metal or carbon coating is coated by said conductor.

2. The conductive polymer fiber according to claim 1, wherein said conductor coats the circumference of said base fibers.

3. The conductive polymer fiber according to claim 1, wherein the metal coats the circumference of said base fibers, and the metal is at least one selected from the group consisting of titanium, gold, silver and copper.

4. The conductive polymer fiber according to claim 1, wherein the carbon coats the circumference of said base fibers.

5. The conductive polymer fiber according to claim 1, wherein the metal coats the circumference of said base fibers, and the metal is gold.

6. The conductive polymer fiber according to claim 1, wherein an insulating layer is further arranged on a circumference of the conductive polymer fiber.

7. The conductive polymer fiber according claim 1, wherein the conductor comprises at least one selected from the group consisting of surface active agents, alcohols, natural polysaccharides, sugar alcohols, acrylic resins, and dimethyl sulfoxide.

8. The conductive polymer fiber according to claim 1, wherein the base fibers consist of polyurethane.

9. The conductive polymer fiber according to claim 1, wherein the base fibers consist of carbon fiber.

10. A conductive polymer fiber, wherein a conductor containing a conductive polymer impregnates and adheres to base fibers, the base fibers are fibers which are at least one selected from the group consisting of nylon, polyester, acrylic, aramid, polyurethane, and carbon fiber, the conductor is arranged with close adhesion to said base fibers among a plurality of said base fibers so that the conductor bonds the base fibers to each other, the base fibers are straight fibers, the conductor contains phosphatidylcholine as an additive, and a concentration of the additive in the conductor is 0.1 to 50 wt %, and the interior of said base fibers is impregnated with said conductor, metal or carbon coats an exterior surface of said base fibers, and an exterior surface of said metal or carbon coating is coated by said conductor.

11. The conductive polymer fiber according to claim 10, wherein said conductor coats the circumference of said base fibers.

12. The conductive polymer fiber according to claim 10, wherein the metal coats the circumference of said base fibers, and the metal is at least one selected from the group consisting of titanium, gold, silver and copper.

13. The conductive polymer fiber according to claim 10, wherein the carbon coats the circumference of said base fibers.

14. The conductive polymer fiber according to claim 10, wherein the metal coats the circumference of said base fibers, and the metal is gold.

15. The conductive polymer fiber according to claim 10, wherein an insulating layer is further arranged on a circumference of the conductive polymer fiber.

16. The conductive polymer fiber according claim 10, wherein the conductor comprises at least one selected from the group consisting of surface active agents, alcohols, natural polysaccharides, sugar alcohols, acrylic resins, and dimethyl sulfoxide.

17. The conductive polymer fiber according to claim 10, wherein the base fibers consist of polyurethane.

18. The conductive polymer fiber according to claim 10, wherein the base fibers consist of carbon fiber.

\* \* \* \* \*